(12) United States Patent
Frei et al.

(10) Patent No.: US 7,146,211 B2
(45) Date of Patent: Dec. 5, 2006

(54) SIGNAL QUALITY MONITORING AND CONTROL FOR A MEDICAL DEVICE SYSTEM

(75) Inventors: Mark G. Frei, Lawrence, KS (US); Ivan Osorio, Leawood, KS (US)

(73) Assignee: Medtronic, Inc., Minneapolis, MN (US)

( * ) Notice: Subject to any disclaimer, the term of this patent is extended or adjusted under 35 U.S.C. 154(b) by 421 days.

(21) Appl. No.: 10/687,348

(22) Filed: Oct. 15, 2003

(65) Prior Publication Data

US 2004/0138580 A1 Jul. 15, 2004

Related U.S. Application Data

(60) Provisional application No. 60/503,803, filed on Sep. 19, 2003, provisional application No. 60/418,580, filed on Oct. 15, 2002.

(51) Int. Cl.
*A61N 1/00* (2006.01)

(52) U.S. Cl. ........................................................ 607/2

(58) Field of Classification Search ............ 607/39–46, 607/2; 128/901; 600/544, 545
See application file for complete search history.

(56) References Cited

U.S. PATENT DOCUMENTS

| | | |
|---|---|---|
| 3,522,811 A | 8/1970 | Schwartz et al. |
| 3,850,161 A | 11/1974 | Liss |
| 3,863,625 A | 2/1975 | Viglione et al. |
| 3,967,616 A | 7/1976 | Ross |
| 3,993,046 A | 11/1976 | Fernandez et al. |
| 4,019,518 A | 4/1977 | Maurer et al. |
| 4,038,536 A | 7/1977 | Feintuch |
| 4,295,474 A | 10/1981 | Fischell |
| 4,373,527 A | 2/1983 | Fischell |
| 4,417,592 A | 11/1983 | Roy |
| 4,566,464 A | 1/1986 | Piccone et al. |
| 4,581,758 A | 4/1986 | Coker et al. |
| 4,610,259 A | 9/1986 | Cohen et al. |
| 4,702,254 A | 10/1987 | Zabara |
| 4,944,299 A | 7/1990 | Sulvian |
| 5,269,303 A | 12/1993 | Wernicke et al. |
| 5,299,569 A | 4/1994 | Wernicke et al. |
| 5,311,869 A | 5/1994 | Nappholz et al. |
| 5,311,876 A | 5/1994 | Olsen et al. |
| 5,331,966 A | 7/1994 | Bennett |
| 5,335,657 A | 8/1994 | Terry, Jr. et al. |
| 5,487,754 A | 1/1996 | Snell et al. |
| 5,626,145 A | 5/1997 | Clapp et al. |

(Continued)

OTHER PUBLICATIONS

Alan V. Oppenheim & Ronald W. Schafer, Digital Signal Processing, Prentice-Hall, Inc., Englewood Cliffs, New Jersey, 1975, p. 18-24.

(Continued)

*Primary Examiner*—George Manuel
(74) *Attorney, Agent, or Firm*—Banner & Witcoff, Ltd.

(57) ABSTRACT

Method and apparatus for detecting possible interference in a neurological signal received from a monitoring element of a medical device system. The monitoring element monitors a condition or a symptom of a nervous system disorder being treated and provides a neurological signal to the medical device system for purposes of providing closed-loop feedback control. The system analyzes various parameters of the received signal by taking instantaneous measurements of data points in moving window and thereby determining whether the signal is of poor quality. If the signal is of determined poor quality, it is removed from consideration in the closed-loop feedback control system until it is determined that the signal quality has sufficiently been restored.

37 Claims, 33 Drawing Sheets

(CR-ECS configuration)

U.S. PATENT DOCUMENTS

| | | | |
|---|---|---|---|
| 5,683,422 | A | 11/1997 | Rise |
| 5,713,922 | A | 2/1998 | King |
| 5,713,923 | A | 2/1998 | Ward et al. |
| 5,716,377 | A | 2/1998 | Rise et al. |
| 5,720,770 | A | 2/1998 | Nappholz et al. |
| 5,743,860 | A | 4/1998 | Hively et al. |
| 5,752,976 | A | 5/1998 | Duffin et al. |
| 5,792,186 | A | 8/1998 | Rise |
| 5,978,702 | A | 11/1999 | Ward et al. |
| 5,987,352 | A | 11/1999 | Klein |
| 5,995,868 | A | 11/1999 | Dorfmeister |
| 6,016,449 | A | 1/2000 | Fischell et al. |
| 6,018,682 | A | 1/2000 | Rise |
| 6,066,163 | A | 5/2000 | John |
| 6,083,248 | A | 7/2000 | Thompson |
| 6,094,598 | A | 7/2000 | Elsberry et al. |
| 6,115,628 | A | 9/2000 | Stadler |
| 6,117,066 | A | 9/2000 | Abrams et al. |
| 6,128,537 | A | 10/2000 | Rise |
| 6,128,538 | A | 10/2000 | Fischell et al. |
| 6,134,474 | A | 10/2000 | Fischell et al. |
| 6,200,265 | B1 | 3/2001 | Walsh et al. |
| 6,224,549 | B1 | 5/2001 | Drongelen |
| 6,227,203 | B1 | 5/2001 | Rise et al. |
| 6,230,049 | B1 | 5/2001 | Fischell et al. |
| 6,236,882 | B1 | 5/2001 | Lee |
| 6,337,997 | B1 | 1/2002 | Rise |
| 6,341,236 | B1 | 1/2002 | Osorio et al. |
| 6,353,754 | B1 | 3/2002 | Fischell et al. |
| 6,356,784 | B1 | 3/2002 | Lozano et al. |
| 6,360,122 | B1 | 3/2002 | Fischell et al. |
| 6,366,813 | B1 | 4/2002 | Di Lorenzo |
| 6,366,814 | B1 | 4/2002 | Boveja et al. |
| 6,374,140 | B1 | 4/2002 | Rise |
| 6,427,086 | B1 | 7/2002 | Fischell et al. |
| 6,459,936 | B1 | 10/2002 | Fischell et al. |
| 6,466,822 | B1 | 10/2002 | Pless |
| 6,473,639 | B1 | 10/2002 | Fischell et al. |
| 6,480,743 | B1 | 11/2002 | Kirkpatrick et al. |
| 6,505,067 | B1 | 1/2003 | Lee |
| 6,560,486 | B1 | 5/2003 | Osorio et al. |
| 6,587,727 | B1 | 7/2003 | Osorio et al. |
| 6,591,138 | B1 | 7/2003 | Ficshell et al. |
| 6,597,954 | B1 | 7/2003 | Pless et al. |
| 6,609,030 | B1 | 8/2003 | Rezai et al. |
| 6,647,296 | B1 | 11/2003 | Fischell et al. |
| 6,810,285 | B1* | 10/2004 | Pless et al. ............ 600/544 |
| 6,819,956 | B1* | 11/2004 | DiLorenzo ............ 607/45 |
| 2002/0013614 | A1 | 1/2002 | Thompson |
| 2003/0140039 | A1* | 7/2003 | Ferguson et al. ............ 707/4 |

OTHER PUBLICATIONS

Gotman J., & Gloor, P., "Automatic Recognition and Quantification of Linterictal Epileptic Activity in the Human Scalp EEG", Electroencephalography and Clinical Neurophysiology, 1976, 41:513-529.

B. Litt and J. Echauz, "Prediction of Epileptic Seizures", 1 The Lancet Neurology May 22, 2002.

H. Qu & J. Gotman, "A Seizure Warning System For Long-term Epilepsy Monitoring", 45 Neurology 2250, 1995.

J. Gotman, "Automatic Recognition of Epileptic Seizures in the EEG", 54 Electroencephalography and Clinical Neurophysiology at 530-540, 1982.

Lapkin et al., "The Electroencephalogram in Childhood Basilar Artery Migraine", 27Neurology 580-583, Jun. 1977).

Murro et al., "Computerized Seizure Detection of Complex Partial Seizures", 79 Electroencephalography and Clinical Neurophysiology 330-333 (1991).

P. Rajna and C. Lona, "Sensory Stimulation for Inhibition of Epileptic Seizures", 30(2) Epilepsia 168-174, 1989.

R.P. Lesser et al., "Brief Bursts of Pulse Stimulation Terminate Afterdischarges Caused by Cortical Stimulation", Neurology 53, Dec. 1999.

Webber, W.R.S. et al., "Automatic EEG Spike Detection: What Should the Computer Imitate", 87 Electroencephalography and Clinical Neurophysiology 330-333 (1993).

Grassberger, Peter et al., "Characterization of Strange Attractors" vol. 50, No. 5., The American Physical Society, Jan. 31, 1983.

Iasemidis, L. D. and Sackellares, J. C. "Chaos Theory and Epilepsy". The Neuroscientist, 2:118—126, 1996.<retrieved from http://citeseer.ist.psu.edu./iasemidis96chaos.html >.

Elger, Christian E., et al., "Short Communication: Seizure Prediction By Non-Linear Time Series Analysis of Brain Electrical Activity" European Journal of Neuroscience, vol. 10, pp. 786-789 (1998).

Gotman, J., "Seizure Recognition and Analysis", Montreal Neurological Institute and Department of Neurology and Neurosurgery, McGill University, Montreal, Quebec. H3A 2B4 (Canada).

Vachtsevanos, G.J., et al. "Neuro-Fuzzy Approaches to Decision Making: A Comparative Study With An Application to Check Authorization" Journal of Intelligent and Fuzzy Systems, vol. 6, pp. 259-278 (1998).

Osorio, Ivan, et al., "Real-Time Automated Detection and Quantitative Analysis of Seizures and Short-Term Prediction of Clinical Onset" Epilepsia, vol. 39(6) pp. 615-627, (1998).

PCT International Search Report.

* cited by examiner

FIG. 1 (CR-ECS configuration)

FIG. 2 (Bedside device configuration)

Sense electronics configuration

FIG. 4 (Blanking Circuitry)

FIG. 5 (Hardware interface processor)

FIG. 6 (Signal processor)

FIG. 7 (User interface processor)

FIG. 8 (Seizure detection algorithm)

FIG. 10 (Epilepsy external device diagram)

FIG. 11 (Epilepsy implantable device diagram)

FIG. 22 (Clustering)

Graph of $P(x; 0, 8, \{\})$:

Graph of $P(x; 0, 8, \{1,1,3,3,3,5,6,6,8\})$:

Graph of $P(x; 0, 65536, \{\})$

Example 3: $z_{min} = 0$, $z_{max} = 65536$, Empirical Data: $\{\}$

Graph of $P(x; 0, 65536, \{\text{round}([\{35.2, 41.3, 18.9, 55.1]*(250/12))\}\}) = P(x; 0, 65536, \{394, 733, 860, 1148\})$ Example 4: $z_{min} = 0$, $z_{max} = 65536$, Empirical Data: $\{923, 1058\}$ Graph of $P(x; 0, 6550, \{\})$

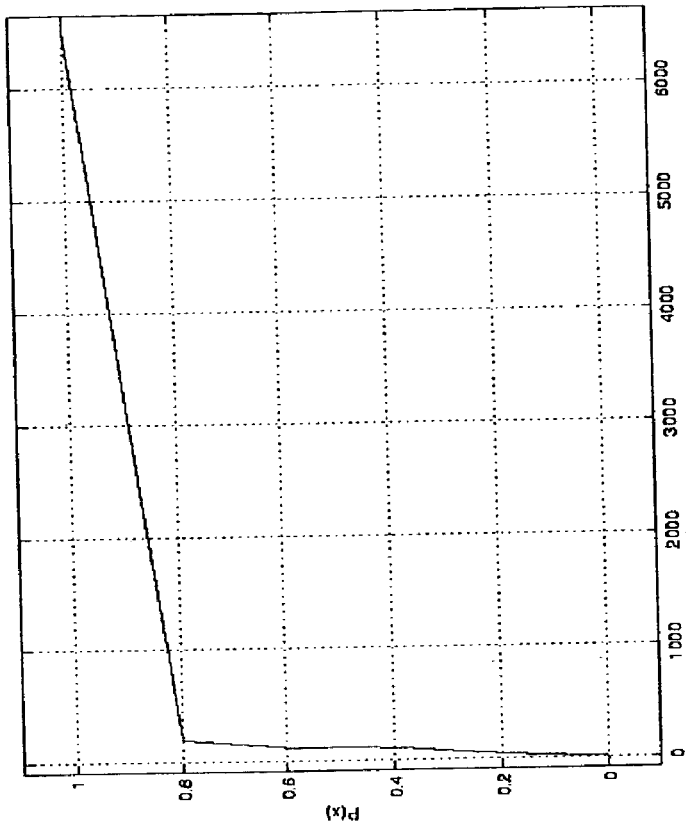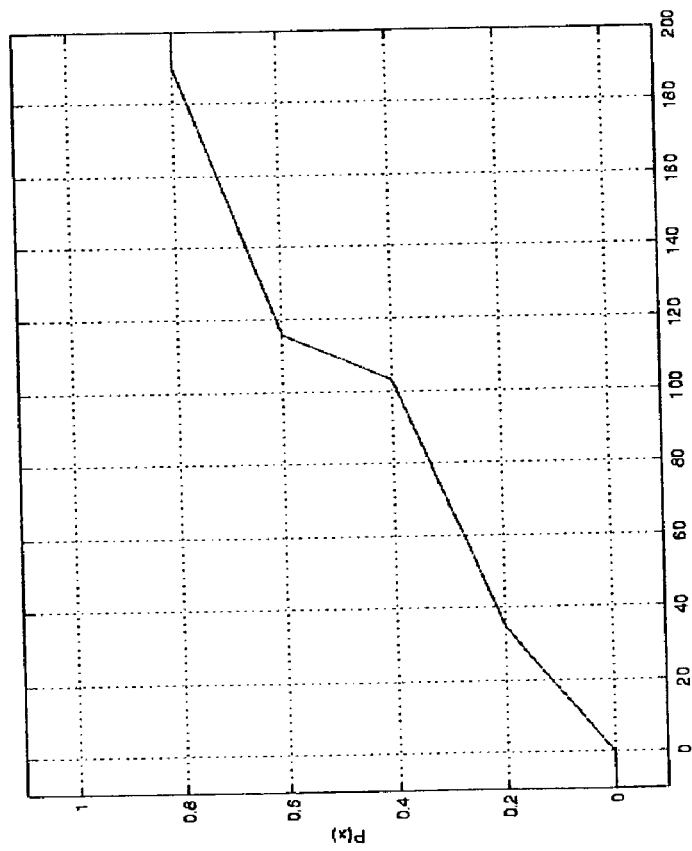
FIG. 33
Graph of $P(x; 0, 6550, \{34.7, 103.1, 115.6, 189.9\})$
Example 6: $z_{min} = 0$, $z_{max} = 6550$, Empirical Data: $\{34.7, 103.1, 115.6, 189.9\}$

SIGNAL QUALITY MONITORING AND CONTROL FOR A MEDICAL DEVICE SYSTEM

This application claims priority to U.S. Provisional Application Ser. No. 60/418,580 filed Oct. 15, 2002 and Ser. No. 60/503,803 filed Sep. 19, 2003, which are incorporated herein by reference in their entireties.

FIELD OF THE INVENTION

The present invention relates to the detection and the treatment of nervous system disorders and more particularly to a method and a medical device system for analyzing neurological signals received from monitoring elements to determine signal quality.

BACKGROUND OF THE INVENTION

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, and multiple sclerosis (MS). Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia. As an example, epilepsy is the most prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. (A neurological event is an activity that is indicative of a nervous system disorder. A seizure is a type of a neurological event.) This electrical excitability of the brain may be likened to an intermittent electrical overload that manifests with sudden, recurrent, and transient changes of mental function, sensations, perceptions, and/or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, drug infusion, and/or brain temperature control. Each of these treatment modalities can be operated using closed-loop feedback control. Such closed-loop feedback control techniques receive from a monitoring element a neurological signal that carries information about a symptom or a condition or a nervous system disorder. Such a neurological signal can include, for example, electrical signals (such as EEG, ECoG, and/or EKG), chemical signals, other biological signals (such as change in quantity of neurotransmitters), temperature signals, pressure signals (such as blood pressure, intracranial pressure or cardiac pressure), respiration signals, heart rate signals, pH-level signals, and peripheral nerve signals (cuff electrodes on a peripheral nerve). Monitoring elements can include, for example, recording electrodes or various types of sensors.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

Monitoring of a neurological signal for the detection of a nervous system disorder, however, has its difficulties. For example, the monitoring system can become degraded for various reasons including, for example, a broken connection, a faulty contact, external disturbance, degradation of the line, excessive electrical noise from devices (caused by faulty grounding, too many devices, etc.), movement of the wires causing inductance, patient moving around and causing displacement of components relative to each other, other physiologic generators such as blinking and eye movements, EKG, glossokinetic potential (swallowing or tongue movements), etc.

To account for such degradation, for example, U.S. Pat. No. 5,995,868 discloses the possibility of utilizing online signal quality control methods to detect various form of signal degradation and warn the user or others. As another example, J. Gotman discloses a system that performs pre-filtering and artifact rejection of EEG signals for purposes of detecting a seizure. J. Gotman, "Automatic Recognition of Epileptic Seizures in the EEG," Electroencephalography and clinical Neurophysiology, Vol. 54: pp. 530–540 (1982). Gotman discloses the use of a fixed control using a small time window. For example, if the received data is beyond a threshold amplitude for sample points over all channels, the system cancels all detections in all channels for the current and previous epoch.

Since Gotman utilizes a fixed time window wherein a single data point is considered, an instantaneous determination is made whether or not to ignore a given signal over an epoch. It may be desirable, however to consider data points over a given period of time. Instantaneous and piecemeal determinations may not provide a sufficiently accurate and flexible technique for detecting and removing from consideration channels have poor signal quality.

Thus, it would be an advancement in the art to provide a method or apparatus that can monitor received signal and determine based on signal quality over a period of time whether signal degradation has occurred.

BRIEF SUMMARY OF THE INVENTION

In an embodiment, a medical device system is provided for analyzing neurological signals received from monitoring elements to determine signal quality. The medical device system comprises one or more monitoring elements, each generating a neurological signal of a sensed neurological condition to provide closed-loop feedback control of a treatment therapy and, optionally, a therapy device providing treatment therapy to the patient in response to the sensed neurological condition. In accordance with the invention, the medical device system also comprises one or more software modules for analyzing the received neurological signals and assessing their quality. In particular, the software module generates a plurality of instantaneous data points of the received neurological signal for a time window. The data points may represent one or more particular characteristics of the neurological signal. Various characteristics of the neurological signal may be monitored to assess signal quality including, but not limited to, a clipping artifact and a mains artifact. The time window is preferably a moving time window of a duration to allow for proper function for the desired application.

A neurological signal is considered to be exhibiting poor signal quality if the relative number of data points exhibiting poor signal quality within the time window has exceeded a predetermined threshold. In the event that a neurological signal is considered to exhibit poor signal quality, the signal for that particular channel is ignored in the analysis for closed-loop feedback control of the treatment therapy. Alternatively, a substituted signal is provided. The signal remains continuously monitored and analyzed for quality assessment as described above. Once the number of data points exhibiting poor signal quality drops below a second threshold, the signal is then restored to consideration as part of the analysis for closed-loop feedback control.

In a preferred embodiment, the invention is implemented within a medical device system for treating an epilepsy disorder using a seizure detection algorithm to detect a possible seizure onset based on received electrical signals from the patient's brain. Of course, other embodiments are possible for treatment of other nervous system disorders, using other forms of treatment therapies, having other forms of sensed neurological signals, and affecting other portions of the human body.

BRIEF DESCRIPTION OF THE DRAWINGS

FIGS. 28–33 depict examples of the interpolating empirical probability function for various values.

DETAILED DESCRIPTION OF THE INVENTION

Figure 1:
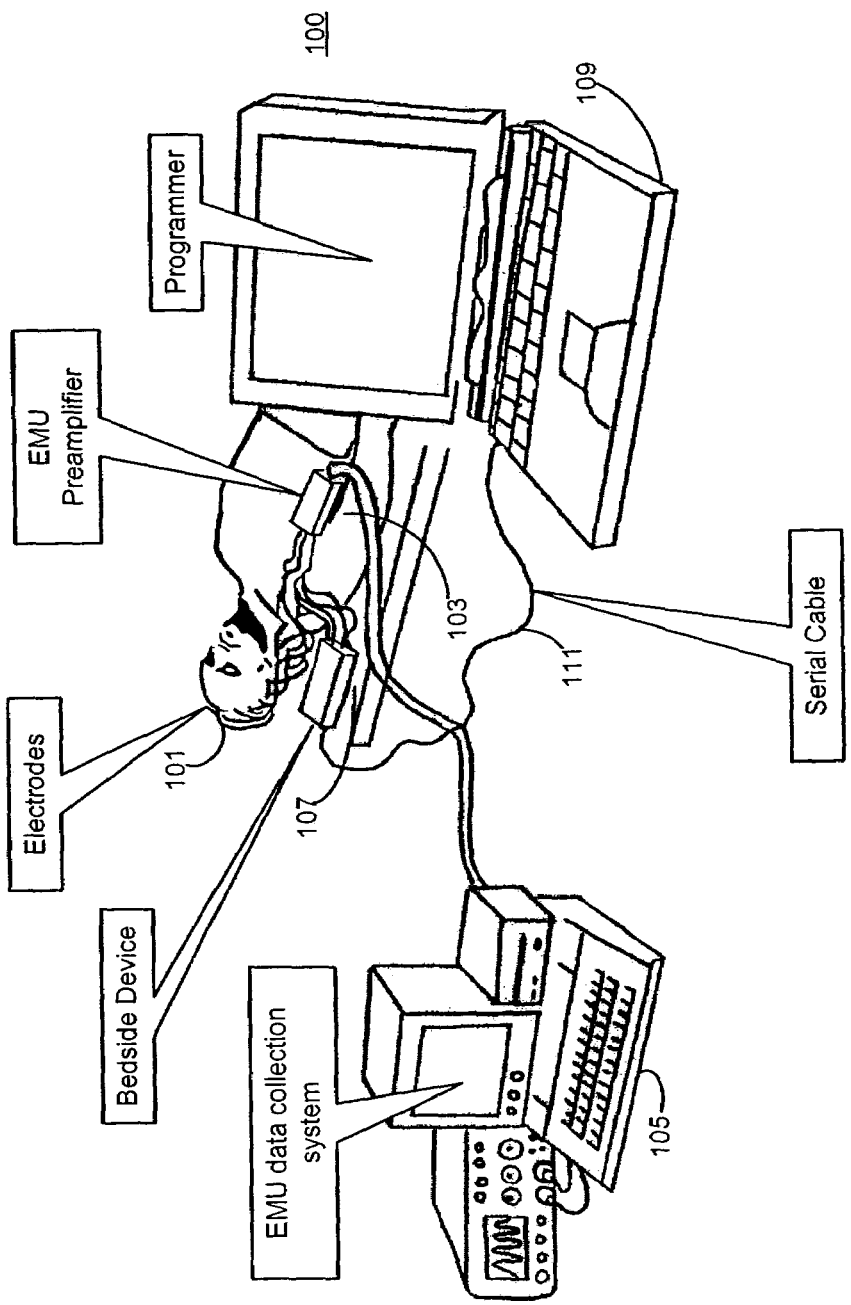
FIG. 1 shows one possible embodiment of an external system for treating a nervous system disorder.

The invention may be embodied in various forms to analyze and treat nervous system disorders, namely disorders of the central nervous system, peripheral nervous system, and mental health and psychiatric disorders. Such disorders include, for example without limitation, epilepsy, Parkinson's disease, essential tremor, dystonia, multiple sclerosis (MS), anxiety (such as general anxiety, panic, phobias, post traumatic stress disorder (PTSD), and obsessive compulsive disorder (OCD)), mood disorders (such as major depression, bipolar depression, and dysthymic disorder), sleep disorders (narcolepsy), obesity, tinnitus, stroke, traumatic brain injury, Alzheimers, and anorexia.

Moreover, the invention may utilize various treatment therapies for treating nervous system disorders. Treatment therapies can include any number of possibilities alone or in combination including, for example, electrical stimulation, magnetic stimulation, drug infusion, brain temperature control (e.g., cooling), and/or providing a sensory warning to the patient/clinician, as well as any combination thereof.

Each of these treatment modalities may be operated using closed-loop feedback control or using open-loop therapy. Such closed-loop feedback control techniques receive one or more neurological signals that carry information about a symptom or a condition of a nervous system disorder. Such neurological signals can include, for example, electrical signals (such as EEG, ECoG and/or EKG), chemical signals, biological signals (such as change in quantity of neurotransmitters), temperature signals, pressure signals (such as blood pressure, intracranial pressure or cardiac pressure), respiration signals, heart rate signals, pH-level signals, and/or peripheral nerve signals (cuff electrodes on a peripheral nerve). Such neurological signals may be recorded using one or more monitoring elements such as monitoring electrodes or sensors. For example, U.S. Pat. No. 6,227,203, assigned to Medtronic, Inc., provides examples of various types of sensors that may be used to detect a symptom or a condition or a nervous system disorder and responsively generate a neurological signal.

Even further, the invention may provide therapeutic treatment to neural tissue in any number of locations in the body including, for example, the brain (which includes the brain stem), the vagus nerve, the spinal cord, peripheral nerves, etc.

Disclosed herein are three general embodiments of the medical device system—an external system, a hybrid system, and an implanted system—however, the invention may be embodied in any number of configurations. The following embodiments may be described with the specific application of treating epilepsy by electrical stimulation of the brain and using closed-loop control monitoring of electrical activity in the brain. Other embodiments of the invention may use open-loop therapy, namely treatment therapy that can be provided independent of information obtained from the monitoring of brain activity. It will be appreciated, however, that other embodiments of the invention may treat other nervous system disorders, utilize other treatment therapies, optionally utilize closed-loop feedback control by receiving other forms of neurological signals, and/or deliver therapeutic treatment to neural tissue in other locations in the body. Moreover, the medical device system may simply collect data from one or more of the monitoring elements and provide that data to the patient or treating physician to further enhance management of the nervous system disorder.

EXTERNAL SYSTEM—FIG. 1 shows a system configuration of an external system 100. In an embodiment, the external system 100 is for use in the clinical environment although the external system 100 may also be used in other environments as well. As disclosed herein, the external system 100 provides electrical brain stimulation as the form of treatment therapy for purposes of treating seizures or epilepsy as the form of nervous system disorder. As discussed, however, it will be appreciated that system 100 may also be used to provide other treatment therapies at other locations of the body to treat other forms of nervous system disorders.

The external system 100 senses electrical brain signals from temporarily and/or permanently implanted brain electrodes 101, conditions the brain signals for processing, executes a detection algorithm (e.g., seizure algorithm 800 in FIG. 8) on the signals to determine the onset, presence, and/or intensity, duration, and spatial extent of neurological activity (e.g., seizure activity), and delivers electrical stimulation in response to selected event detections (e.g., seizure detections). Of course, in other embodiments, the external system 100 may be able to determine the onset, presence, and/or intensity of other neurological events. The components of the external system 100 may integrate with existing epilepsy monitoring unit (EMU) preamplifiers 103 and data collection systems to enable the simultaneous use of customary monitoring equipment 105.

The external system 100 incorporates a number of programmable parameters and features, some of which are discussed further herein. This affords the treating physician and investigators the necessary flexibility to explore a number of therapeutic paradigms. Data storage, display, and analysis capabilities are included in the system.

The external system 100 generally comprises a portable bedside device 107, a programmer 109, and a number of accessories. Bedside device 107 contains hardware and software to perform various functions including, for example, sensing electrical signals recorded by in-dwelling brain electrodes 101, conditioning the signals for further processing by the seizure detection algorithm, executing the seizure detection algorithm, and delivering treatment therapy such as electrical stimulation. Those skilled in the art will appreciate, however, that these functions of the bedside device 107 may be performed in other components of the external system 100.

Electrodes 101 are typically placed in the brain or on the surface of the brain or in the bone of the skull. Electrodes 101 could be placed between the surface of the skull and the scalp, within the scalp, over the scalp, or outside the body on the skin surface. Electrodes 101 are coupled to the bedside device 107 through input jacks compatible with standard electrode extensions and connectors. Electrode output jacks on the box provide a means for passing raw brain signals to existing EMU equipment. A serial port supports the real-time transfer of data between the programmer 109 and the bedside device 107. As discussed herein, electrodes 101 may take any number of forms including, but not limited to, temporary subdural grid and strip electrodes, temporary depth electrodes, deep brain stimulation (DBS) electrode systems, and/or a combination of several different electrode types. Although in an embodiment, the external system 100 utilizes eight electrodes, it will be appreciated that greater or fewer electrodes may be utilized. Moreover, other forms of communication may also be utilized between the various components including wireless, infrared, radio frequency (RF), and/or computer network (e.g., LAN, WAN, Internet).

The external system 100 utilizes a programmer 109, which in the embodiment is a commercially available personal computer and an operating system configured with custom external system application software. Those skilled in the art will appreciate that any general-purpose computing device may be used including, but not limited to, a hand-held device. Other communication techniques, of course, may also be utilized including a telemetry device. The programmer 109 may display in real-time the brain signals being processed by the system, the corresponding detection criteria for automated seizure detection, and other pertinent system and session information. All programmable system parameters, including electrode designation, algorithm parameters, and stimulation output parameters, may be adjusted through the programmer 109. Investigators may also use the programmer 109 to perform secondary functions, such as off-line algorithm analysis and adaptation.

Accessories for the external system 100 include a serial cable 111 for connecting bedside device 107 to programmer 109, a medical grade 6 Vdc power supply for primary power to bedside device 107, a supply of batteries for bedside device 107, and an event marker junction box (not shown). The event marker junction box allows the patient, or anyone else, to manually record the onset of an event of significance, such as a seizure (an ictal event). Data may be collected during the event and sent simultaneously to the bedside device 107 and the EMU equipment. The event marker junction box allows the patient event marker signal to be input to both the EMU equipment and the bedside device 107 simultaneously. In the embodiment, bedside device 107 is coupled to the event marker junction box and to an event input of the EMU equipment. The ability to simultaneously input the event marker in the EMU equipment and the bedside device 107 also serves to synchronize events recorded/stored in both the EMU equipment and the bedside device 107. With a variation of the embodiment, a time drift may be determined. The time drift is indicative of a time difference of the bedside device 107 with respect to the EMU equipment.

Temporary diagnostic electrodes, manufactured by Adtech, Radionics, and PMT Corp. among others, may be used for recording brain signals to aid in the identification of the areas responsible for seizure generation. Electrodes 101 are typically placed intracranially, on the surface of the brain (subdural grids and strips) or within brain tissue (depth electrodes), near areas suspected of being epileptogenic. ECoG signals from these electrodes 101 are recorded on external EEG monitoring equipment (Grass/Telefactor, Nicolet Biomedical, Bio-logic, and others) and evaluated by the physician to determine the zone(s) of epileptogenesis.

In addition to monitoring, electrodes 101 may conduct stimulus pulses generated by a stimulator to map the functional areas of the brain underlying electrode 101. In this manner, the physician is able to determine the risks and benefits associated with a possible surgical approach to treat the patient's epilepsy.

The external system 100 may also support deep brain stimulation as a treatment for intractable epilepsy. DBS leads may be placed within structures of the brain (e.g., thalamic nuclei, subthalamus, temporal lobe, etc.) to enable the continuous or intermittent delivery of electrical stimulation to structures that may have a network or local effect on areas of epileptogenesis. ECoG recordings may also be obtained from the DBS leads.

When the system 100 is set up with the EMU, the externalized ends of the implanted electrodes 101 will connect directly to the bedside device 107. The raw signals collected by the electrodes 101 connected to bedside device 107 are processed by the external system 100 and passed to existing EMU preamplifier 103 and into EMU data collection system 105. Additional electrode connections may occur directly between the patient and existing EMU preamplifier 103 and data collection system 105, bypassing the external system 100, to enable recording from a greater number of electrode contacts than used by bedside device 107. By means of a serial cable 111, the bedside device 107 interfaces with the programmer 109 through which system programming, data display, and real-time and/or retrospective analysis may take place.

Figure 2:
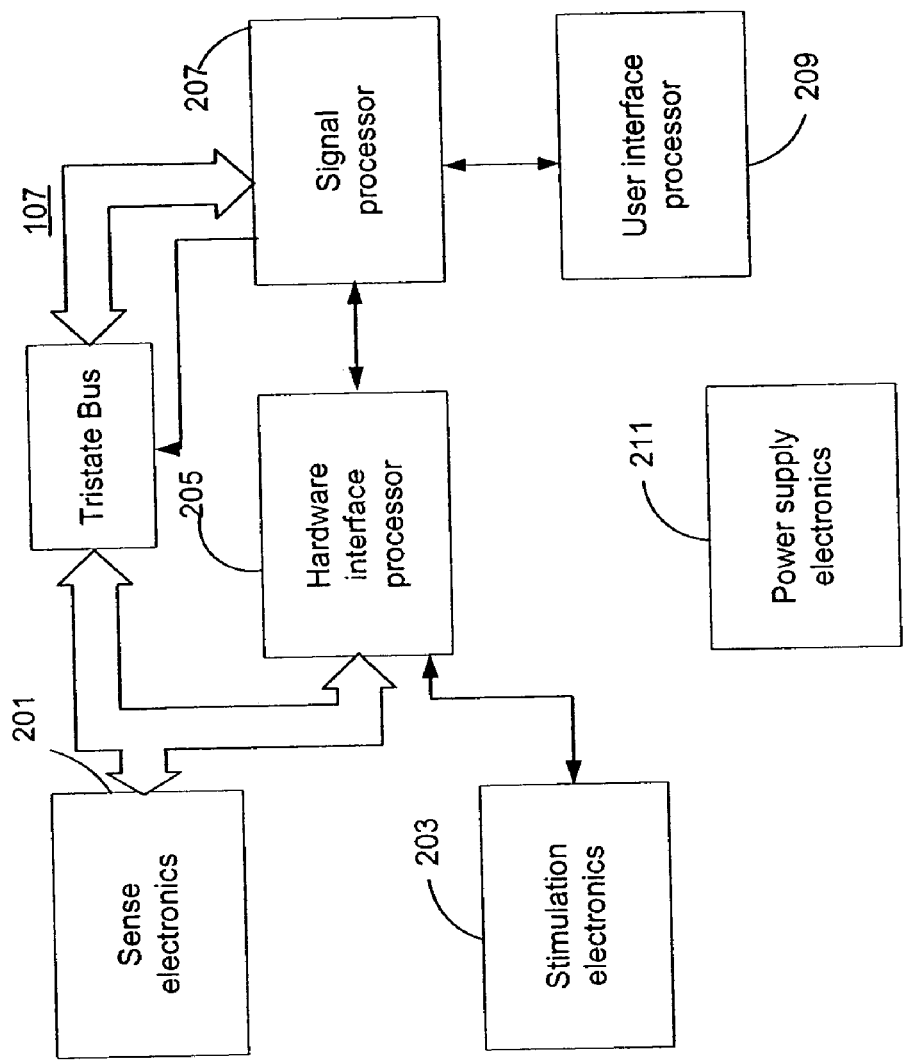
FIG. 2 shows a configuration of a bedside device that is associated with the external control system of FIG. 1.

FIG. 2 is a schematic block diagram depicting the bedside device 107, which is a component of the external system 100. The bedside device 107 comprises a sense electronics module 201 for processing (i.e., amplifying and digitizing) the sensed neurological signal, a stimulation electronics module 203 for providing treatment therapy, a hardware interface processor 205 for controlling the sense and stimulation electronics modules and passing the digitized EEG data to a signal processor 207 (which performs detection algorithm and control system timing and operation), a user interface processor 209 for controlling serial data to and from the signal processor 207 and the programmer 109, and a power supply 211.

Figure 3:
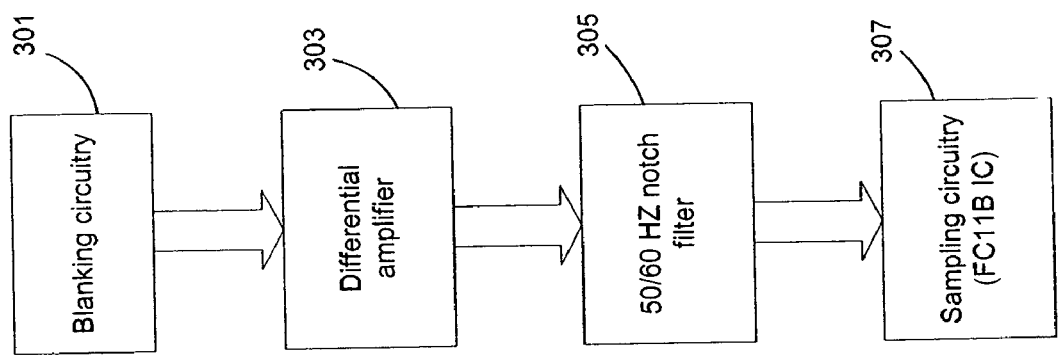
FIG. 3 shows a configuration of a sense electronics module that is associated with the bedside device of FIG. 2.

FIG. 3 is a schematic block diagram depicting the sense electronics module 201 associated with the bedside device 107. Sense electronics module 201 processes EEG signals from the electrodes 101 so that the EEG signals can be further processed by the signal processor 207. A blanking circuitry 301 comprises optically coupled relays. Blanking circuitry 301 provides independent blanking of any channel electronics (e.g., an amplifier) that is associated with an electrode. Blanking circuitry 301 disconnects the channel received from the electrode when the electrode is being stimulated. A differential amplifier 303 provides buffering and isolation from electronics associated with other channels by having a high common mode rejection. A notch filter 305 removes residual 50 or 60 Hz noise signal component that may be attributable to powering the external system 100 from alternating current (AC). A sampling circuitry 307 converts an analog signal associated with each channel into a digital signal with an analog to digital converter. In the embodiment, sampling circuitry 307 provides eight bit resolution with a 250 Hz sampling rate, an adjustable gain, and adjustable analog filter corners. Those skilled in the art will appreciate that the digital precision and sampling rates may be increased or decreased according to the particular application or sensed signal.

Figure 4:
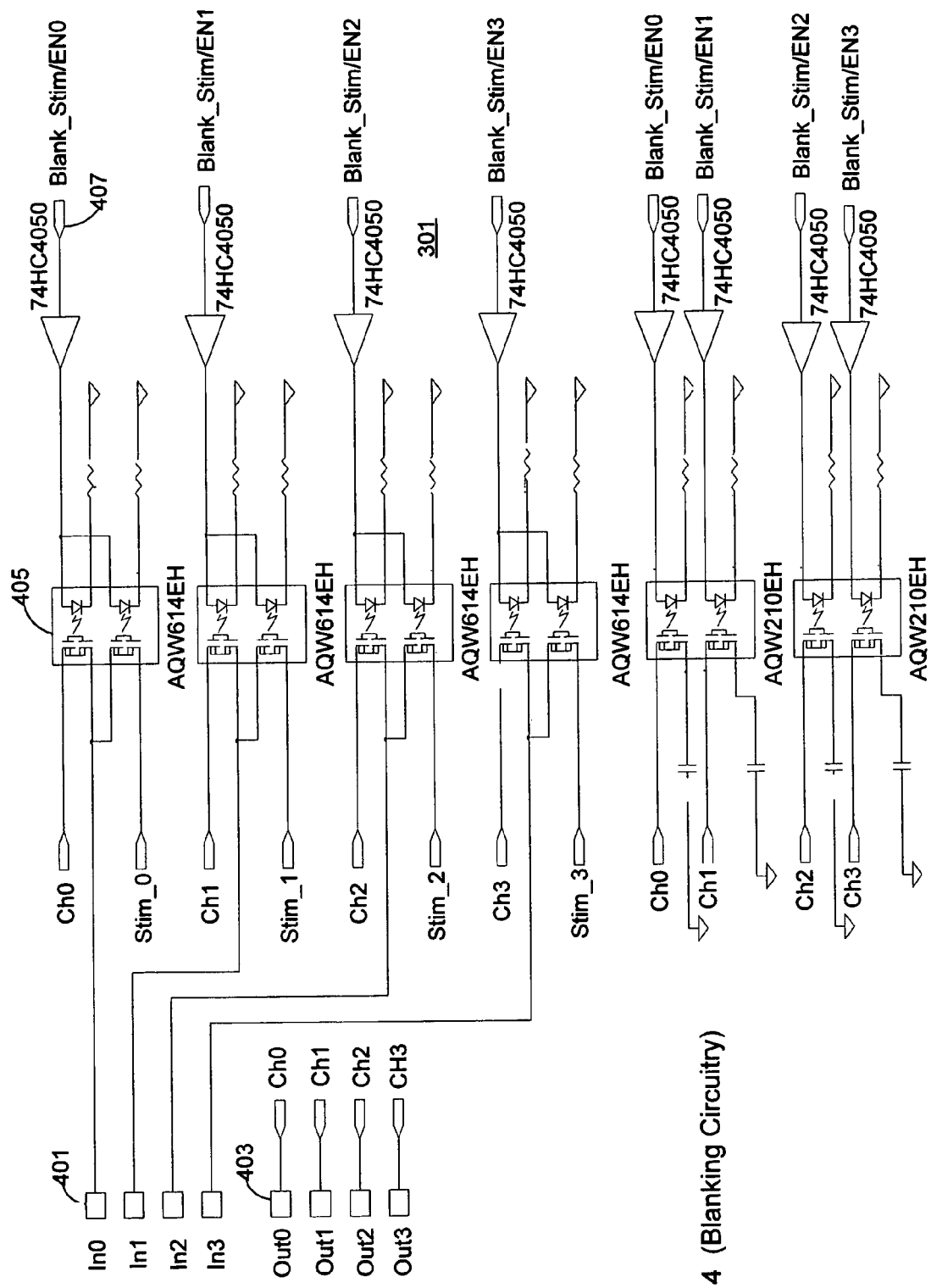
FIG. 4 shows an embodiment of blanking circuitry that is associated with the external system of FIG. 1.

FIG. 4 is a schematic block diagram depicting an embodiment of blanking circuitry associated with the external control system 100. An optically coupled relay 405 is associated with an input 401 and an output 403. Blanking circuitry 301 controls relay 405 through control signal 407 so that output 403 is isolated from input 401 when the associated electrode is being stimulated. The circuit also ensures that the amplifier input during this time is not floating to prevent drifts in the voltages recorded by the system.

Figure 5:
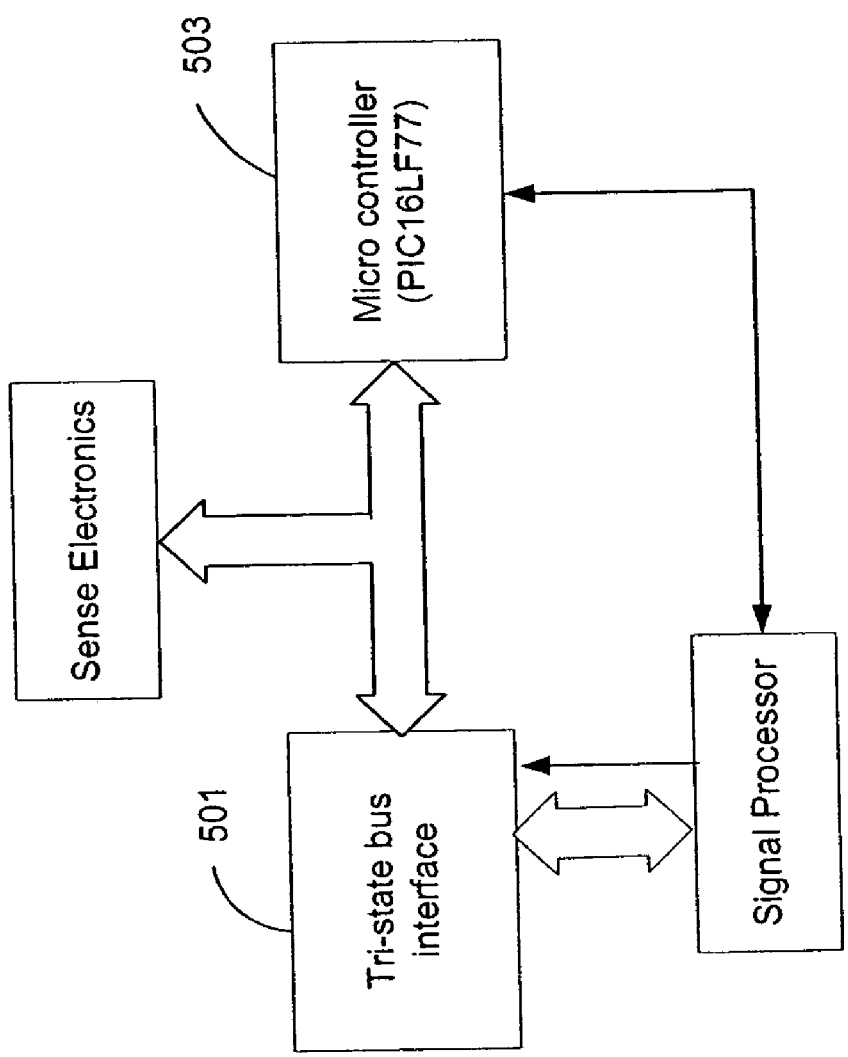
FIG. 5 shows a hardware interface that is associated with the bedside device of FIG. 2.

FIG. 5 is a schematic block diagram depicting the hardware interface processor 205 associated with the bedside device 107. Hardware interface processor 205 comprises a micro controller 503 to control blanking circuitry 301, sense electronics module 201, and stimulation electronics module 203. It also notifies signal processor 207 when data is available for further processing.

Figure 6:
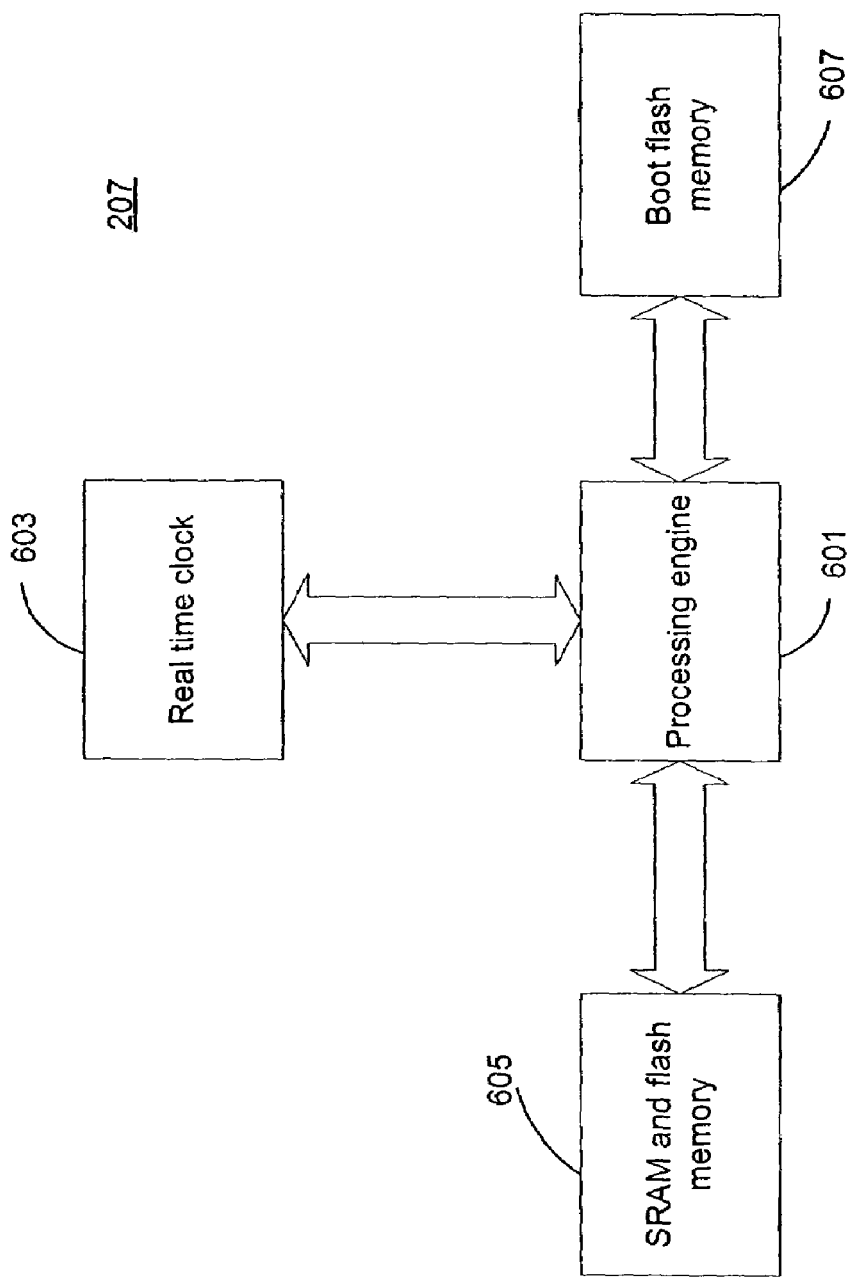
FIG. 6 shows a signal processor that is associated with the bedside device of FIG. 2.

FIG. 6 is a schematic block diagram depicting the signal processor 207 associated with the bedside device 107. Signal processor 207 comprises a processing engine 601 (e.g., Analog Devices ADSP2189M), an SRAM and flash memory 605, which is used for loop recording, a real time clock 603, which is used for associating a time with loop recording, and a boot flash memory 607, which loads a program on powering up signal processor 207.

Figure 7:
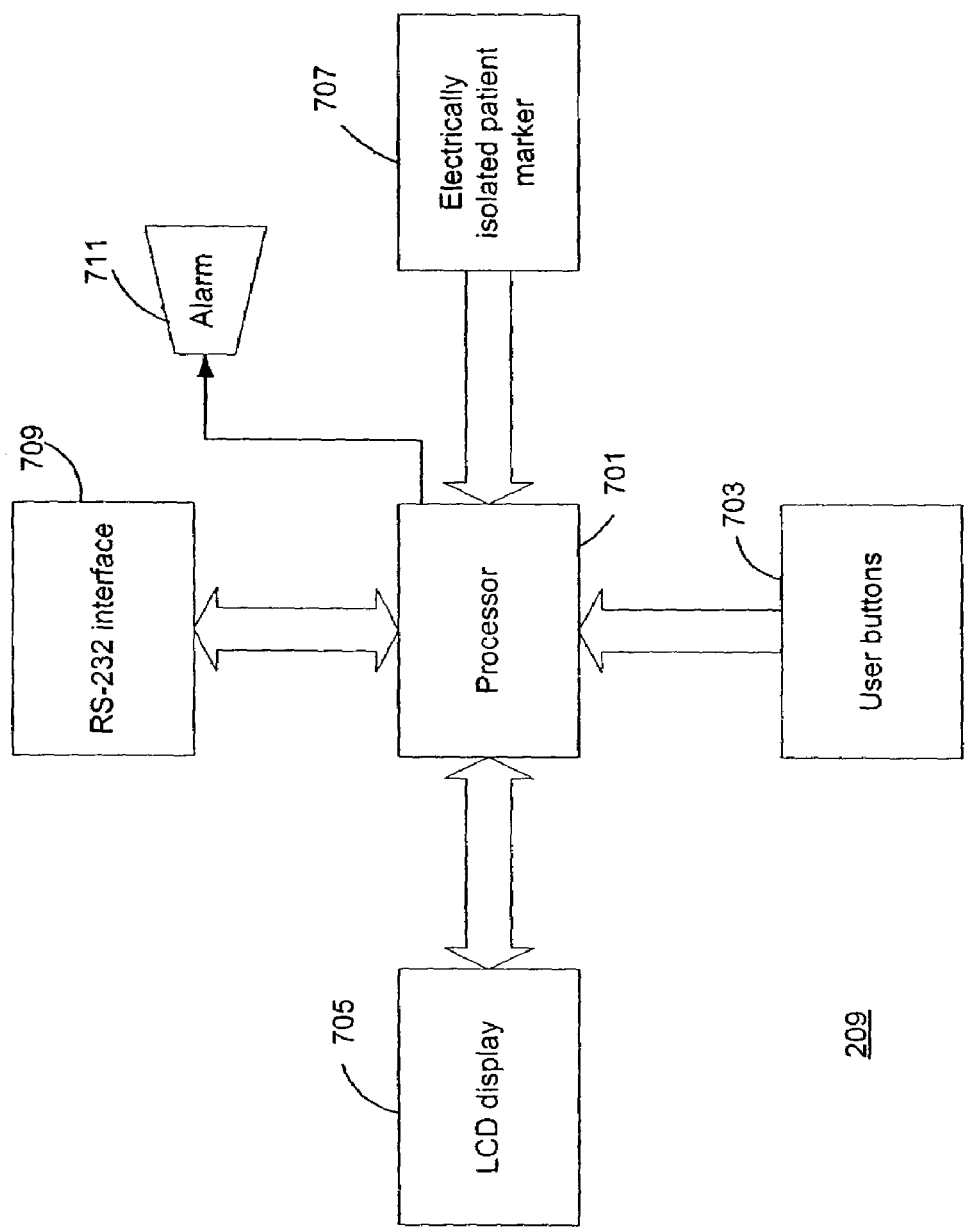
FIG. 7 shows a user interface processor that is associated with the bedside device of FIG. 2.

FIG. 7 is a schematic block diagram depicting the user interface processor (UIP) 209 associated with the bedside device 107. A processor 701 receives data and commands through user buttons 703. Processor 701 may be a single device or may consist of multiple computing elements such as a Digital Signal Processor (DSP). The UIP 209 may provide a RS-232 interface 709 between the programmer 109 and the processor 701. Moreover, a component of the UIP 209 and processor 701 may communicate with each other to convey other information (such as button press data from user buttons 703 to the processor 701, and icon status data from the processor 701 to an LCD display 705). Processors (e.g., DSPs) associated with processor 701 may also utilize analog circuitry. Additionally, RS-232 interface 709 enables information to be sent to processor 701 from the user. Processor 701 responds to the data and commands from the user by displaying and updating a menu display on the LCD display 705. The patient may input a marker, signifying an event such as a seizure, through isolated patient marker 707. An alarm 711 may alert the user or the patient about an event such as a detected or predicted seizure.

As discussed, the external system may be implemented with the specific application of treating epilepsy by electrical stimulation of the brain using, as one of the possible options, closed-loop control based on monitoring of electrical activity in the brain. In such an embodiment, a seizure detection algorithm may be utilized to monitor the electrical brain activity and predict whether a seizure onset is about to occur or detect its onset. In accordance with an embodiment, the seizure detection algorithm is that disclosed in U.S. Pat. No. 5,995,868 (entitled "System for the Prediction, Warning, Prevention, or Control of Changes in Activity States in the Brain of a Subject"). Other embodiments may utilize variations of the seizure detection algorithm or may use other detection algorithms for detecting seizures and/or other nervous system disorders. Moreover, the detection algorithm may be adaptable. Discussed below is an overview of a preferred embodiment of the seizure detection algorithm followed by an example of how the algorithm may be adaptable.

Figure 8:
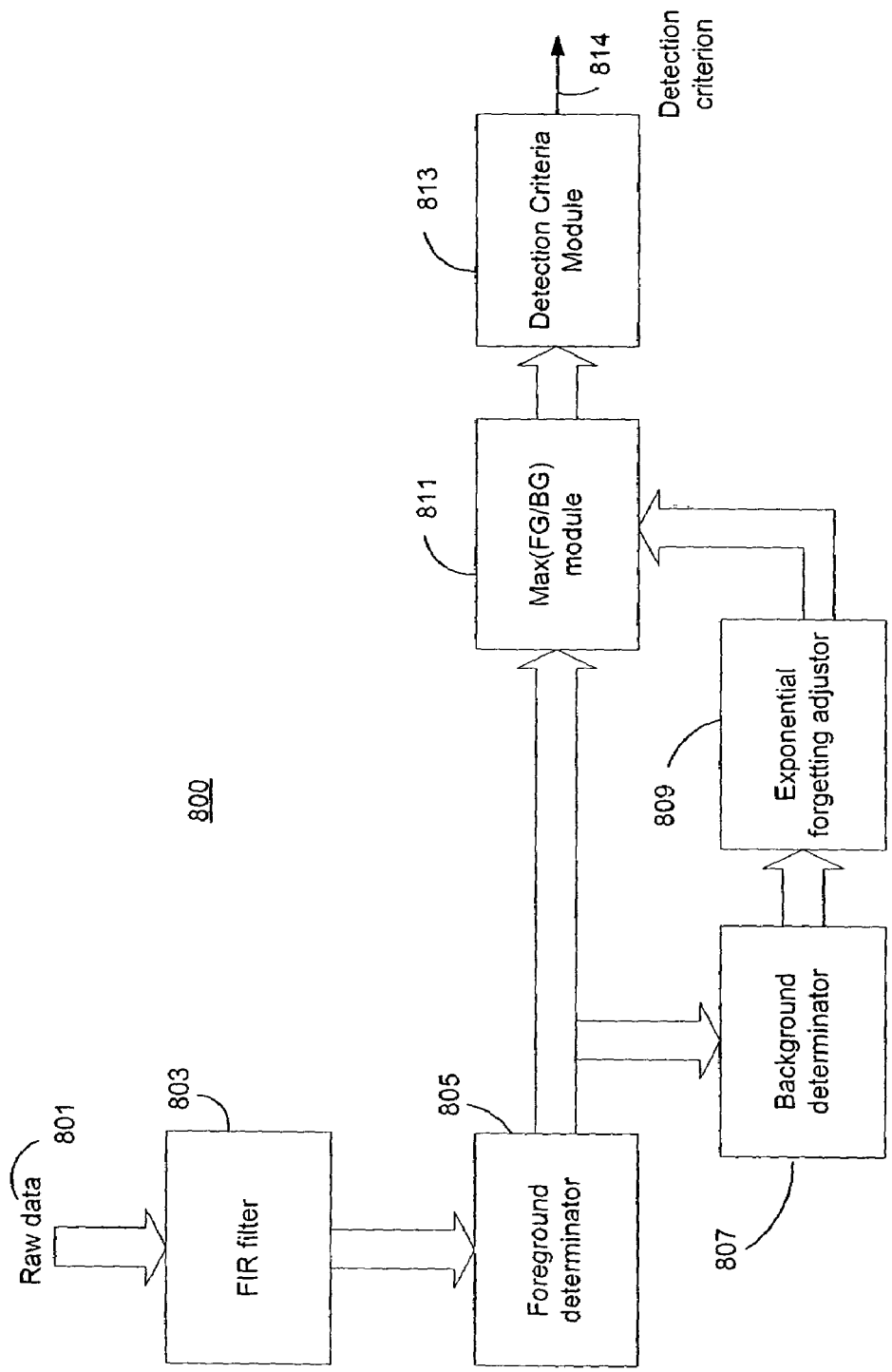
FIG. 8 is a functional diagram of one embodiment of a seizure detection algorithm for use with a medical device system for treatment of a seizure.

FIG. 8 shows a functional diagram of an example of a seizure detection algorithm 800 that may be used. Generally, the seizure detection algorithm 800 is capable of detecting brain activity changes based on the spectral characteristics, intensity (ratio), spread, and duration of an electrical (EEG, ECoG, and/or EKG) signal 801 that is obtained from a set of electrodes. In the embodiment of external system 100, eight ECoG channels may be supported, although other embodiments may support a different number of channels. The analog EEG or ECoG data from the electrodes 101 are transformed to digital data with an A to D converter in the bedside device 107. In the hybrid system 1000, the A to D converter may be in the implantable device 953. A digital filter such as a finite impulse response (FIR) filter 803 is configured to estimate the power spectrum density characteristics of a set of electrical brain signals. A foreground determinator 805 associates a foreground value of the signals with a moving foreground interval of a predetermined time length (e.g., 2-seconds), which may be programmable. In the embodiment, foreground determinator 805 squares the value of each sample in the foreground interval and selects the median value. A background determinator 807 associates a background value with a moving background interval of predetermined time length (e.g., 30 minutes), which again may be programmable. At any point in time, the current foreground and background values are computed, respectively, from the foreground and background intervals that immediately precede that time point. Background determinator 807 squares the value of each sample in the background interval and selects the median value. The seizure detection algorithm 800 then processes the results of background determinator 807 through an "exponential forgetting" adjustor 809 that combines the results with previous results from background determinator 807 to produce a exponentially-smoothed background value. A module 811 then divides the foreground value by the exponentially-smoothed background value to determine a ratio for each signal from each electrode in a selected electrode group. Module 811 also determines the largest ratio from the group of electrodes. The value of the largest ratio is then fed into a detection criterion module 813, which analyzes the sequence of largest ratios to determine when an event is detected. Output 814 from algorithm 800 includes notification that an event has occurred ("detection") as well as variables quantifying the event (e.g., ratio, extent of spread, and duration from all electrodes).

As discussed, the external system 100 may take other forms including, for example, a hybrid control system and an implantable control system. The functionalities described herein may be performed by any of these embodiments, in which some of the functionalities may be associated with different components of the various embodiments.

Figure 9:
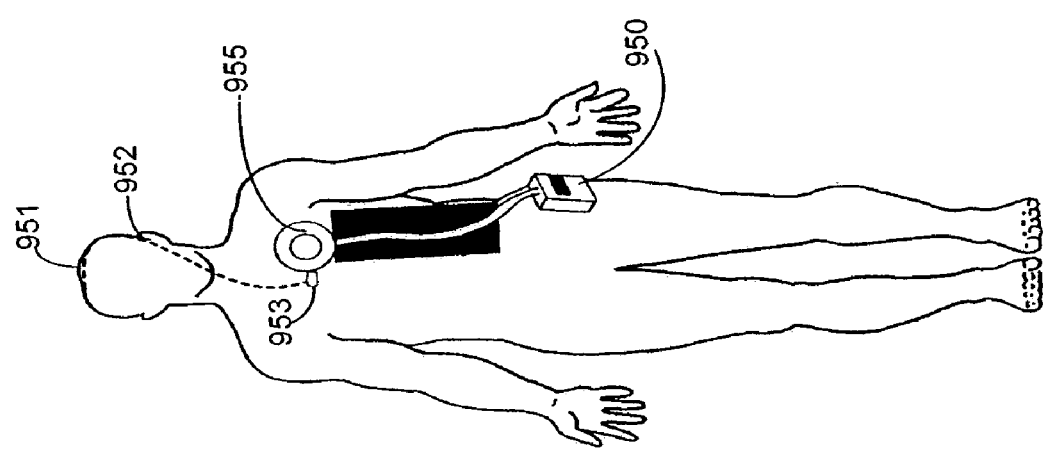
FIG. 9 shows one possible embodiment of a hybrid system for treating a nervous system disorder.

HYBRID SYSTEM—FIG. 9 shows an embodiment of a hybrid system 1000 for treatment of a nervous system disorder in accordance with one embodiment of the invention. As discussed, although the hybrid system 1000 is discussed in the context of providing brain stimulation for treating epilepsy, it will be appreciated that the hybrid system 1000 may also be used to provide other treatment therapies at other locations of the body to treat other forms of nervous system disorders.

Referring still to FIG. 9, leads 951 are coupled at a distal end to electrodes that sense brain activity of the patient and deliver electrical stimulation to the patient. At a proximal end, leads 951 are coupled to extension wire system 952 that in turn connects to an implantable device 953. The connection between leads 951 and extension wire system 952 typically occurs under the scalp on top of the cranium at a convenient location such as behind and above the ear. The distal connector of extension wire system 952 is designed to accommodate the various options for leads 951 which might be selected by the surgeon to record and/or stimulate from deep within the brain, on the surface of the cortex or from electrodes just protruding through the skull or on the surface of the skull. Extension wire system 952 is passed just under the skin along the lateral aspect of the neck to connect with implantable device 953. Leads 951 typically last at least as long as extension wire 952. Extension wire 952 is made of materials that allow it to withstand considerable stress/forces caused by neck movement. The implantable device 953 conditions signals, samples the signals, and delivers electrical stimulation through the electrodes 951. An antenna 955 supports telemetric communications between the implantable device 953 and an external device 950. The external device 950, which may be an external wearable digital signal processing unit, receives sampled signals from the implantable device 953, detects seizures, and sends signals to the implantable device 953 to initiate stimulation therapy.

Figure 10:
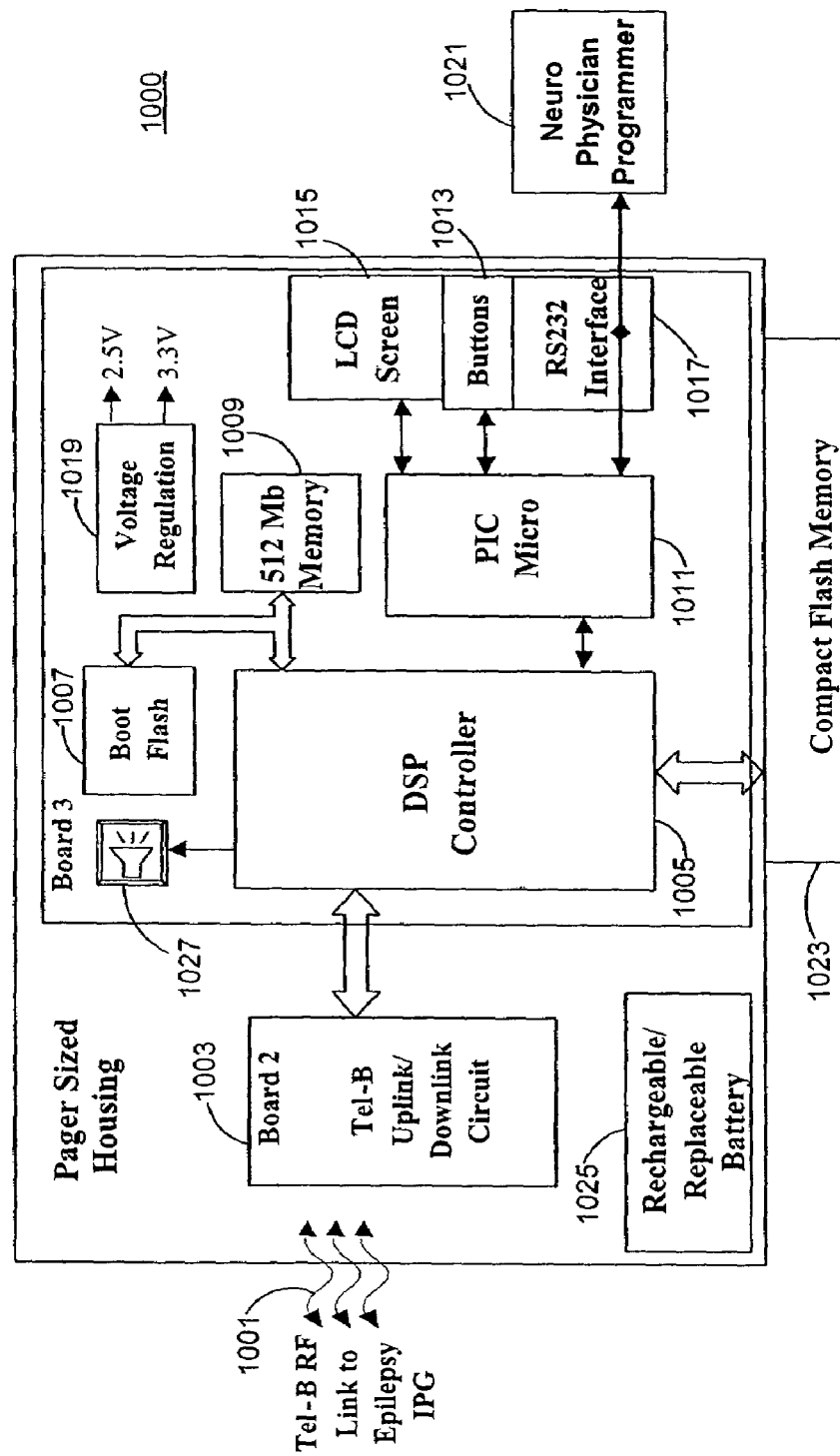
FIG. 10 is a schematic block diagram of an external component of a hybrid system for treatment of a nervous system disorder.

FIG. 10 is a schematic block diagram of the external device 950 for the hybrid control system of FIG. 9. The external device 950 communicates (continuously or intermittently) with the implantable device 953 over a telemetry link 1001 through an uplink/downlink circuit 1003 or through a cabling arrangement. The external device 950 may interface with a programmer 1021 (such as programmer 209) through RS232 interface 1017. The programmer 1021 may be a physician programmer, a patient programmer, or any general-purpose computing device having software for interfacing with a medical device system.

An apparatus 1000 (e.g., the external device 950) is powered by a rechargeable/replaceable battery 1025 and is voltage regulated by a voltage regulation circuit 1019. A DSP controller 1005 processes neurological data from implantable device 953 and records/stores processed data in a boot flash memory 1007 or in a compact flash memory 1023, which extends the recording capability of memory 1007. The apparatus 1000 may be instructed by a user through buttons 1013. The corresponding inputted information is received by a peripheral interface control (PIC) microprocessor 1011 through a RS232 interface 1017. The user may instruct the DSP controller 1005 to process, store, and retrieve neurological data through PIC microprocessor 1005. Also, the user may obtain information (e.g., status and selected processed data) through an LCD screen 1015.

Figure 11:
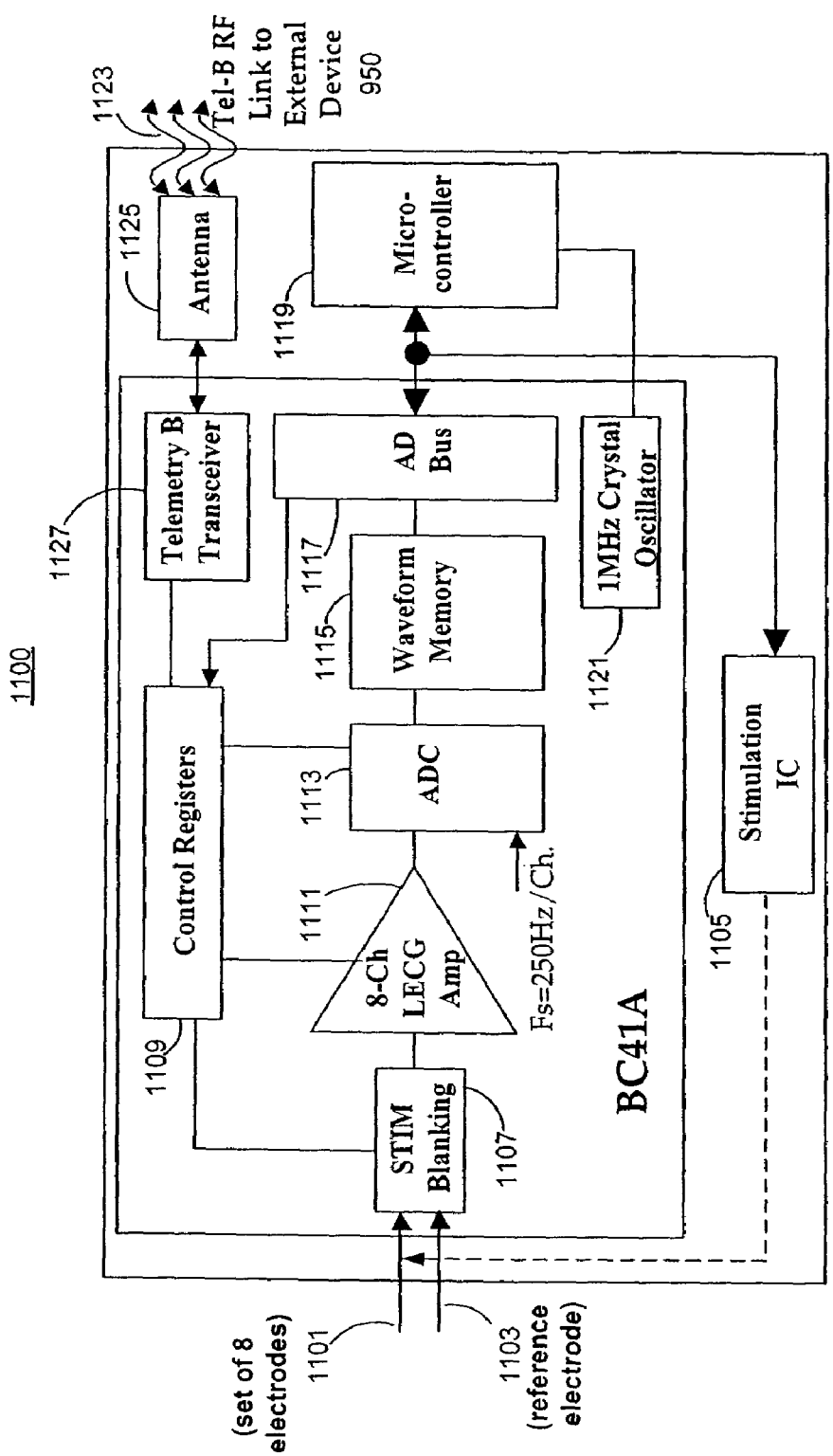
FIG. 11 is a schematic block diagram of the implantable component of a hybrid system for treatment of a nervous system disorder.

FIG. 11 is a schematic block diagram of the implantable device 953 for the hybrid control system of FIG. 9. An apparatus 1100 (e.g., the implantable device 953) is implanted in conjunction with a set of electrodes 1101. (In the exemplary embodiment shown in FIG. 11, the set of electrodes 1101 comprises eight electrodes.) A reference electrode 1103 is another electrode that is not included in the set of electrodes 1101 and that is not typically involved with the neurological activity as the set of electrodes 1101. The apparatus 1100 communicates with the external device 1000 through a telemetry transceiver 1127, an antenna 1125, and a telemetry link 1023. The apparatus 1000 (e.g., the external device 950) may collect data from the apparatus 1100 by placing a patch antenna 955 on the patient's body over the implantable device 953 to thereby communicate with antenna 1125 of the apparatus 1100.

Each electrode of the set of electrodes 1101 may either receive a neurological signal or may stimulate surrounding tissue. Stimulation of any of the electrodes contained in the electrode set 1101 is generated by a stimulation IC 1105, as instructed by a microprocessor 1119. When stimulation is generated through an electrode, the electrode is blanked by a blanking circuit 1107 so that a neurological signal is not received by channel electronics (e.g., amplifier 1111). When microcontroller 1119 determines that a channel shall be able to receive a neurological signal, an analog to digital converter (ADC) 1113 samples the neurological signal at a desired rate (e.g., 250 times per second). The digitized neurological signal may be stored in a waveform memory 1115 so that the neurological data may be retrieved by the apparatus 1000 when instructed.

Figure 12:
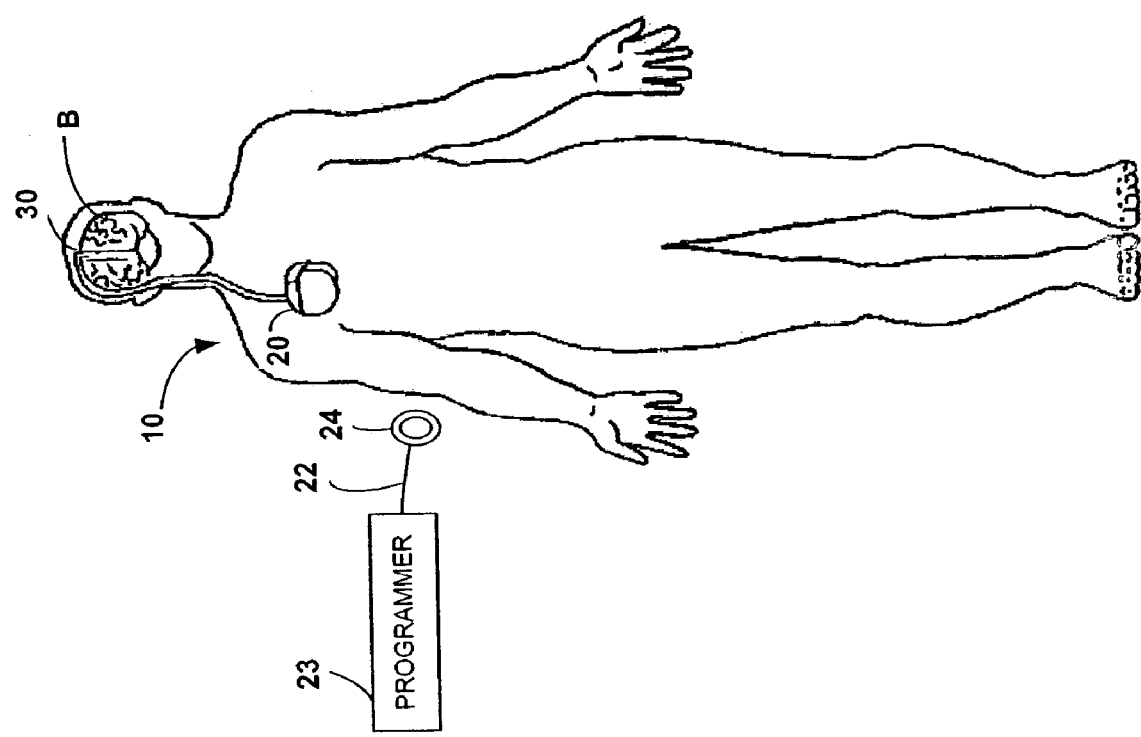
FIG. 12 shows one possible embodiment an implantable system for treating a nervous system disorder.

IMPLANTED SYSTEM—FIG. 12 shows an embodiment of an implanted system 10 for treatment of a nervous system disorder in accordance with another embodiment of the invention. As discussed, although the implanted system 10 is discussed in the context of providing brain stimulation, it will be appreciated that the implanted system 10 may also be used to provide other treatment therapies at the brain or head or at other locations of the body. The implanted system 10 generally includes an implanted device 20 coupled to one or more therapy delivery elements 30. The therapy delivery elements 30, of course, may also serve as monitoring elements to receive a neurological signal. The implanted device 20 may continuously or intermittently communicate with an external programmer 23 (e.g., patient or physician programmer) via telemetry using, for example, radio-frequency signals. In this embodiment, each of the features and functionalities discussed herein are provided by the implanted device 20.

Those skilled in the art will appreciate that the medical device systems described above may take any number of forms from being fully implanted to being mostly external and can provide treatment therapy to neural tissue in any number of locations in the body. For example, the medical device systems described herein may be utilized to provide vagal nerve stimulation, for example, as disclosed in U.S. Pat. No. 6,341,236 (Osorio, et al.). In addition, the treatment therapy being provided by the medical device systems may vary and can include, for example, electrical stimulation, magnetic stimulation, drug infusion (discussed below), and/ or brain temperature control (e.g., cooling). Moreover, it will be appreciated that the medical device systems may be utilized to analyze and treat any number of nervous system disorders. For example, various U.S. Patents assigned to Medtronic provide example of nervous system disorders that can be treated. In the event that closed-loop feedback control is provided, the medical device system can be configured to receive any number of neurological signals that carry information about a symptom or a condition or a nervous system disorder. Such signals may be provided using one or more monitoring elements such as monitoring electrodes or sensors. For example, U.S. Pat. No. 6,227,203, assigned to Medtronic, Inc., provides examples of various types of sensors that may be used to detect a symptom or a condition or a nervous system disorder and responsively generate a neurological signal and is incorporated herein in its entirety.

Figure 13:
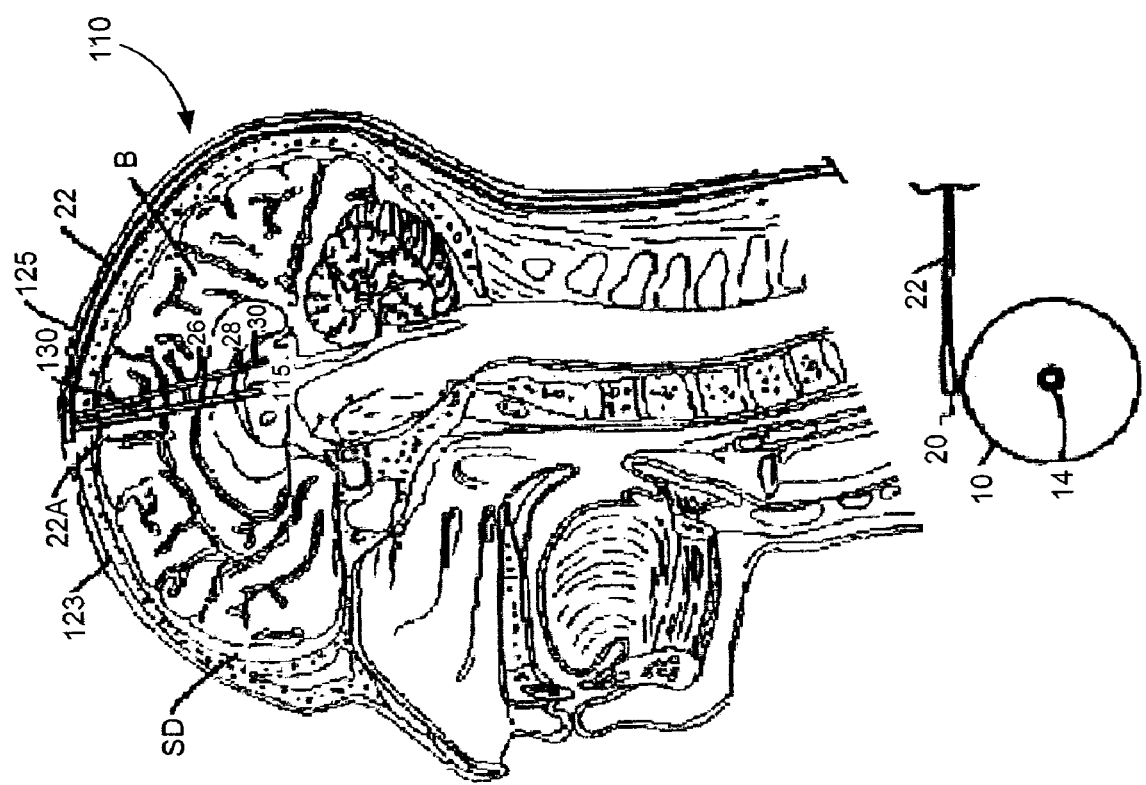
FIG. 13 shows an example of a medical device system for infusing drug as the treatment therapy for treating nervous system disorders.

As an example to illustrate other embodiments of treatment therapies, FIG. 13 shows a medical device system 110 that may be implanted below the skin of a patient for delivery of drug to a patient as the form of treatment therapy. Device 10 has a port 14 into which a needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B), although any location in the body may be utilized. As it relates to the delivery of drug, device 10 may take a form of the like-numbered device shown in U.S. Pat. No. 4,692,147 (Duggan), assigned to Medtronic, Inc., Minneapolis, Minn. and is incorporated herein in its entirety. The device 10 may be augmented to provide the various functionalities of the present invention described herein.

Discussed herein are various features and functionalities that one or more of the above-described medical device systems may incorporate. Where applicable and although not required, these features and functionalities will be described in the general context of computer-executable instructions, such as program modules. Generally, program modules include routines, programs, objects, scripts, components, data structures, and the like that perform particular tasks or implement particular abstract data types. Moreover, these features and functionalities may reside in any number of locations within the medical device system including either one of the implanted components and/or one of the external components.

Relaying Module For Treatment of Nervous System Disorders

In the hybrid system 1000 and the implanted system 10 embodiment, greater telemetric portability may be achieved between the implanted component and the external component by providing a relaying module.

Figure 14:
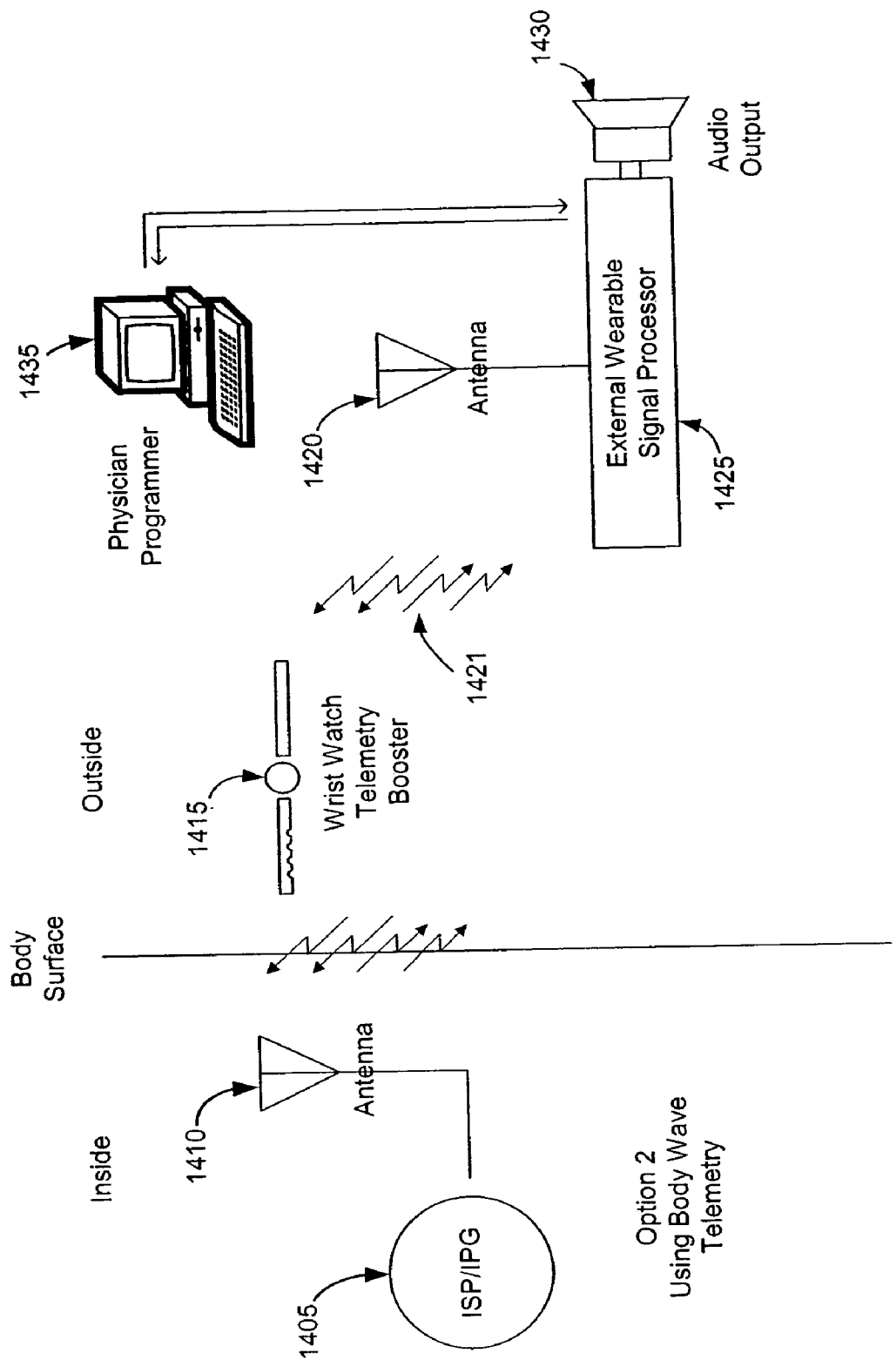
FIG. 14 is a schematic diagram of a relaying module worn on a patient's wrist for use with a medical device system having implanted components.

FIG. 14 discloses one embodiment of such a relaying module in the form of a device that is worn, for example, on the patient's wrist. In such an arrangement, the implanted component 1405 of the medical device system communicates with the relaying module 1415 via telemetry antenna 1410. Similarly, the external component communicates with the relaying module 1415 via antenna 1420. In the embodiment, a telemetry link 1421 between relaying module 1415 and antenna 1420 comprises a 3 MHz body wave telemetry link. To avoid interference, the relaying module 1415 may communicate with the external and implanted components using differing communication schemes. In some embodiments, the reverse direction and the forward direction of telemetry link 1421 may be associated with different frequency spectra. The relaying module 1415 thereby provides a greater range of communications between components of medical device system. For example, in the embodiment of the implanted system 10, the external programmer 23 may communicate with the implanted device 20 from a more remote location. The external programmer 23 may be across the room and still be in communication via the relaying module 1415. Similarly, in the embodiment of the hybrid system 1000, the external device 950 may be located further away than being worn by the patient. With the telemetry booster stage, the use of hybrid system 1000 is more convenient to the patient in particular at night while sleeping or when taking a shower, eliminating the need for the external device 950 to be worn on the body.

Synchronized and/or Calibrated Clocks Providing Treatment Therapy to a Patient

Obtaining, processing, storing and using information that evolves over time and using multiple devices requires adequate time synchronization between different clocks used by the respective devices for meaningful interpretation and use of this information for control or other purposes. With a medical device system, it may be important that different clocks, in which at least one of the clocks is associated with the medical device system, be synchronized. For example, proper synchronization is required between an epilepsy monitoring system clock used to timestamp the onset time of a clinical seizure and that of a medical device used to record, analyze and timestamp the subject's brain waves. Knowing whether particular EEG signal changes precede or follow behavioral changes (and by how long) is important in assessing whether the electrodes from which the signal was obtained is at or near the seizure focus. The importance of clock synchronization is further exemplified in the discussion of screening below.

Any one of the above-described medical device systems may be configured to provide synchronization and calibration of all system clocks. (Moreover, the embodiment may support configurations in which one or more of the clocks are associated with an entity that is different from a medical device system.) Where an embodiment of the medical device system comprises more than one system clock, it may become desirable to ensure that the clocks are synchronized with each other. For example, in the embodiment of the external system 100, the system comprises monitoring equipment 105, bedside device 107, and programmer 109, in which each component may have separate clocks. In order to coordinate the clocks, bedside device 107 provides a synchronization and calibration process that enables the plurality of clocks to be aligned within a desired accuracy. It will be appreciated, however, that the synchronization process may be implemented within any other component.

Figure 15:
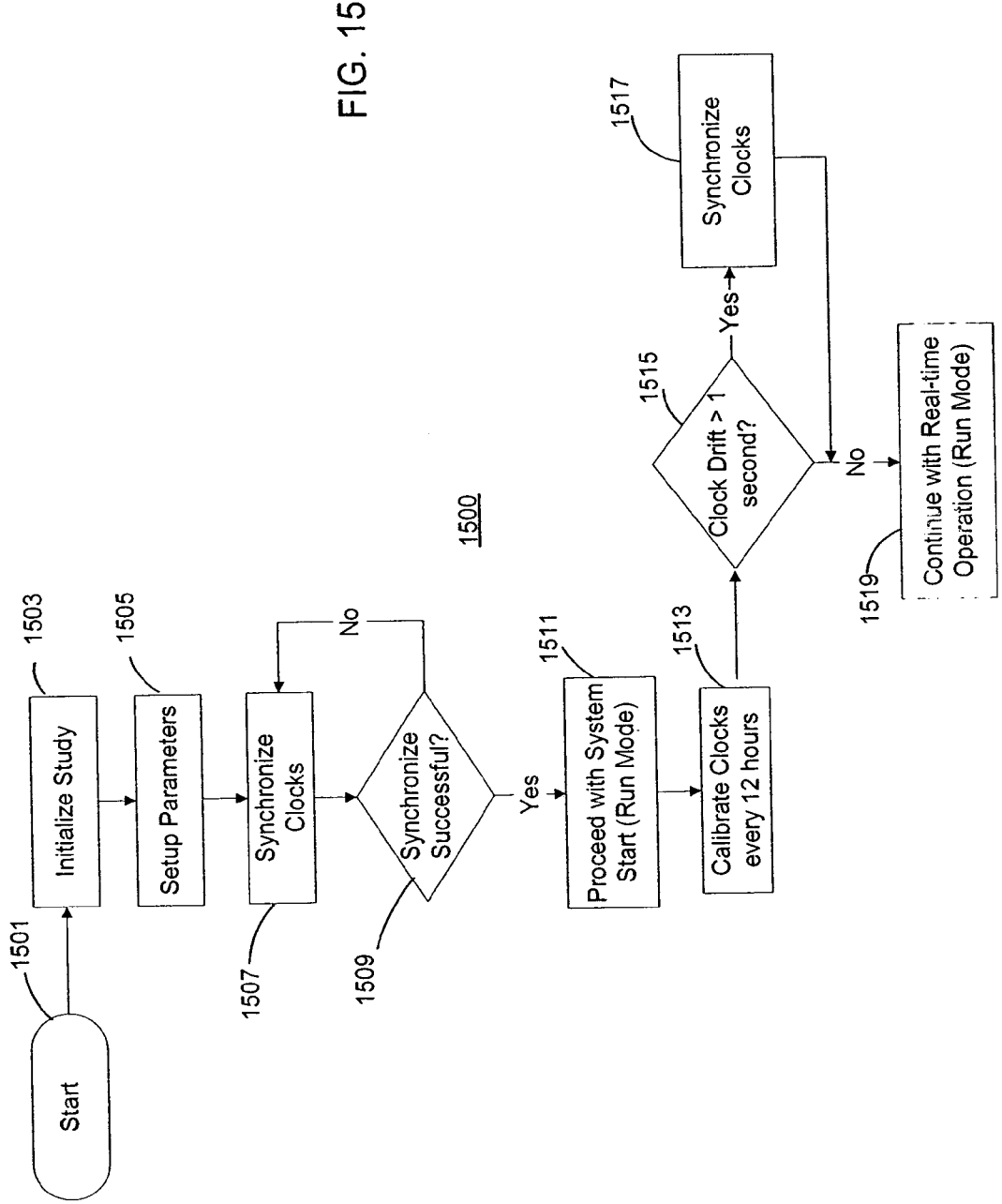
FIG. 15 shows a top-level flow diagram for clock synchronization and calibration for use with an external system.

FIG. 15 shows a top-level flow diagram for a clock synchronization and calibration process 1500. For clarity, the following discussion is provided in the context of the external system 100, although other embodiments are possible. In step 1503, a user initiates a study and sets-up the parameters through programmer 109 in step 1505. In the embodiment, the user enters a selected time (through programmer 109) that is different (which may be greater) than the reference time that is associated with monitoring equipment 105. (The reference time may comprise the associated date such month and day.) When the user determines that the time associated with monitoring equipment 105 equals the selected time, the user synchronizes the clocks in step 1507. Consequently, programmer 109 may generate a control message to bedside device 107 to synchronize the clock of bedside device 107. In the embodiment, the user selects an icon; however, other embodiments may use a Global Positioning System (GPS) clock reference or use a control line from monitoring equipment to activate the synchronization of clocks. In step 1509, programmer 109 determines if the clocks of bedside device 107 and programmer 109 were successfully synchronized and notifies the user through a real-time data display of programmer 109. In step 1511, the external system 100 starts run mode operation in which the medical device system may operate its intended functions.

During the operation of the external system 100 over time, the clocks of monitoring equipment 105, programmer 109, and bedside device 107 may drift with respect to each other. In the embodiment, the clocks of programmer 109 and bedside device 107 are calibrated using the clock of monitoring equipment 105 as a reference. In step 1513, the programmer 109 notifies the user that calibration should be performed (e.g., every 12 hours, although other time periods may be utilized). The user consequently enters a selected time (through programmer 109) that is greater than the present time that is associated with monitoring equipment 105. When the user determines that the time associated with monitoring equipment 105 equals the selected time, the user calibrates the clocks in step 1513. With the calibration process, the clocks of bedside device 107 and programmer 109 are not modified. Rather a "drift" time (equal to the difference between the clock in bedside device 107 and monitoring equipment 105) is stored to a file. Data that are subsequently collected by bedside device 107 can be correlated to the time of monitoring equipment 105 by adjusting the time of bedside device 107 by the drift time. (In the embodiment, the drift time is determined by the difference between the current time of the second clock and the reference time of the first clock.) However, if the drift time is determined to be greater than a predetermined threshold (e.g., one second) in step 1515, programmer 109 may notify the user that the clocks need to be re-synchronized or more frequently calibrated to accurately track the drift between the clocks. If that is the case, the clocks are synchronized in step 1517.

Figure 16:
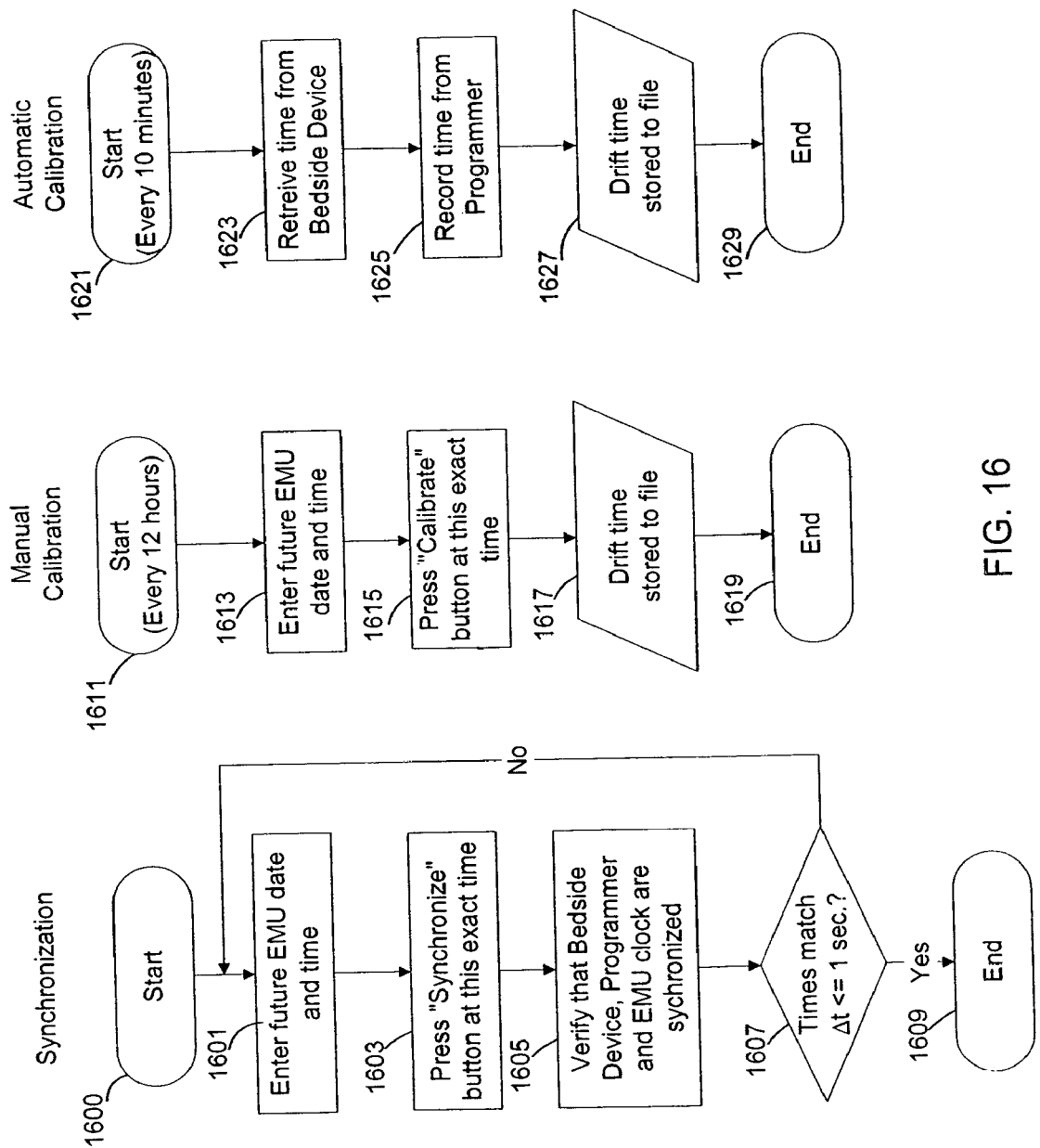
FIG. 16 shows specific flow diagrams for clock synchronization and calibration in relation to FIG. 15.

FIG. 16 shows specific flow diagrams for clock synchronization and calibration in relation to FIG. 15. Steps 1601–1609 correspond to synchronizing the clocks in the external system 100 as shown in steps 1507 and 1517. Steps 1611–1619 correspond to manually calibrating the clocks as shown in step 1513. Additionally, as shown in steps 1621–1629, the external system 100 may periodically (e.g., every 10 minutes) calibrate the clocks of the programmer 109 and bedside device 107 without requiring intervention by the user. In step 1623, programmer 109 retrieves the time from bedside device 107. Programmer 109 compares its time with the retrieved time from bedside device 107 and calculates an updated drift time. Programmer 109 stores the adjusted drift time for correlating times subsequently. As discussed, synchronization may also be utilized in either the hybrid or implanted systems. For example, in the embodiment of the implanted system, the implanted device may provide to or receive from an external component (e.g., patient or physician programmer, video equipment, testing equipment) a clock synchronization/calibration signal, and the calibration/synchronization techniques discussed herein may be utilized to correspond the implanted device with the one or more external devices. Moreover, the clock reference (i.e., the reference clock to which all other clocks would be synchronized/calibrated) may be the clock in the implanted component, one of the external components, a GPS clock, an atomic clock, or any other reference clock.

Other embodiments of the invention may determine a delay time between initiating the synchronization of clocks and the time that a clock receiving an indication to synchronization of the clock. For example, a second clock may receive a command of a radio channel from a first clock that provides a reference time. The propagation time for receiving a radio signal is approximately 5 microseconds for each additional mile in distance between the first clock and the second clock.

With other embodiments of the invention, synchronization of two clocks may occur on a periodic basis, e.g., every 24 hours. Also, as with embodiments using an atomic clock or a GPS clock, time adjustments that are associated with time zones may be supported. For example, the first clock and the second clock may be located in different time zones. In such a case, the second clock may be synchronized in accordance with the time zone that the second clock is situated. As another example, the second clock may be synchronized to adjust the time in accordance with a transition between standard time and daylight savings time.

Signal Quality Monitoring and Control

In accordance with another feature of the present invention, any one of the above-described medical device systems may be programmed so that it may monitor received neurological signals and analyze them to determine their quality. If a parameter of the received neurological signal for a particular monitoring element falls outside a certain range indicative of a degraded signal, the medical device system may recognize the signal as having poor quality until such time as the signal is restored to sufficiently good quality. Upon making the determination of poor quality, for example, the medical device system may decide to remove the signal from consideration in providing closed-loop feedback control. Alternatively, such signal quality monitoring may be utilized for data analysis in which case the degraded signal would be removed from consideration in the processing for data analysis. The sensed signals and quantitative analysis of their quality may also be provided to a treating physician or the medical device manufacturer. In addition, such entities and/or the patient may be notified of the existence of a degraded signal and/or that the signal has been removed from processing. This feature thereby removes from processing any neurological signal during periods when the signal quality is "sufficiently poor" and to resume processing of the signal once it is restored to "sufficiently good quality." For example, in the above-described application of a seizure detection system, a signal received from an electrode is removed from being provided as an input to the seizure detection algorithm during the time period that it is determined that the signal is of poor quality. For example, a signal having "clipping" (i.e., flatline) data may be indicative the signal exceeding voltage limits of the medical device system or experiencing amplifier saturation clipping.

The medical device system may calculate one or more variables that quantify the quality of the neurological signal received from each of the monitoring elements. For each variable, data points of the received neurological signal may be gathered and analyzed within a given moving window. The percentage of data points with associated signal quality variable falling above or below a predetermined range may be determined and monitored as the window moves with time. The resulting percentage values will be numbers between 0 and 100, representing quality, so that the medical system can quantify the quality of each associated window of data points. The medical system may use the computed quality to accept or reject data during monitoring. Depending on the embodiment of the medical device system, this process may be implemented as software modules within any one of the components of the external system, either the implantable device 953 or the external device 950, or within the implantable system 10. Each quality variable of the received raw neurological signal, or processed signals obtained through some transformation of the neurological signals to be used in subsequent processing, may be continuously and independently monitored. Separate software modules may exist for each quality variable of the signals being monitored.

As an example, the medical device system may monitor excessive flat-lining, which is distinguishable from that which may occur pre- or post-ictally, for a particular neurological signal. For example, a degraded signal may be one in which 40% of the signal values are clipped (e.g., 40% of the data points within the moving window are at the upper "rail"). Such a signal may be considered of poor quality and hence undesirable, as compared to one that has no clipping or only minimal clipping (e.g., 4–5%). The medical device system may therefore take instantaneous signal quality measurements and perform exponential-smoothing or some other averaging over a moving window. The length of the moving window may vary for different embodiments or over time and can have a 60-second duration in one embodiment. The medical device system may thereby compare the level of change between two adjacent data points in the moving window. If the data points' "quality variables" are within a predetermined value of each other, it is indicative of flat-lining. For example, if two adjacent data points are less than 2 bits of signal digital precision from (or, alternatively, within 10% of) each other, it may be determined to be indicative of instantaneous flat-lining. Another indication of flat-lining is where signals from two adjacent monitoring elements are identical. The medical device system may therefore ignore or substitute signals from a specific electrode if the number of flat-line data points in a given rolling window exceeds a predetermined amount or percentage relative to the total number of data points in the time window. Once the number of flat-line data points falls below a second (typically lower) predetermined amount, the medical device system may then re-enable the signal from that electrode to be used for processing (e.g., data analysis or closed-loop feedback control). The system may also provide notification to the physician and/or the patient of these events such as a sensory signal (e.g., alarm). Alternatively, the signal experiencing poor signal quality removed from processing may be replaced with a substituted signal. The substituted signal may be, for example, a signal that provides typical signal characteristics or may provide signal characteristics received from a neighboring monitoring element.

More particularly, a neurological signal is instantaneously flat-lined if the two-point signal differential is sufficiently small, i.e., if:

$$|x_{K+1} - x_k| \leq C_1$$

where $C_1$ is a specified parameter of the method. For example, $C_1 = 0$ causes clipping to be defined in the case of a strictly zero signal differential. Setting $C_1$ slightly larger than zero (e.g., corresponding to a few bits of precision in the input signal) allows potentially undesirable flat-lining that isn't exactly zero in differential to also be detected.

Even if the signal is of good quality, there may still be pairs of data points that will satisfy the above definition of being instantaneously flat-lined. This can occur, for example, around local extrema of the signal (when the first derivative is supposed to be zero). To allow the system to ignore such instances, a time-average of the indicator function of instantaneous flat-lining is provided. To minimize memory requirements and computational effort, the time-average may be implemented using exponential forgetting.

In this manner, the system generates a flat-line-fraction signal, which may be interpreted as the fraction of time that the signal was flat-lined in the most recent time window. The flat-line-fraction signal is initialized to zero, and has a value in the interval [0,1] at all times. The timescale of the moving window (i.e., its effective length) is determined by an exponential forgetting parameter, λflat, and may be quantified by the corresponding half-life of the exponential forgetting. The signal sampling rate, Fs, describes the relationship between λflat and the half-life, T1/2 as:

$$0.5 = \lambda_{flat}^{T1/2 Fs}$$

The parameters $\lambda_{flat}$ and $C_1$ should be chosen to ensure that the window of monitoring for the flat-line detection is sufficiently long to avoid disabling analysis for seizure detection just prior to an electrographic seizure that is preceded by signal quieting that may be a typical seizure onset precursor for the subject under study. The flat-line-fraction signal is next analyzed to determine whether or not there has been excessive flat-lining. This is accomplished by setting two thresholds: (1) "bad-fraction" where processing of the corresponding signal is disabled if the flat-line-fraction signal exceeds this threshold level; and (2) "restore fraction" where processing is re-enabled if it had been previously disabled, provided the flat-line-fraction signal has crossed back below this threshold level.

Figure 17:
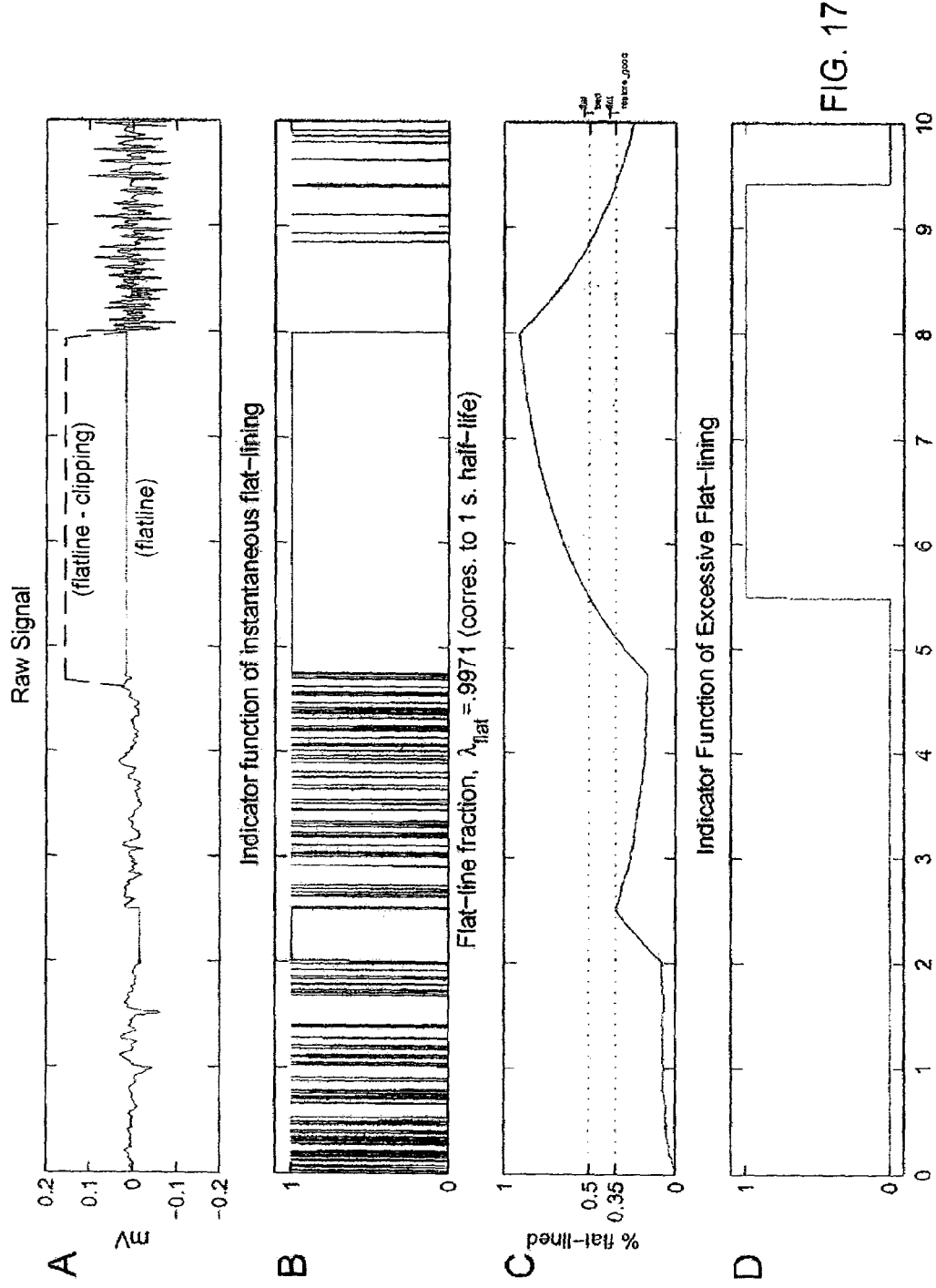
FIG. 17 depicts various graphs of a neurological signal containing flat-lined or clipped artifact data.

To illustrate signal flat-lining, FIG. 17 has been provided. FIG. 17A illustrates a signal containing flat data. FIG. 17A shows a signal that exhibits a portion of flatline data. Flatline line data may occur when the signal exceeds voltage limits (as indicated by "flatline—clipping") or may occur when the signal does not exceed voltage limits (as indicated by "flatline"). In the latter case, possible reasons may be that a lead is broken or that a lead is shorted to a ground potential. FIG. 17B shows a graph of the corresponding indicator function of instantaneous flat-lining. FIG. 17C shows a graph of the resulting flat-line-fraction signal with a $\lambda_{flat}$ parameter corresponding to a 0.5 second half-life. The threshold values for "bad-fraction" and "restore good-fraction" are also shown as 0.5% and 0.35%, respectively. FIG. 17D shows the output of the flat-line detector module which is set to "1" at times when the signal is determined to have excessive flat-lining and zero otherwise. One skilled in the art will appreciate that many other forms of poor signal quality can be similarly defined and detected using instantaneous quality variables and weighted time-averaging (e.g., the preferred exponential forgetting), followed by application of threshold criteria in order to disable and re-enable subsequent analysis/processing utilizing the resulting longer timescale signal quality assessments. Two very similar quality assessments arise from quantifying signal "clipping" or amplifier saturation at the maximum and minimum ranges, respectively, of an analog-to-digital converter. The fraction of time the signal spends on the maximum and minimum rails of the amplifier can be measured on any desired timescale and incorporated into the signal quality control system.

As another example, a neurological signal parameter that may be monitored for signal quality is a "mains" artifact, namely an excessive noise at a certain frequency, for example, approximately 60 Hz. Such a signal may be indicative of outside noise interference (e.g., caused by turning on a lightbulb) and may be indicative of a faulty or high-impedance electrode. Of course, the frequency may vary. For example, in European countries, the AC noise interference has a frequency of approximately 50 Hz. The medical device system may measure instantaneous amplitudes of the signal and calculate a running average for a given moving window, of 60 seconds duration. Once it is determined that the average frequency or amplitude of the signal is excessive, namely above a predetermined threshold, the medical device can remove the associated electrode from consideration in the data analysis process (e.g., a seizure detection algorithm). Once the average frequency or amplitude of the signal returns below a second (typically lower) predetermined level, the associated electrode may then be brought back into consideration.

The process for detecting excessive 60 Hz. "mains" artifact is somewhat similar to that used in detection of clipping. The difference is that instead of computing a clip-fraction signal at each point in time, an estimate of the current amplitude of the 60 Hz component in the recorded signal is calculated, again, smoothing the estimate via exponential forgetting. The output of this smoothing is interpreted as the average 60 Hz amplitude in the most recent time window (with a time constant determined by the half-life associated with the 60 Hz. exponential forgetting factor parameter). As before, the monitored neurological signal is considered bad/broken (disabling analysis of the signal) if the average 60 Hz. amplitude exceeds one threshold and is later considered good/fixed if it returns back below the same or a different threshold.

The instantaneous estimate of the amplitude of the 60 Hz. component of the input signal is obtained by first applying a digital filter to the input signal to remove energy from frequencies other than 60 Hz, leaving only the 60 Hz component of the received signal. This may be done using a 3 tap FIR filter that is the complement of a 60 Hz notch filter. This filter may not be sufficiently sharp in the frequency domain and may incorrectly detect, for example, a high frequency component present in a seizure as 60 Hz and disable processing of the signal (and thus miss potential detection of the nervous system disorder). Accordingly, an IIR filter or a longer FIR filter may be utilized to obtain additional specificity in the frequency domain. A similar approach may be taken to produce a 50 Hz. artifact detector (for example, for use in Europe).

After the 60 Hz component of the input signal has been extracted, the amplitude of the wave is estimated by computing the square root of twice the four point moving average of the square of the filtered signal. The reason behind this is easily derived from trigonometry and omitted here. The instantaneous estimate of 60 Hz amplitude may have a relatively large variance due in part to the fact that the estimates are each completely derived from four data points of information. The sequence of instantaneous estimate is therefore smoothed, utilizing exponential forgetting for memory and computational efficiency, to produce a signal, "amp60est," that tracks the time-varying amplitude of 60 Hz noise present in the signal. The amp60est signal is interpreted as a time-average of this noise over a recent time window (the length of the window may be determined by the half-life of the exponential forgetting parameter, $\lambda_{60}$).

The amp60est signal is next analyzed to determine whether or not there has been excessive 60 Hz noise in the recent signal. This is accomplished by setting two thresholds: (1) "amp60bad" where processing of the corresponding signal is disabled; and (2) "amp60restore_good" where processing is re-enabled if it had been disabled, provided amp60est has crossed back below this threshold level.

Other than an IIR or FIR filter, an alpha detector may be created by using a filter in the 8–13 Hz band. In this event, it may be desirable to ensure that the approach used to estimate the amplitude of a single frequency sine wave was adapted or verified to work for estimating total power of the portion of signal in the particular frequency band, and that the resulting system was validated against expert visual analysis. The use of this filter is restricted to non-epileptogenic regions so as not to impair the process of seizure detection or quantification since 8–13 Hz signal components may be present in seizures.

Figure 18:
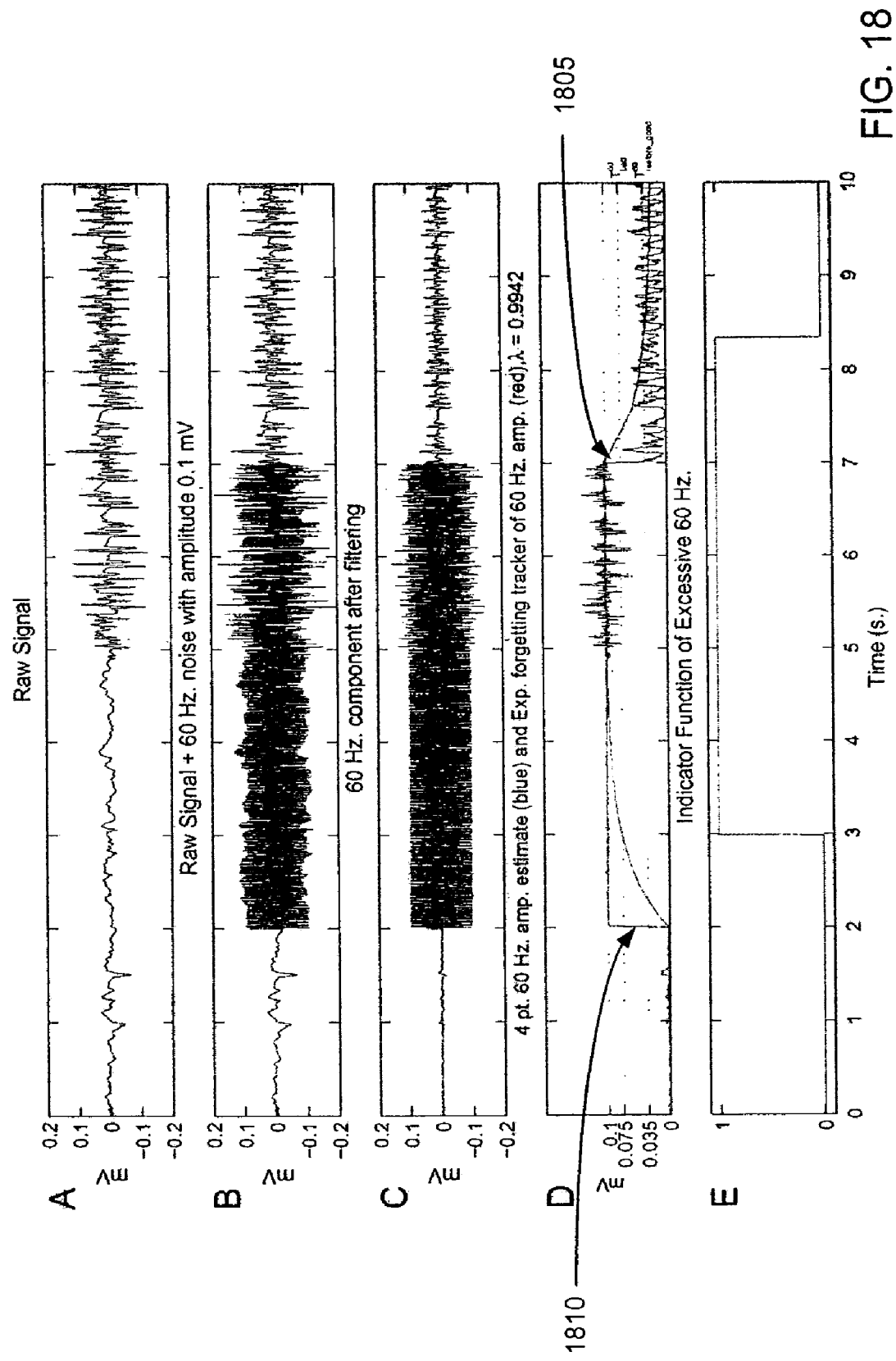
FIG. 18 depicts various graphs of a neurological signal containing 60 Hz artifact data.

FIG. 18A shows a 10-second segment of ECoG data (with a seizure beginning at t=5 seconds). FIG. 18B illustrates the same ECoG signal segment, but contaminated by an excessive 60 Hz artifact (0.1 mV noise, beginning at t=2 seconds and ending at t=7 seconds). FIG. 18C illustrates the 60 Hz component of the noisy signal, extracted via the 3 pt. FIR filter with coefficients [0.5, 0, −0.5] (using a MATLAB filter convention for coefficient ordering and sign). FIG. 18D shows a graph of the instantaneous (i.e., 4-point) estimate of 60 Hz. amplitude (1805), along with the resulting "amp60est" signal (1810), computed using the parameter $\lambda_{60}$=0.9942 (corresponding to a 0.5 second half-life at sampling rate Fs=240 Hz). The threshold values for "amp60bad" and "amp60restore_good" are also annotated as 0.075 mV and 0.035 mV, respectively. FIG. 18E shows the output of the 60 Hz. artifact detector module, which is set to one at times when the signal is determined to have excessive 60 Hz. noise and zero otherwise.

It will be appreciated that the clipping artifact and the 60 Hz artifact are examples of signal quality that can be monitored. Still other features of the recorded signal, such as signal wave shape (e.g., smoothness indexes), may also be considered. Processing of signal wave shapes would determine artifactual waves unlike those generated by the brain such as portions of a signal with straight lines, sharp angles, or lacking any variability.

For example, poor signal quality may be determined when one signal is significantly different from another signal in some respect, but wherein the corresponding electrodes are physically near each other. In this example, power may be calculated and a poor signal may be the cause if one signal exceeds the bounds for what is expected for signals from adjacent electrodes, or if the absolute-value of the correlation coefficient between the two signals is low, when it would, by the spatial closeness of the electrodes, be expected to be higher.

A maximal amount of poor quality data that is tolerable may be qualified using different criterion. Poor quality data may be gauged by a signal power to noise power ratio (S/N) that is associated with neurological data. Also, poor quality data may be gauged by a fraction of the foreground window that contains a noisy signal. Typically, the foreground window is more vulnerable to noise than the background window since the foreground is determined over a shorter time duration. One may also consider different artifacts. Movement artifacts may be detected with accelerometers, in which corresponding outputs may be used to reduce or even cancel the movement artifacts. Other types of artifacts that may be consider include EKG artifacts and disconnection artifacts. EKG artifacts, when recorded from intracranial electrodes, are an indication of high impedance. Disconnection artifacts may be identified by stationary noise in one lead or a set of leads. The characteristics of a baseline that are associated with neurological data may assist in identifying a cause of poor quality data. For example, a flat line without a shift in the baseline and without noise may be indicative that an amplifier has been deactivated or has failed.

Screening Techniques for Management of a Nervous System Disorder

The medical device system may have a mode of operation for performing screening of a nervous system disorder. The system may thereby make decisions about the patient's options for management of the nervous system disorder. For clarity, the following discussion is provided in the context of the external system 100, although other embodiments are possible. In the discussion, a neurological signal may be an EEG signal that is sensed by one or more monitoring electrodes. However, in other embodiments of the invention, a neurological signal may be provided using other types of monitoring elements such as one or more sensors. Treatment therapies may include any number of possibilities alone or in combination including, for example, electrical stimulation, magnetic stimulation, drug infusion, and/or brain temperature control. During screening, the medical device system may perform various operations. For example, in the embodiment of treating a seizure disorder, the system may identify a patient's seizure focus or foci by determining portions of the brain that are associated with a seizure. In general, the neurological event focus is the anatomic location where the neurological event originates. Accordingly, the medical device system may identify electrode placement that may provide effective therapy and provide recommendations on which sensing and stimulation combinations are more effective than other sensing and stimulation combinations. The recommendations may utilize a focal therapy assessment that is effective if the extent of electrographic spread is contained in the seizure focus and does not spread elsewhere (i.e., partial seizures). Alternatively, the recommendation may utilize a remote therapy assessment that is effective if seizure related electrographic activity originates in the seizure focus and propagates to other brain regions (i.e., secondarily generalized seizure types). Moreover, the medical device system may assess whether closed-loop therapy will be effective.

Figure 19:
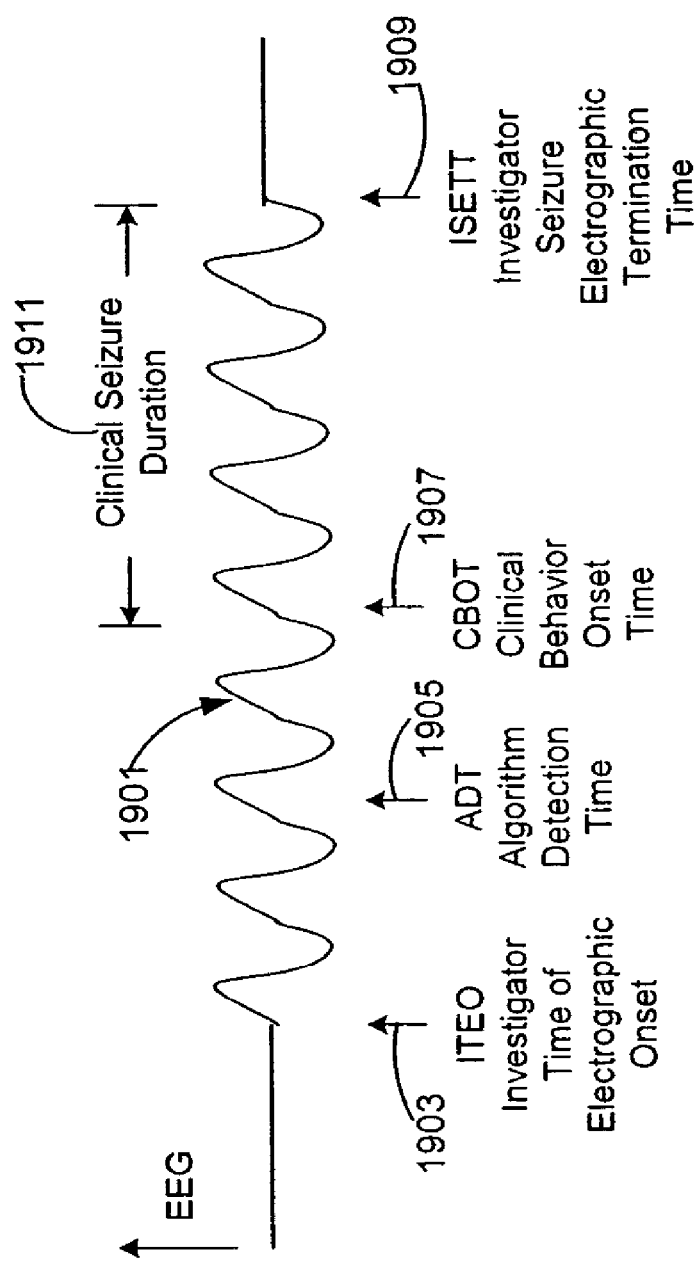
FIG. 19 shows simulated EEG waveforms, designating an onset of a neurological event.

FIG. 19 shows a simulated EEG waveform 1901, designating an onset of a neurological event. A time event 1903 corresponds to an investigator time of electrographic onset (ITEO), in which a clinician observes significant electrographic activity that may predict a neurological event such as a seizure. (However, a neurological event may not follow time event 1903 in some cases.) A time event 1905 corresponds to an algorithm detection time (ADT), in which a detection algorithm of external system 100 detects an occurrence of a neurological event. In the embodiment, as is discussed in the context of FIG. 20, the ITEO and the ADT are compared. The difference between the ITEO and the ADT provides a measure of the detection algorithm's delay of detection for detecting a neurological event. In general, it is desired for the delay of detection to be as small as possible with sufficient accuracy of predicting the neurological event. In order to accurately determine the difference between the ITEO and the ADT, associated clocks should be sufficiently synchronized (as is discussed in the context of FIG. 15).

A time event 1907 corresponds to a clinical behavior onset time (CBOT), in which a patient manifests the symptoms of the neurological event (such as demonstrating the physical characteristics of a seizure). (In some cases, the patient may not manifest the symptoms even though an ITEO occurs.) Typically, if monitoring elements (such as electrodes) are appropriately positioned, the CBOT will occur after the ITEO. However, if the electrodes are placed away from a point of the neurological event, the CBOT may occur before the ITEO because of a delay of the neurological signals propagating through different portions of the patient's brain. A time event 1909 corresponds to an investigator seizure electrographic termination time, in which the electrographic activity sufficiently decreases.

Figure 20:
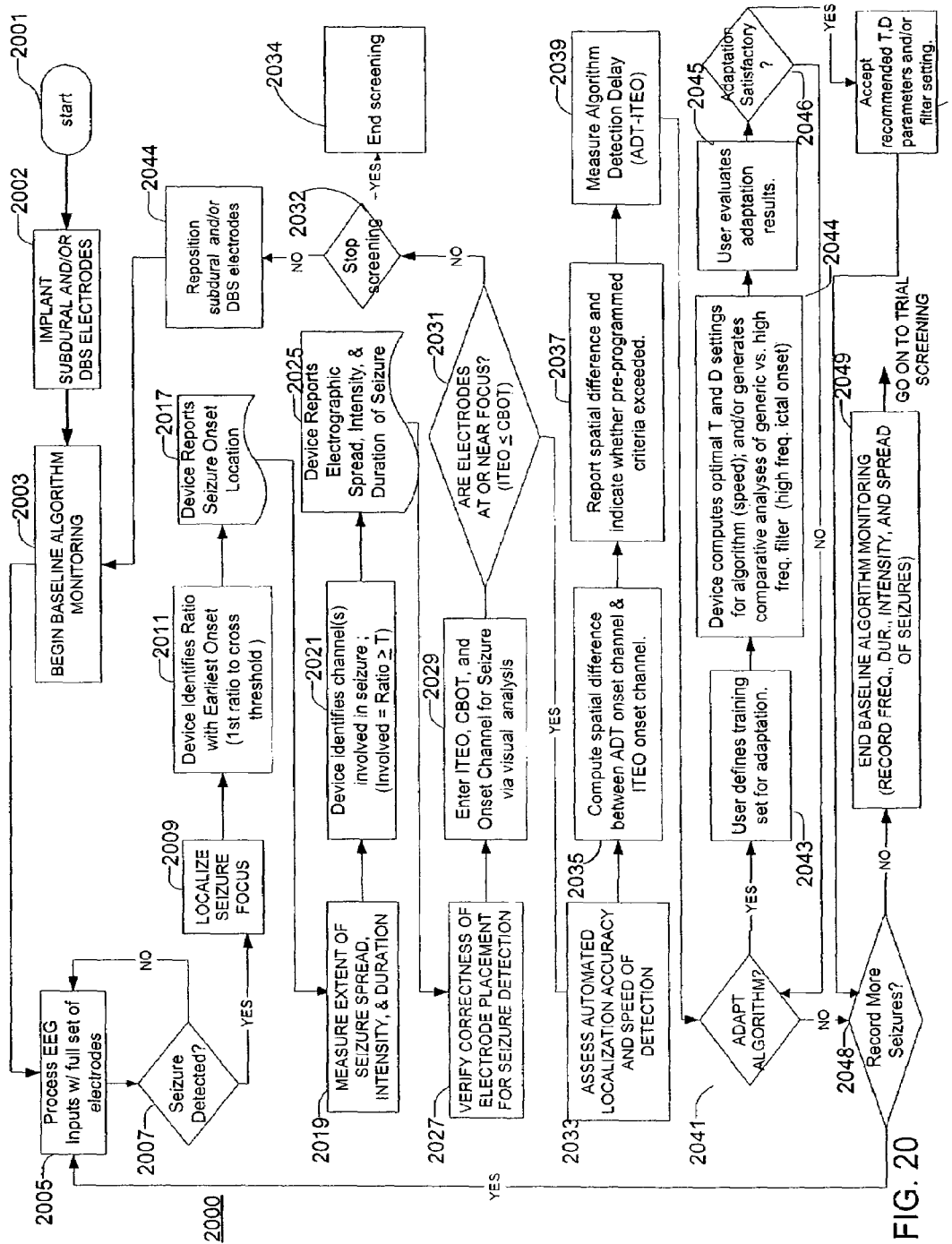
FIG. 20 shows a flow diagram for a seizure screening procedure to define treatment therapy according to an embodiment of the invention.
Figure 21:
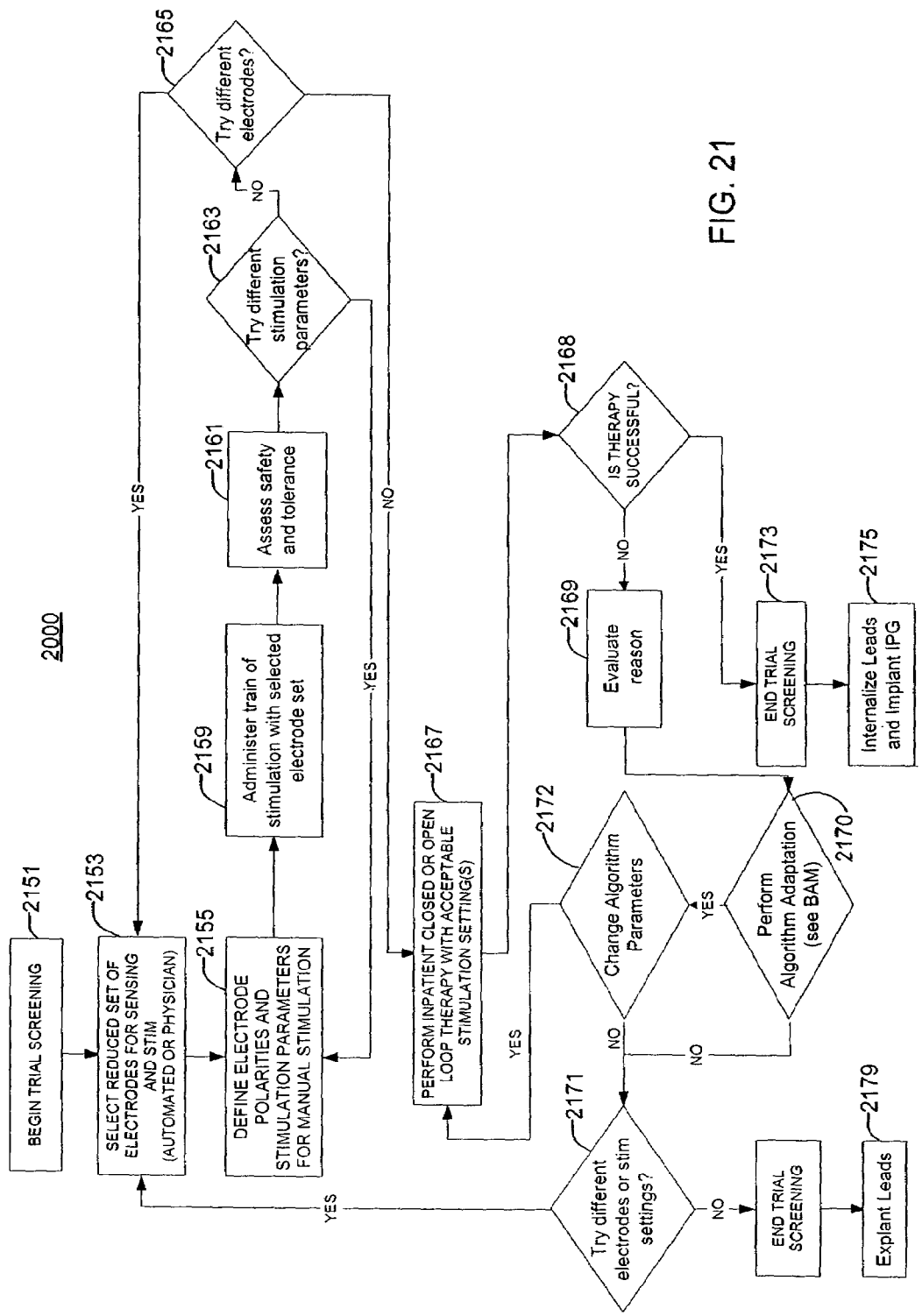
FIG. 21 shows a continuation of the flow diagram that is shown in FIG. 20.

To illustrate an embodiment of a screening procedure for a particular nervous system disorder, FIGS. 20 and 21 show flow diagrams for a seizure screening process to define treatment therapy according to an embodiment of the invention. Process 2000 comprises a baseline algorithm monitoring sub-process 2003 (comprising steps 2005–2049) and a trial screening sub-process 2151 (comprising steps 2153–2179). In step 2002, a physician implants electrodes into a patient in order to conduct process 2000.

In step 2005, a medical device system processes neurological signals (e.g., EEG inputs) that are sensed by the implanted electrodes. If a detection algorithm (that is utilized by the medical device system) detects a seizure in step 2007, a location of the seizure, as characterized by a seizure focus location, is determined by step 2009 and comprising sub-step 2011 and sub-step 2017. (In the discussion, herein, a "step" may comprise a plurality of "sub-steps." For example, when performing step 2009, process 2000 performs both sub-steps 2011 and 2017. One should not construe sub-steps 2011 and 2017 as being distinct from step 2009.) In sub-step 2011, the medical device system identifies the seizure focus location by identifying the channel(s) (corresponding to an implanted electrode) with the earliest onset in which a predetermined ratio threshold is crossed. In some neurological events, several foci may be identified. Also, a patient may experience a plurality of neurological events, which are associated with different foci. In sub-step 2017, the medical device system reports at least one seizure onset location through an output device.

In step 2019 (comprising sub-step 2021 and sub-step 2025) an extent of the seizure's spread, intensity, and duration are determined. In sub-step 2021, the medical device system identifies channels that are "involved" in the seizure in order to determine an electrographic spread of the seizure. (A criterion for channel involvement and electrographic spread is discussed in the context of FIG. 22.) The medical device system reports the electrographic spread, intensity, and duration to the physician in sub-step 2025. The medical device system may present a graphical representation of the patient's brain to an output device for the physician's viewing. The graphical representation highlights the location and the extent of the seizure focus (such as by distinguishing the portion of the brain that is neurologically involved in the seizure with a different color from other portions of the brain.) The graphical image may be three dimensional and may present a sequence of images as a function of time, where each image represents the portion of the brain involved in the seizure at that particular point in time (seizure animation). Such a sequence of images graphically displays the manner in which the seizure spreads through the patient's brain from onset until termination (seizure animation).

In step 2027, which comprises sub-steps 2029 and 2031, the correctness of electrode placement for seizure detection is verified. In sub-step 2029, the ITEO (investigator time of electrographic onset corresponding to time event 1903 in FIG. 19) and the CBOT (clinical behavior onset time corresponding to time event 1907 in FIG. 19) are provided to the medical device system. (In the embodiment, step 2027 is optional so that the clinician need not provide ITEO and CBOT to the medical device system.) In sub-step 2031, the medical device system determines if the ITEO did not occur after the CBOT. In the embodiment, the fact that the CBOT occurs before the ITEO is indicative that the selected electrodes are not sufficiently near the focus. In such a case, step 2032 determines whether to stop screening. If so, screening is ended in step 2034. Otherwise, step 2004 allows the physcian to reposition subdural and/or DBS electrodes. The baseline algorithm monitoring sub-process 2003 is repeated.

If sub-step 2031 determines that the ITEO does not occur after the CBOT, step 2033 is executed, in which a localization accuracy and speed of detection are determined. Step 2033 comprises sub-steps 2035, 2037, and 2039. (In the embodiment, step 2033 is optional so that the clinician need not provide ITEO and CBOT to the medical device system.) In sub-step 2035, a spatial difference is determined between a ADT onset channel (i.e., the channel that the detection algorithm associates with the onset of the seizure) and a ITEO onset channel (i.e., the channel that is first associated with neurological activity as determined through visual analysis). While the ADT onset channel may be different than the ITEO onset channel, an event of the ADT onset channel and the ITEO onset channel being the same is indicative of localization accuracy. In sub-step 2037, the medical device system reports the spatial difference and whether the spatial difference exceeds a predetermined limit. The spatial difference exceeding the predetermined limit may be indicative that algorithm adaptation should be executed as in step 2041. In addition, in step 2039, a measure of the algorithm's detection delay is determined by calculating the difference between the times associated with the ADT and the ITEO. If the detection delay is sufficiently large, algorithm adaptation may be executed in step 2041.

Step 2041 determines whether to adapt the detection algorithm. If not, step 2048, as describer later, is executed. If so, step 2043 enables the physician to provide a training set (e.g., cluster data for previous seizures) so that the detection algorithm may enhance performance by adjusting its parameters. The use of filter adaptation for detecting seizures is disclosed in U.S. Pat. No. 5,995,868 entitled "System for the Prediction, Rapid Detection, Warning, Prevention, or Control of Changes in Activity States in the Brain of a Subject" and is incorporated herein in its entirety. In sub-step 2043, the physician identifies collected neurological data that characterizes the seizure (e.g., one or more detection clusters that are associated with the seizure). The detection algorithm may be adapted using different methods, as requested by the physician or automatically (unsupervised learning). With one variation of the embodiment, the detection algorithm, in step 2044, is adapted by adjusting threshold and time duration settings in order to approximately optimize seizure detection in relation to the data identified in sub-step 2043. In step 2045, the physician evaluates the adaptation results. In step 2046, if the adaptation is satisfactory, the physician may accept recommended settings through an input device in step 2047. However, if the adaptation is not satisfactory, as determined by step 2046, step 2048 is executed to determine whether to record more seizures. If so, baseline algorithm monitoring sub-process 2003 continues to execute for subsequent seizures. Otherwise, process 2000 proceeds to trial screening sub-process 2151.

In a variation of the embodiment, user interaction may be reduced or even eliminated in some or all of the steps. For example, in steps 2045–2047, a set of predetermined criteria may be used in order to determine whether adaptation is satisfactory. Criteria may include speed of detection and detection falsing. Thus, the degree of automation may be increased or decreased for process 2000.

In step 2153, the physician inputs an electrode configuration in accordance with the electrographic spread and the seizure focus location that is presented to the physician in steps 2017 and 2025. In another embodiment of the invention, the medical device system provides a recommendation of the electrode configuration to the physician in accordance to the electrographic spread and the seizure focus location. The physician may accept, reject, or modify the recommendation. A "perform_manual_stimulation" step 2155 comprises sub-steps 2159 and 2161. The physician defines electrode polarities and stimulation parameters. (In an embodiment, an electrode polarity may be classified as a stimulation parameter. Also, some embodiments may utilize the can or case of the medical device as one or more electrodes (or as contacts) for recording and/or stimulation purposes.) Programmer 109 may provide suggested values based on the location of the electrodes and an historical compilation of values that have been accumulated through the evaluation of many patients. In sub-step 2159, therapy is administered by delivering stimulation to the patient. If the physician notes any adverse reaction to the treatment, the physician inputs an indication to the medical device system in sub-step 2161 indicating corresponding symptoms or changes that the patient shows. The medical device system queries the physician whether to modify any of the therapy parameters in step 2163 and the electrode configuration in step 2165. Step 2155 and sub-steps 2159 and 2161 are repeated if different stimulation parameters are tried in response to step 2163. Step 2153 is repeated if different electrodes are tried in response to step 2165. Alternatively, the medical device can recommend changes to the parameters.

If the physician indicates that the stimulation settings and the electrode configuration should be used, the medical device system applies treatment in step 2167. The medical device system or the physician determines whether the therapy is considered successful in step 2168 by a set of criteria. In the embodiment, the medical device system determines if there is a sufficient reduction of a detected frequency, duration, intensity, and extent of the electrographic spread that are associated with the seizure.

If the therapy is not deemed successful in step 2168, algorithm adaptation may be performed in step 2170. Step 2170 essentially functions as in step 2041. If step 2170 determines that algorithm adaptation shall not be performed, step 2171 is next executed. Otherwise, step 2172 determines whether algorithm parameters shall be changed. If so, step 2167 is executed; otherwise, step 2171 is executed. In step 2171, the electrodes may be reconfigured and step 2153 may be repeated. In a variation of the embodiment, restimulation of electrodes may be expanded to electrodes that are involved in the seizure other than the first or second electrode as determined in sub-step 2021. If subsequent trial screening shall not try different electrodes or stimulation settings (as determined by the physician), sub-process 2151 is completed and the electrodes may be explanted. If the therapy is deemed successful in step 2168, sub-process 2151 is completed.

In step 2168, the medical device system may compare the detected frequency, duration, intensity, and extent of the electrographic spread that is collected during baseline monitoring algorithm sub-process 2003 (as shown in FIG. 20) with the corresponding results that are collected during trial screening sub-process 2151. However, with stimulation, which is associated with trial screening sub-process 2151 but not with baseline monitoring algorithm sub-process 2003, blanking is generated during different time intervals, in which data is not collected because of signal artifacts. (Further detail is presented in the context of FIG. 23.) During intervals of blanking, corresponding data (which may be associated with neurological signals provided by electrodes being blanked and by adjacent electrodes) is not compared between baseline monitoring algorithm sub-process 2003 and trial screening sub-process 2151. If the difference between corresponding data, with and without stimulation, is sufficiently large (e.g., the difference is greater than an efficacy requirement), then the therapy is determined to be successful.

In other embodiments of the invention, in step 2169, a physician may evaluate a reason for the therapy deemed as not being successful. Consequently, the physician may instruct external system 100 to perform algorithm adaptation in step 2170. Alternatively, the physician may instruct external system 100 to bypass step 2170 and to perform step 2171, in which the electrodes are reconfigured.

With a variation of the embodiment, the medical device system may apply stimulation every $n^{th}$ block of detection clusters and/or every $n^{th}$ detection cluster (which is discussed in the context of FIG. 22) during trial screening sub-process 2151. Corresponding data (e.g., detected frequency, duration, intensity, and extent of the electrographical spread) is collected for both detection clusters, in which stimulation is applied, and detection clusters, in which stimulation is not applied. Because blanking is generated during different time intervals when stimulation occurs, corresponding data is not collected during the corresponding time intervals for detection clusters, in which stimulation is not applied so that the efficacy of the therapy can be evaluated. If the difference between corresponding data, with and without stimulation, is sufficiently large (e.g., the difference is greater than an efficacy threshold), then the therapy is determined to be successful.

Other embodiments of the invention may support other types treatment therapy such as magnetic stimulation, drug infusion, and brain temperature control, in which the efficacy of therapy may be evaluated by comparing corresponding data between baseline algorithm monitoring sub-process 2003 and trial screening sub-process 2151 or by comparing corresponding data between detection clusters, in which treatment therapy is applied, and detection cluster clusters, in which treatment therapy is not applied.

Configuring and Testing Treatment Therapy Parameters

The medical device system may have a "manual" treatment therapy mode that is different from a normal run mode (automated mode), in that stimulations may be delivered by the user, in order to test the clinical efficacy and tolerability of therapy configurations. In the manual treatment therapy mode, the medical device system may enable the user to select parameters (i.e., intensity, frequency, and pulse width), therapy element configurations, to assess charge density, to test treatment therapy levels, to insure safety to the patient, and to determine efficacy and tolerability. With parameter selection, the medical device system enables the user to define one or more treatment therapy configurations having associations with a combination of treatment therapy parameters. For clarity, the following discussion is provided in the context of the external system 100, although other embodiments are possible. In the discussion, a neurological signal may be an EEG signal that is sensed by one or more monitoring electrodes. However, in other embodiments of the invention, a neurological signal may be provided using other types of monitoring elements such as one or more sensors. Treatment therapies may include any number of possibilities alone or in combination including, for example, electrical stimulation, magnetic stimulation, drug infusion, and/or brain temperature control. In the embodiment where treatment therapy is electrical stimulation, the parameters may include, for example without limitation, duration of stimulation, intensity (in volts or amps), pulse width, stimulation frequency, pulse shape etc. With drug infusion therapy, parameters include a drug type, a drug dosage, at least one infusion site, infusion rate, and a time of delivering the drug dosage. The user may save each tested treatment therapy configuration and may identify each configuration by a specified name. In the embodiment, the medical device system verifies that the specified name is associated with a unique configuration so that two different names are not associated with the same configuration.

Before a user-defined treatment therapy configuration is even tested or stored, the medical device system preferably performs a charge density check. For example, in the embodiment of electrical stimulation therapy, the medical device system computes the charge density of the stimulation configuration using the impedance of the electrode configuration, voltage level, stimulation pulse width and contact geometry of the electrode configuration. The charge density may be computed using the following formula:

$$(I \cdot \Delta w)/(\text{surface area of electrode})$$

where I is the current of the stimulation pulse and is approximately equal to the voltage level divided by the impedance, and $\Delta w$ is the pulse width. If the calculated charge density exceeds a preset threshold, the medical device system considers the stimulation configuration to be not valid and prevents and/or warns the user from testing with the associated stimulation configuration. In a preferred embodiment, the preset threshold is approximately 30 $\mu$coulombs/cm$^2$/phase and can be in the range of up to 500 $\mu$coulombs/cm$^2$/phase. The preset threshold can be programmable and, of course, may vary depending on the nervous system disorder being treated and/or the medical device system. For example, co-pending U.S. patent application Ser. No. 10/099,436, Goetz et al., "Automated Impedance Measurement of an Implantable Medical Device," and filed on Mar. 15, 2002 discloses apparatus and method for automating impedance measurements of sets of electrodes that are associated with a lead of an implanted device. Alternatively, in another embodiment, the current may be measured directly for each electrode and the value may be used to compute the charge density.

The medical device system may also ensure other efficacy criterion are satisfied for any user-defined treatment therapy configuration. For example, the medical device system providing stimulation therapy may ensure that the polarities of the stimulation pulses are properly defined, e.g., all polarities cannot be off and that the voltage level is greater than zero on at least one stimulation channel, and that at least one cathode and at least one anode are configured.

If a treatment therapy configuration is within a permissible charge density range, the medical device system allows the user to test the treatment therapy configuration. During a test, the user is able to use a start/stop delivery capability of the medical device system. If the delivery is not terminated by the user, the medical device system continues to deliver treatment therapy for the specified time duration. The medical device system then queries the user whether or not the treatment therapy configuration was acceptable. The user (e.g., patient or physician care-giver) responds with a "yes" or "no" through programmer 109. In other embodiments, a treatment therapy level that is beyond the point at which the user stops delivery is considered as not tolerated by the patient. Moreover, the medical device system may insure that the treatment therapy configuration corresponds to a treatment that is safe to the patient, where the treatment therapy configuration is within a configuration range of safety. Safety to the patient is gauged by an expectation that the treatment does not diminish the health of the patient.

In the embodiment where the medical device system is providing treatment of seizure disorders, the medical device system operates seizure detection algorithm 800 in real-time during the manual stimulation mode, as in the normal run mode, but with detection-triggered stimulation disabled. When selecting stimulation parameters for therapy use, the medical device system allows the user to select from a list of stimulation parameter configurations, which have been previously defined and tested in the manual stimulation mode. The user may be restricted to selecting only those stimulation configurations that were tolerated by the subject during testing in the manual stimulation mode. Once configured, the medical device system may return to normal mode of operation to provide detection-triggered stimulation in accordance with the stimulation configuration set by the users.

Figure 22:
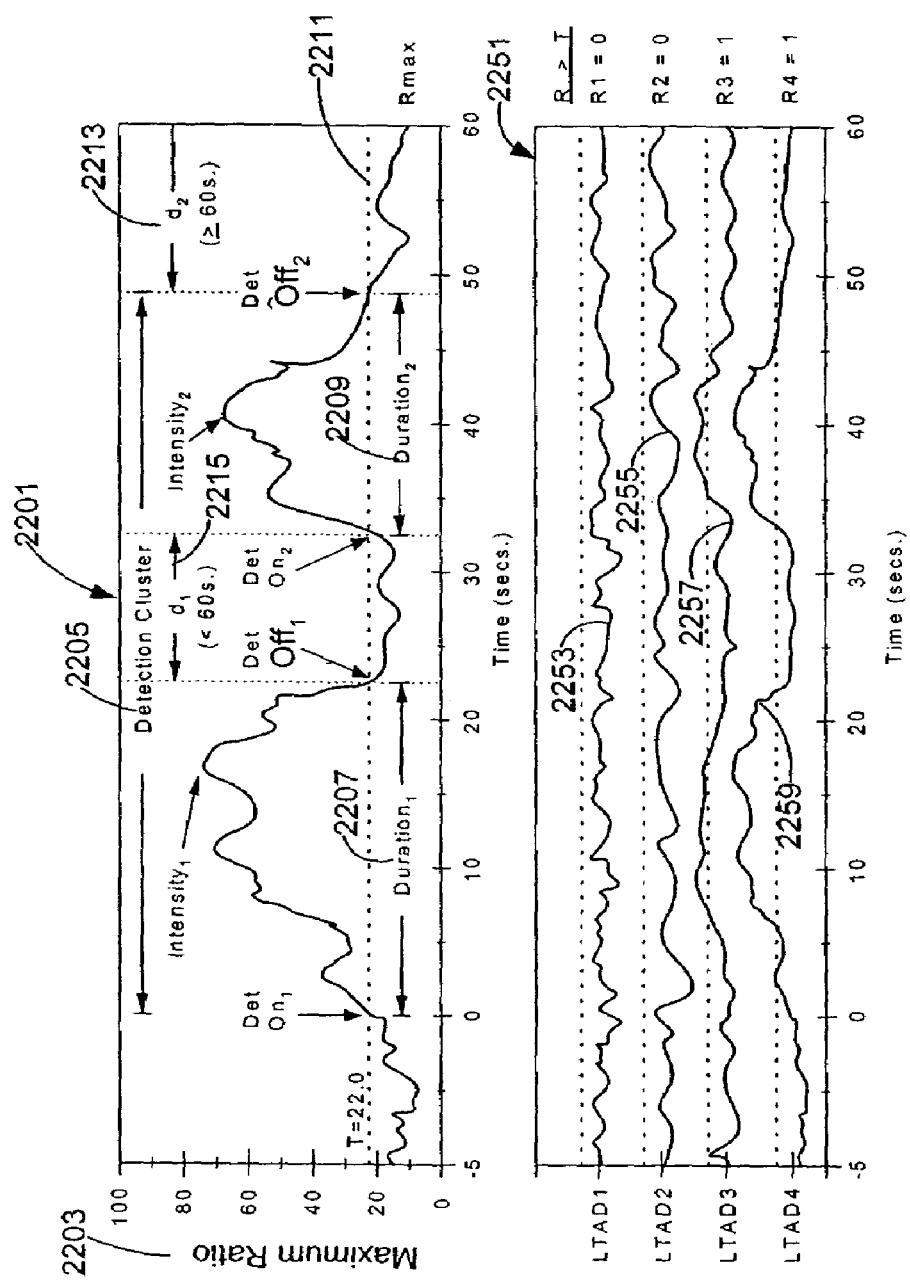
FIG. 22 shows data associated with a maximal ratio as determined by a seizure detection algorithm for detecting a cluster.

Clustering of Recorded Patient Neurological Activity to Determine Length of a Neurological Event EEG activity, as monitored with a seizure detection algorithm, during a neurological event (such as a seizure) may result in multiple closely-spaced detections that the user may wish to interpret as being part of one event (seizure), and which, if considered as separate events, may result in an unnecessary or even unsafe number of treatments. This may be particularly true at the beginning or end of a neurological event time when oscillations around the detection threshold may result in multiple closely-spaced detections, which may complicate operations and logging of events. For clarity, the following discussion is provided in the context of the external system 100, although other embodiments (as with a hybrid or an internal system) are possible. In the discussion, a neurological signal may be an EEG signal that is sensed by one or more monitoring electrodes. However, in other embodiments of the invention, a neurological signal may be provided using other types of monitoring elements such as chemical or thermal sensors. Treatment therapies may include any number of possibilities alone or in combination including, for example, electrical stimulation, magnetic stimulation, drug infusion, and/or brain temperature control. A medical device system, e.g., external system 100, determines detection clusters using a temporal criterion, based on the distributions of durations of ictal discontinuities or interictal time intervals. Detections that are separated in time by a programmable inter-detection interval are assigned to the same cluster unit and deemed as being part of the same seizure as shown in FIG. 22. Clustering parameters are programmable.

FIG. 22 shows data 2201 associated with a maximal ratio 2203 as determined by seizure detection algorithm 800 for quantifying a seizure, as represented by a detection cluster 2205. Data 2201 (as obtained from a loop recording generated by bedside device 107) shows maximal ratio 2203 from 5 seconds before an onset of detection cluster 2205 to 12 seconds after the end of detection cluster 2205. (Other embodiments of the invention may determine the occurrence or other types of a neurological event that is associated with a nervous system disorder.) Maximal ratio 2203 (for a given instant in time) is determined from a waveform frame 2251 by identifying an EEG waveform (2253, 2255, 2257, or 2259) having the largest ratio at the given instant in time. (The ratio of an EEG waveform at a given time is the largest ratio of a short-term value (foreground) divided by a long-term value (background) over a set of neurological signals or channels. (A short-term value or a long-term value may be an average value, a median value, or some other statistical measure.) In the embodiment, the short-term value spans the previous 2 seconds of EEG data, and the long-term value spans the previous 30 minutes or more. Other embodiments may use short-term and long-term values spanning different time durations.) For example, at a time approximately equal to 10 seconds, waveform 2259 is associated with the largest ratio, and that ratio is used to construct data 2201 at the same point in time. A predetermined threshold 2211 sets a minimum threshold (equal 22.0) for detecting seizure activity. However, a time constraint is predefined such that if data 2201 falls below predetermined threshold 2211 and subsequently raises above predetermined threshold 2211 within a time constraint 2215 (which corresponds to 60 seconds in FIG. 22), then that subsequent portion of data 2201 is considered to be part of detection cluster 2205. Thus, detection cluster 2205 equals duration 2207 plus the measured time d1 plus duration 2209. Cluster intensity is determined by the largest maximal ratio during detection cluster 2205.

In the embodiment, the content of abnormal or of signal of interest in an ensemble of neurological signals and the prespecified threshold value determines an onset of detection cluster 2205. In such a case, if the "seizure content" of an ensemble of neurological signals is above predetermined threshold 2211 for a minimum time duration, seizure detection algorithm 800 determines that detection cluster 2205 has begun. However, in other embodiments of the invention, seizure detection algorithm 800 may determine that detection cluster 2205 has occurred only if the neurological signal that first crossed predetermined threshold 2211 stays above predetermined threshold 2211 for the minimum time duration.

Other embodiments of the invention may use another measure other than a ratio to determine an occurrence of detection cluster 2205. Other measures include an amplitude of a neurological signal and a magnitude of a frequency spectrum component (as may be measured by a Fourier transform) of a neurological signal.

Waveform 2253, 2255, 2257, or 2259 is considered "involved" in a seizure if the corresponding ratio equals or exceeds predetermined threshold 2211. (In FIG. 22, the time duration constraint equals approximately 0.84 seconds.) Each waveform in FIG. 22 is associated with a different electrode. In waveform frame 2251, waveforms 2257 and 2259, which correspond to adjacent electrodes, are "involved" in the seizure, and thus the extent of an electrographic spread is two electrodes.

In the embodiment, external system 100 may numerically indicate the electrographic spread, as is illustrated in the example above. Moreover, a variation of the embodiment may visually indicate the electrographic spread by distinguishing an electrode corresponding to a waveform that is "involved" in the seizure. In the variation of the embodiment, a graphical representation of the patient's brain is shown with the electrodes that are associated with the seizure as distinguished by a color (such as red). Alternatively, the electrodes that are not associated with the seizure may be distinguished by some other color. While determining extent of spread requires an application of clustering rules, it may be more appropriate to treat spread separately.

As will be discussed in the context of the control of treatment therapy, external system 100 may use detection clustering for purposes of delivery and a termination of stimulation or restimulation.

External system 100 may use information about detection clusters in order to identify circadian or other seizure trends. (Other embodiments of the invention may support other systems for treatment of a nervous system disorder, e.g., hybrid system 1000 and implanted system 10.) External system 100 may determine whether seizure-related activity occurs at specific times of the day (e.g., morning, afternoon, or night, and/or at drug administration times) or, in the embodiment of an implanted system, month (e.g., menstrual cycle). Also, external system 100 may determine whether there is a cyclical pattern that is associated with a patient's seizures as measured by alternating periods of seizure-dense and seizure-free time intervals. External system 100 may identify specific times when intense seizure activity (e.g., seizure clustering) significantly deviates from the patient's mean or median seizure frequency (i.e., what the patient perceives are clinical seizures only). External system 100 may produce a seizure trending report that identifies whether a trend in seizure activity is present, along with graphical and summary information.

External system 100 may use information about detection clusters in order to provide measures of an event burden. The event burden may be determined by different criteria such as event frequency (a number of neurological events that a patient is experiencing during a unit of time), number of detection clusters per unit time, detection cluster severity (a conjoint measure of the cluster intensity, the cluster duration, and the extent of electrographic spread), and an event severity (as determined by a patient's classification of seizure severity as inputted into external system 100 or ratio).

External system 100 may adjust therapy parameters, e.g., stimulation parameters or drug infusion parameters, in order to adjust to the effectiveness of the treatment. The embodiment supports both intra-cluster staging and inter-cluster staging. With intra-cluster staging, external system 100 may automatically adjust a therapy parameter (e.g., the stimulation voltage or amperage) with each successive administration of stimulation within a detection cluster until the seizure is terminated. The therapy parameter may be a member of a predefined set of parameters. At least one predefined set of parameters may be configured during trial screening subprocess 2151. External system 100 may also automatically adjust therapy parameters with each successive administration of clustered therapy (i.e., administration or withholding of therapy based on a cluster). Inter-cluster adjustment may occur at every $n^{th}$ detection cluster or according to a cluster sequence pattern (e.g., adjusting therapy parameters only on the second and seventh subsequent detection clusters). The user may define the cluster sequence pattern using the programmer 109. With both intra-cluster staging and inter-cluster staging, a predefined threshold may be established (such as by the user through programmer 109) that limits the adjustment of a therapy parameter.

External system 100 keeps track of seizure severity measures such as intensity, duration, and electrographic spread using measures of central tendency or other suitable measures and ranks all detections as a function of intensity, duration, etc, and also as a function of the temporal evolution of these variables "within a detection cluster" and "between detection clusters". External system 100 also sorts seizures according to time of day, day of week, week of month, month of year and also year, using the same variables described above and also according to their temporal evolution within and between clusters. Using these data, external system 100 creates another rank to track circadian, ultradian and other rhythms and features. If any detection severity measure exceeds a certain level, but remains below another level, e.g., the 99% tile, one or more therapeutic parameters are increased, by a predetermined amount that may vary intra-individually (according to the subjects seizure statistics) and inter-individually. The number and sequence in which parameters would be increased is also prespecified intra- and inter-individually. If the pre-specified type of and sequence of parameter changes are not efficacious, search methods, e.g., a random search method, may be used to select more efficacious therapy parameter values, the number of therapy parameters increased at one given time and the order in which they are increased. External system 100 is programmed not to accept stimulation parameter values that exceed a pre-specified current density or the toleration limits as determined in step 1961.

If one or more measures of seizure activity exceed a predetermined limit at any point in time, e.g., the 99% tile value of preceding detections, the event may be an indication that therapy may have a paradoxical effect. In such cases, one or more of the therapy parameters may be decreased or the external system 100 may be shut down (temporarily) while gathering more data to reassess the situation. (In the embodiment, determining whether to reassess therapy parameters may occur at any time during the treatment therapy.) The amount of time that therapy parameters can be modified may be based on endpoints such as quality of life and/or statistical analysis of the data.

External system 100 may be capable of changing geometry or configuration of stimulation including the number of contacts, as well as the anode and cathode location. For instance, if stimulation is being delivered to contacts 1 and 3 without good results, external system may add contact 2 or change to contacts 1 and 4. In addition, stimulation may be limited to the contacts where an event was detected. These decisions are made using an ability of external system 100 to quantify detection intensity, duration, etc., at each contact and on the history of values at each contact. Also, since direction of current flow may determine the response to electrical stimulation, the anode and cathode may be reversed. Or to increase the size of the negative field, the anode may be shifted to a reference electrode of lower impedance (due to larger surface area such as one of the surfaces of the case containing the stimulation engine). External system 100 has the capability of estimating current density at any contact site. Contacts for measuring current density may also be placed at certain sites at a distance from where stimulation is being delivered, in a grid or some other pattern to better assess safety and efficacy, by obtaining a more realistic estimate than the one that is routinely obtained at the contact-brain interface.

The embodiment has described monitoring elements taking the form of electrodes sensing electrical activity associated with brain ECoG. Other embodiments of the monitoring element adapted to sense an attribute of a Nervous System Disorder could be used. Alternatively, the monitoring element could detect abnormal concentrations of chemical substances in one location of the brain. Yet another form of the monitoring element would include a device capable of detecting nerve compound action potentials. The monitoring element also may take the form of a device capable of detecting nerve cell or axon activity that is related to the pathways at the cause of the symptom, or that reflects sensations that are elicited by the symptom. The monitoring element may take the form of a transducer consisting of an electrode capable of directly measuring the amount of a particular transmitter substance or its breakdown by-products found in the interstitial space of the central nervous system. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horn, Spencer Bement, Barry J. Hoffer, and Greg A. Gerhardt, published in Neuroscience Letters, 120 (1990) 249–252.

The monitoring element may be external to the body communicating with the implanted portions through telemetry. An example of an external monitoring element is an electrical device that includes an electrode attached to the surface of the skin that passes a small current to measure the skin impedance. An example of this type of the monitoring element is described in the paper "Skin Impedance in Relation to Pain Threshold Testing by Electrical Means", by Emily E. Meuller, Robert Loeffel and Sedgwick Mead, published in J. Applied Physiology 5, 746–752, 1953. A decrease in skin impedance may indicate an increase in anxiety. Other monitoring elements such as Carbon dioxide gas sensors or other sensors that can detect the physiological parameters such as those listed above will be clear to those skilled in the art.

Control of Treatment Therapy During Start-Up and During Operation

In an embodiment, any one of the above-described medical device systems may limit delivery of therapy during start-up and during operation for improved efficacy. During start-up, the medical device system may be programmed to only monitor neurological signals (no delivery of treatment therapy) for a predetermined time period (e.g., 30 minutes) after the medical device system is turned on. Of course, the time period is a function of the background window length and may vary in duration. During this start-up period, the medical device system may collect data and allow the seizure detection algorithm system described above to stabilize and adjust to data from the individual and set of signals being monitored in order establish a background and avoid potential for erroneous detections (and unwanted administration of therapy) before such information has been acquired. It has been determined that during the period of algorithm stabilization, the probability of false positive detections is high. Thus, by programming the medical device system to not provide treatment therapy during this period, unnecessary treatment therapies can be avoided.

To illustrate how the treatment therapy can be limited during start-up, the embodiment of an external system 100 is described. The external system 100 monitors electrical brain activity in the patient and collects data on eight electrodes (each with respect to a common reference or in a "differential" manner) preferably at 250 Hz sampling rate. This collected data is transferred to the DSP chip (where the detection algorithm resides) in blocks of 96 bytes, which is 8 channels multiplied by 12 data points per channel, and occurs at a fixed rate (48 milliseconds). Time in the external system 100 can therefore be measured in block counts. The external system 100 starts counting blocks from the start of a session, and uses them for numerous purposes, such as controlling the stimulation board (found, for example, in the stimulation electronics module 203 of the bedside device 107).

Software methods within the external system 100 provide the functionality being described. In particular, software of the external system 100 engages an authorize stimulation subroutine that checks for numerous conditions to make sure they are all valid before authorizing stimulation. Software within the external system 100 also has a lockout parameter that is checked by the authorize stimulation routine to make sure that enough blocks have passed to correspond to the startup time before it will allow stimulation. The default value that is used is 37,500, which corresponds to 30 minutes. After this period, the lockout is released and no longer prevents stimulation. Any seizure detections prior to this period that would otherwise result in stimulations may thereby be prevented. The time period during which the medical device system only monitors and delivers no treatment therapy may be established by techniques other than block counts. For example, the time period may be established such that a set quantity of information has been obtained from the monitoring elements.

As discussed, the functionalities of the present invention may be implemented in other embodiments. In the embodiment of a hybrid control system, the aforementioned software methods may be implemented within either the implantable device 953 or the external wearable device 1000 (see FIG. 9). In the embodiment of a fully implanted control system, the aforementioned software methods may be implemented within the implanted device.

During its operation, the medical device system may also invoke any number of methods for limiting therapy during operation if it would result in therapy being outside of the acceptable range for one or more therapy parameters. For example, in the embodiment of the external system 100, the system 100 may limit the total number of stimulations delivered for a variety of reasons including, but not limited to, programming checks and lockouts, tissue damage, and run time monitoring and control. During programming of the external system 100, the programmer software checks the programming information to make sure that the stimulation board (e.g., Synergy®) never provides a charge density above a predetermined limit (e.g., 30 uC/cm²/phase). In particular, the programmer software performs calculations based on the geometry of the lead being used and the attempted setting entered by the user. If this predetermined limit is exceeded, a message informs or warns the user/clinician and prevents the parameters from being sent to the stimulation board.

The programmer 109 may also limit the stimulation ON time that is allowed to be programmed into the external system 100 by calculating parameters that will be used during run time to control the stimulation ON time. Parameters include, for example and without limitation, a maximum number of stimulations per detection, a maximum number of stimulations per cluster, a maximum stimulation ON time during a one-hour period, and a maximum stimulation ON time during a one-day period. Depending on the embodiment, these parameters may be fixed in the software or programmable so that they may be adjusted by the physician or a qualified user.

Although the aforementioned functionality is described as existing in programmer 109, in other embodiments such as a hybrid control system or a fully implanted system, the functionality may reside in a physician or patient programmer (or in the implanted device or the hybrid system).

Again, it will be appreciated that other embodiments are possible including medical device systems providing other treatment therapies as well as systems that monitor other symptoms or conditions of a nervous system disorder. In the embodiment, the amplitude level may be adjusted between 0 and 20 volts; pulse widths may be adjusted between 20 microseconds to 5 milliseconds, and the pulse frequency may be adjusted within 2 pps and 8,000 pps, in which the wave forms may be pulsed, symmetrical biphasic, or asymmetrical biphasic.

Timed Delay for Redelivery of Treatment Therapy

The medical device system may repeatedly administer treatment therapy during a detection, until the symptom or condition of the nervous system disorder has been terminated. For clarity, the following discussion is provided in the context of the external system 100, although other embodiments are possible (e.g., the hybrid system). In the discussion, a neurological signal may be an EEG signal that is sensed by one or more monitoring electrodes. However, in other embodiments of the invention, a neurological signal may be provided using other types of monitoring elements such as other types of sensors. Treatment therapies may include any number of possibilities alone or in combination including, for example, electrical stimulation, magnetic stimulation, drug infusion, and/or brain temperature control. The redelivery of stimulation is controlled by a programmable minimum interstimulus interval (min ISI). The minimum interstimulus interval begins each time the medical device system terminates stimulation, and ends after the specified amount of time. During the interstimulus interval, the device is not able to turn on stimulation.

Figure 23:
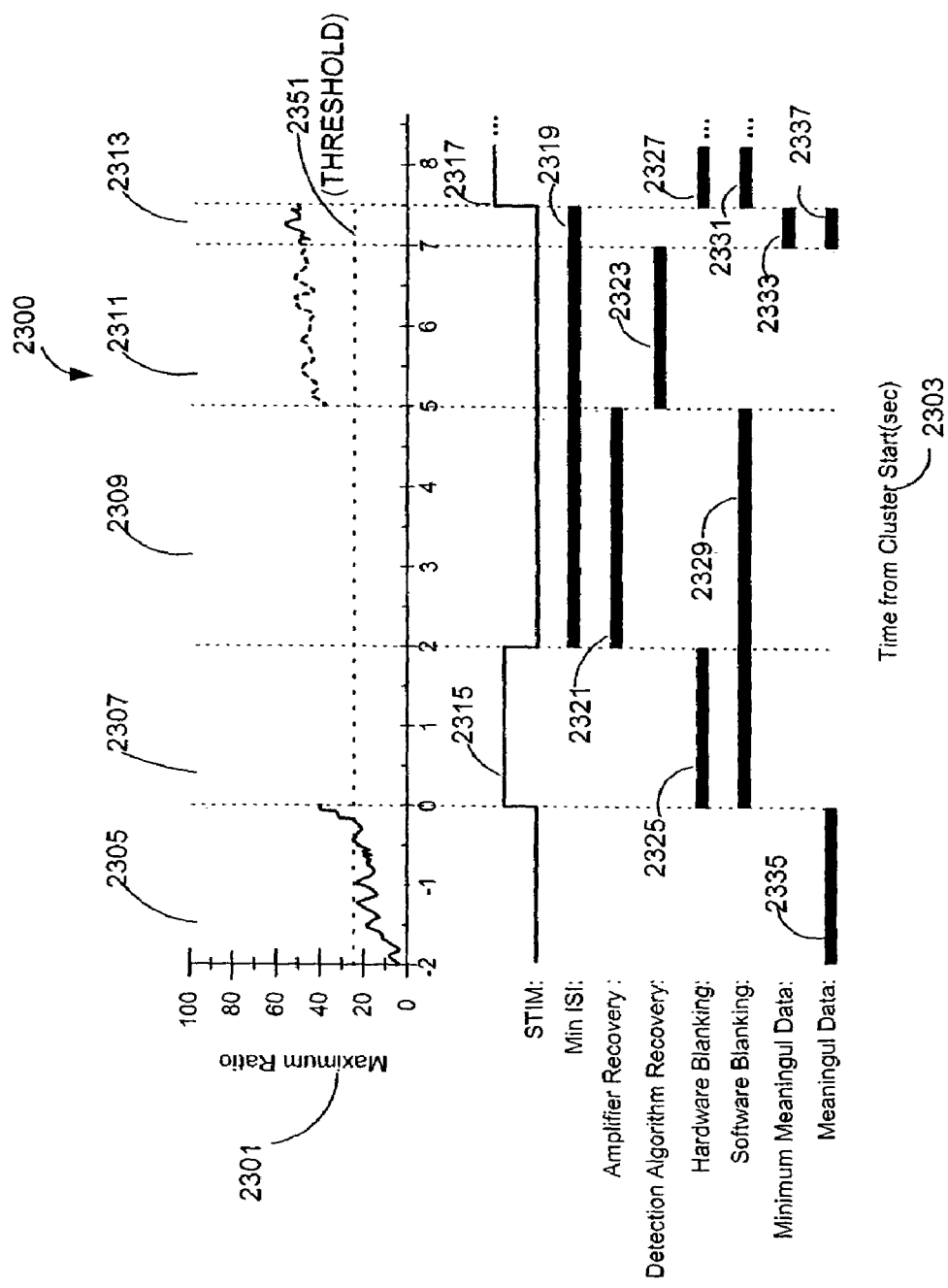
FIG. 23 shows a timing diagram including the seizure detection algorithm processed maximal ratio signal.

FIG. 23 shows a timing diagram including the seizure detection algorithm processed maximal ratio signal. As shown, EEG signal data 2300 are processed by seizure detection algorithm 800. Signal data 2300 is characterized by a maximal ratio 2301 that is displayed as a function of a time reference 2303 (which is relative to a detection cluster start time in seconds). (Maximal ratio is discussed in the context of FIG. 22. The maximal ratio is the largest ratio of a set of ratios, in which each ratio is determined by a short-term value of a neurological signal divided by the corresponding long-term value.)

Signal data 2300 comprises signal segments 2305, 2307, 2309, 2311, and 2313. During segment 2305, signal data 2300 is collected, processed, and tracked by the medical device system (e.g., external system 100) in order to determine if a seizure is occurring. As a result of the seizure detection at the end of interval 2305, issued by the seizure detection algorithm's analysis of input signal data 2300 during time interval 2335, the medical device delivers an electrical stimulation pulse 2315 to a desired set of electrodes (e.g., electrodes 101). Other embodiments of the invention, of course, may use other forms of therapeutic treatment discussed above.

During stimulation pulse 2315, a corresponding channel is blanked by hardware during a hardware blanking interval 2325 (approximately two seconds in the example as shown in FIG. 23) so that no signal is collected or analyzed during this interval of time. Additionally, meaningful data typically cannot be collected after stimulation pulse 2315 for a period of time because associated amplifiers (e.g., amplifier 1111) need to stabilize and because signal artifacts may occur between electrodes during a amplifier recovery interval 2321 (approximately three seconds as shown in FIG. 23).

A software blanking interval 2329 (approximately five seconds as shown in FIG. 23) is equal to hardware interval 2325 plus amplifier/signal recovery interval 2321. During software blanking interval 2329, the medical device system does not use signal data 2300 during segment 2307 (corresponding to hardware blanking interval 2325) and segment 2309 (corresponding to amplifier recovery interval 2321). In other embodiments, the medical device system may not collect signal data 2300 during software blanking interval 2329. (In the embodiment, software blanking may occur on a subset of all channels, including channels not being stimulated. Also, the set of channels that are software blanked may be different from the set of channels that are hardware blanked.)

In the embodiment, hardware blanking interval 2325 and software blanking interval 2329 may be predetermined, in which intervals 2325 and 2329 may be programmable or non-programmable. Hardware blanking interval 2325 may correspond to blanking of software or blanking of hardware, and software blanking interval 2329 may correspond to blanking of hardware or blanking of software.

After software blanking interval 2329 (the end of interval 2329 coincides with the end of amplifier recovery interval 2321), the medical device system resumes analyzing signal data 2300 using seizure detection algorithm 800 during recovery interval 2323 (and produces output ratio corresponding to segment 2311 in FIG. 23). The recovery interval 2323 allows time to ensure that subsequent analysis output is able to meaningfully represent the post-treatment brain state. Since, in the embodiment, seizure detection algorithm 800 utilizes a two-second foreground window, the algorithm recovery interval 2323 is approximately two seconds. The medical device system may then use this meaningfully representative detection algorithm output in a subsequent interval 2333 in order to determine whether treatment therapy was effective or if the seizure is continuing. This subsequent interval may be an instant in time (i.e., one data point), or may be extended to acquire sufficient meaningful data to permit a statistical analysis of the efficacy of the therapy. This information may be used to determine whether or not to redeliver treatment therapy.

In the embodiment, the medical device collects a minimum amount of meaningful data (corresponding to segment 2313) during a minimum meaningful data interval 2333. This enables statistical analysis of the efficacy of the therapy. The minimum interstimulus interval is equal to amplifier recovery interval 2321 plus detection algorithm recovery interval 2323 plus minimum meaningful data interval 2333. If the maximal ratio 2301 remains at or above a predetermined threshold 2351, then the medical device system re-applies an electrical stimulation pulse 2317 to the desired set of electrodes. If instead, the maximal ratio is below the predetermined threshold 2351, the medical device system continues to monitor signal data 2300. An electrical stimulation or other form of therapy may be applied if a subsequent seizure detection is made by the medical device system, indicating a continuation of the seizure detection cluster.

In the embodiment, during the combined periods of algorithm recovery interval 2323 and minimum meaningful data interval 2333 (corresponding to a total time of approximately 2.5 seconds), the detection algorithm's maximum ratio 2301 is monitored to determine if the subject is in a state of seizure or not. Two different scenarios are possible, in which different rules are employed for each case to decide whether restimulation should occur. If the algorithm's maximum ratio 2301 exceeds the predetermined threshold 2351 for the entire period (i.e., interval 2323 plus interval 2333), stimulation will be re-administered. Onset of stimulation will occur at the end of the minimum interstimulus interval. In such a case, the algorithm's duration constraint (time duration), which in the embodiment is approximately equal to 0.84 seconds, is not evaluated, since the subject is still in a state of seizure detection. However, if the algorithm's maximum ratio 2301 drops below the predetermined threshold 2351 during this period, the seizure detection ends. Stimulation will not be administered until the next seizure detection within the detection cluster. This requires that the algorithm's threshold and duration constraints are both satisfied (i.e., maximum ratio 2301 is as great as the predetermined threshold 2351 for the duration constraint).

The process of restimulation will occur as long as the subject remains in a state of seizure, and that pre-programmed stimulation safety limits have not been reached.

The number of allowable stimulations per detection cluster is a function of the stimulation duration and the stimulation limits. For example, in the embodiment, a stimulation duration of 2 seconds would result in a maximum of 5 stimulations in a single seizure detection, and a maximum of 10 for the entire detection cluster. However, the clinician may program the number of allowable stimulations per detection cluster in order to adjust treatment therapy for the patient. If the subject remains in a non-seizure state for a period of 1 minute, the cluster ends. Determination of whether stimulation will be triggered for the next detection cluster is determined by a programmed stimulation sequence.

Cycle Mode Providing Redundant Back-Up to Ensure Termination of Treatment Therapy The medical device system may provide a cycle mode of operation to serve as a redundant backup to ensure that therapy is stopped after a predetermined time period. In an embodiment, this functionality is provided within an implanted therapy device such as an implantable pulse generator or a drug infusion device. In the embodiment of providing electrical stimulation treatment therapy, for example, the cycle mode of operation may be provided in a stimulation board (e.g., the stimulation output circuit that is used in the Synergy® product sold by Medtronic, Inc.), which is typically within the implantable pulse generator. In the specific embodiment of the external system 100, the stimulation board may reside in the stimulation electronics module 203 of the bedside device 107. In general, the stimulation board of the medical device system provides continuous stimulation where stimulation is turned on and remains on until it is explicitly turned OFF. A programmer or an external device, for example, may provide the necessary ON or OFF commands to the stimulation board.

The stimulation board has a cycle mode, having a defined ON time, to act as a redundant back-up in case the stimulation board does not receive the necessary command to turn OFF the stimulation therapy. The ON time may be predefined or may be programmable by a treating physician or qualified user. More particularly, when the stimulation board receives an ON command, the stimulation board cycles ON and delivers stimulation. The stimulation board then eventually receives an OFF command to turn off the stimulation. If the medical device system, however, should happen to fail during stimulation and be unable to supply the OFF command, the cycle mode acts as a redundant backup to make sure that stimulation turns off after the ON timer has expired.

Figure 24:
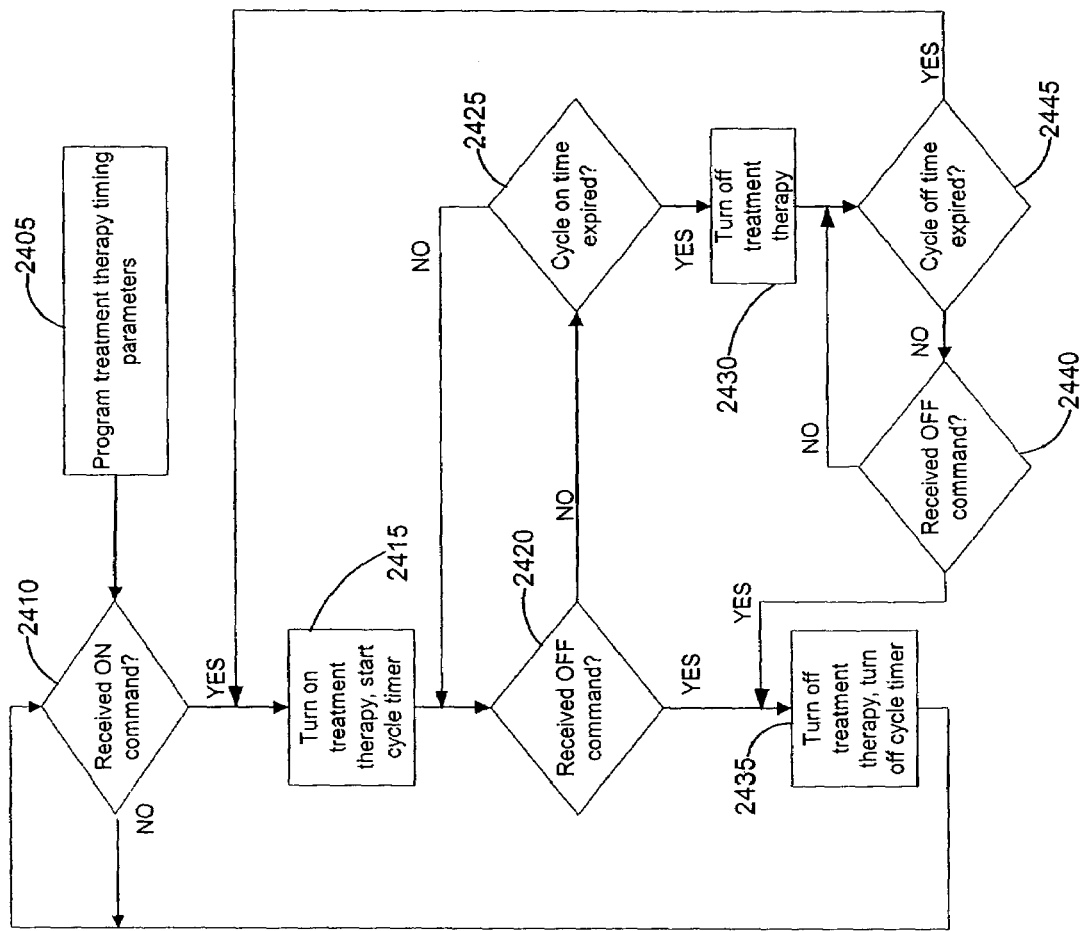
FIG. 24 is a flow diagram illustrating the process for implementing a cycle mode of operation within generally any medical device system.

FIG. 24 is a flow chart illustrating a process for implementing a cycle mode of operation within generally any medical device system. The process may be implemented as logic circuitry or firmware in the medical device system. At step 2405, the medical device system receives therapy parameters for the treatment therapy. For example, in the case of a stimulation device, the treatment therapy parameters may include electrode identification, pulse width, pulse frequency, and pulse amplitude. The information may be received by the electronics component responsible for providing the electrical stimulation. In the external system 100, it may be the stimulation electronics module 203. In the hybrid system 1000, it may be the implantable device 1100. At step 2410, the medical device system waits until it receives an ON command. Once an ON command is received, at step 2415, the medical device system starts a cycle timer ON and starts delivering the treatment therapy in accordance with the previously-received treatment therapy parameters. Once again, the cycle ON timer may be predefined or may be programmable by a treating physician or qualified user. The medical device system continues to deliver treatment therapy and checks whether it received an OFF command, at step 2420, and whether the cycle ON timer has expired, at step 2425. Again, the cycle ON timer may be pre-configured to any duration or may be programmed by the treating physician. Under normal operation, once an OFF command is received, at step 2435, the medical device system turns off the treatment therapy and turns off the cycle ON timer. The system then returns to step 2410 to start the process over once another ON command is received.

If, on the other hand, the system does not receive the OFF command, but the cycle ON timer has expired, at step 2430, the system turns off the treatment therapy and activates a cycle OFF timer. During the cycle OFF time, the system is unable to provide treatment therapy. This provides an indication to the patient or the physician that the redundant cycle mode was activated due to failure in receiving an OFF command. The cycle OFF timer is typically pre-configured to a predetermined maximum time duration to give the physician time to notice that the medical device system is not functioning as expected. (As an example, an embodiment sets the cycle OFF timer to approximately 32 hours.)

The system next waits until either the cycle OFF timer has expired, at step 2445, or until the system has received an OFF command, at step 2440. The "YES" branch from step 2445 to step 2415 is not typically executed because the cycle OFF time should give the physician time to notice system failure and to intervene accordingly.

Phase Shifting of Neurological Signals

In the present invention, multiple neurological signals may be processed for information about a symptom or a condition of a nervous system disorder. Successful detection of a disorder is dependent on the temporal integrity of the signals relative to one another. Consequently, once the neurological signals are sampled, they may become virtually shifted in time by interpolating between adjacent samples. Temporal alignment can be approximated using an interpolation phase shift algorithm, thereby correcting any error caused by the time shifted neurological signals. This technique may be implemented within a closed-loop medical device system or a medical device system having only monitoring.

Given N channels of data that are sampled at different points in time, interpolation techniques may be utilized to obtain estimates of true time-locked signal values on all channels at a sequence of time points. Essentially, the interpolation techniques reconstruct an estimate of what the data would have been if all channels had been simultaneously sampled, even though they were not.

In order to accomplish this, an interpolating model is selected for use in determining signal estimates at time points between those for which digitization was actually performed. The particular interpolating function, in general, may depend on data values received up to the moment in time it is evaluated. One channel is selected, typically channel #1, whose sampling times are used as a temporal reference. Estimates of the values on all other channels may then be computed relative to the temporal reference. Knowing the elapsed time between digitization of the reference channel and that of any other channel, a channel-dependent time-shift, $\Delta t_j$, may be obtained that represents the time difference between the sampling times on channel j and the corresponding reference times at which the estimates are desired.

In the preferred embodiment, the interpolating model is a third degree polynomial that is fit (i.e., defined by) the most recent four data points on each signal channel. One skilled in the art will appreciate that other interpolating models, e.g., lower or higher degree polynomials, may also be used, depending on such things as spectral properties of the raw signal being interpolated and computational complexity or power requirements of the device processor.

In the preferred embodiment, the phase-corrected corrected signal has been implemented in the computationally efficient form of a channel-dependent finite impulse response digital filter applied to the raw data obtained for each channel. More specifically, if the sequence of raw data on channel j is denoted by $X_1^j, X_2^j, X_3^j, \ldots, X_{k-2}^j, X_{k-1}^j, X_k^j$, then the interpolated output, $Y_k^j$, at time sequence point k and on channel j is obtained via the formula:

$$Y_k^j = \sum_{i=0}^{3} b_i X_{k-i}^j$$

where $$b_0 = \frac{C_j^3}{6} - \frac{C_j^2}{2} + \frac{C_j}{3},$$

$$b_1 = \frac{C_j^3}{2} + 2C_j^2 - \frac{3C_j}{2},$$

$$b_2 = \frac{C_j^3}{2} - \frac{5C_j^2}{2} + 3C_j,$$

$$b_3 = -\frac{C_j^3}{6} + C_j^2 - \frac{11C_j}{6} + 1, \text{ and}$$

$$C_j = \frac{25 - j}{8}.$$

Figure 25:
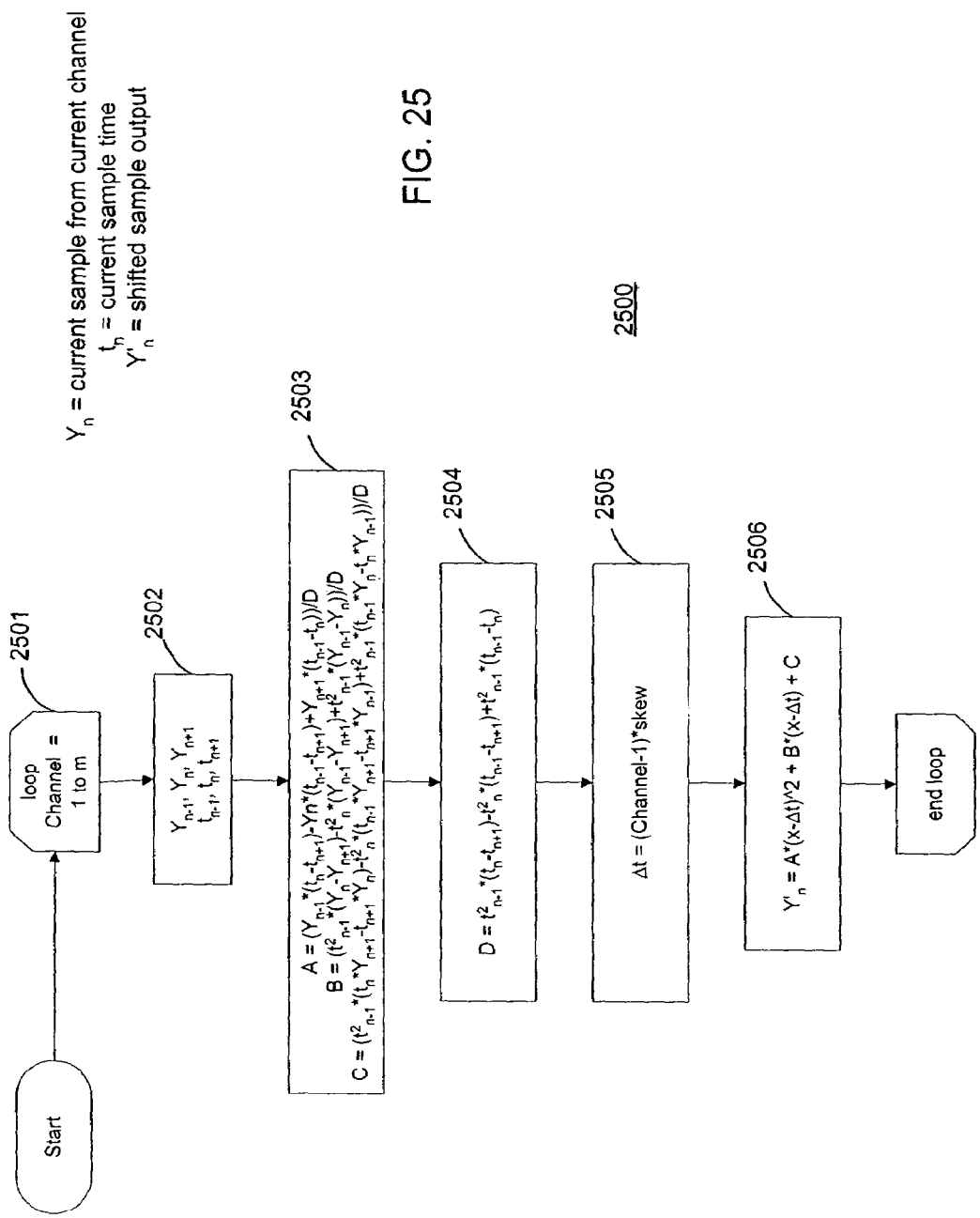
FIG. 25 is a flow diagram for phase shifting in accordance with an embodiment of the invention where the nervous system disorder being treated is a seizure.

FIG. 25 shows a flow diagram 2500 for phase shifting in accordance with another exemplary embodiment based on a polynomial interpolation model (e.g., parabolic, linear, cubic, etc.). Step 2501 initiates phase shifting for one the received neurological signals or channels relative to a first neurological signal, which is treated as a reference signal. In step 2502, signal samples for the received neurological signal are collected corresponding to the current sample time and the two previous sample times. In steps 2503 and 2504, unknown variables for the interpolation equation are calculated. In step 2505, a delta time shift is computed for the current channel. In step 2506, the shifted sample output is computed by solving the polynomial curve fit equation at the delta time shift. The received neurological signal may thereby be corrected by shifting the signal samples in time by an amount determined in step 2506 so the neurological signal is synchronized with the default neurological signal. This process may then be repeated for each received neurological signal. The time-shifted neurological signals and the default signal may thereby be utilized to provide closed-loop feedback control of the treatment therapy.

Figure 26:
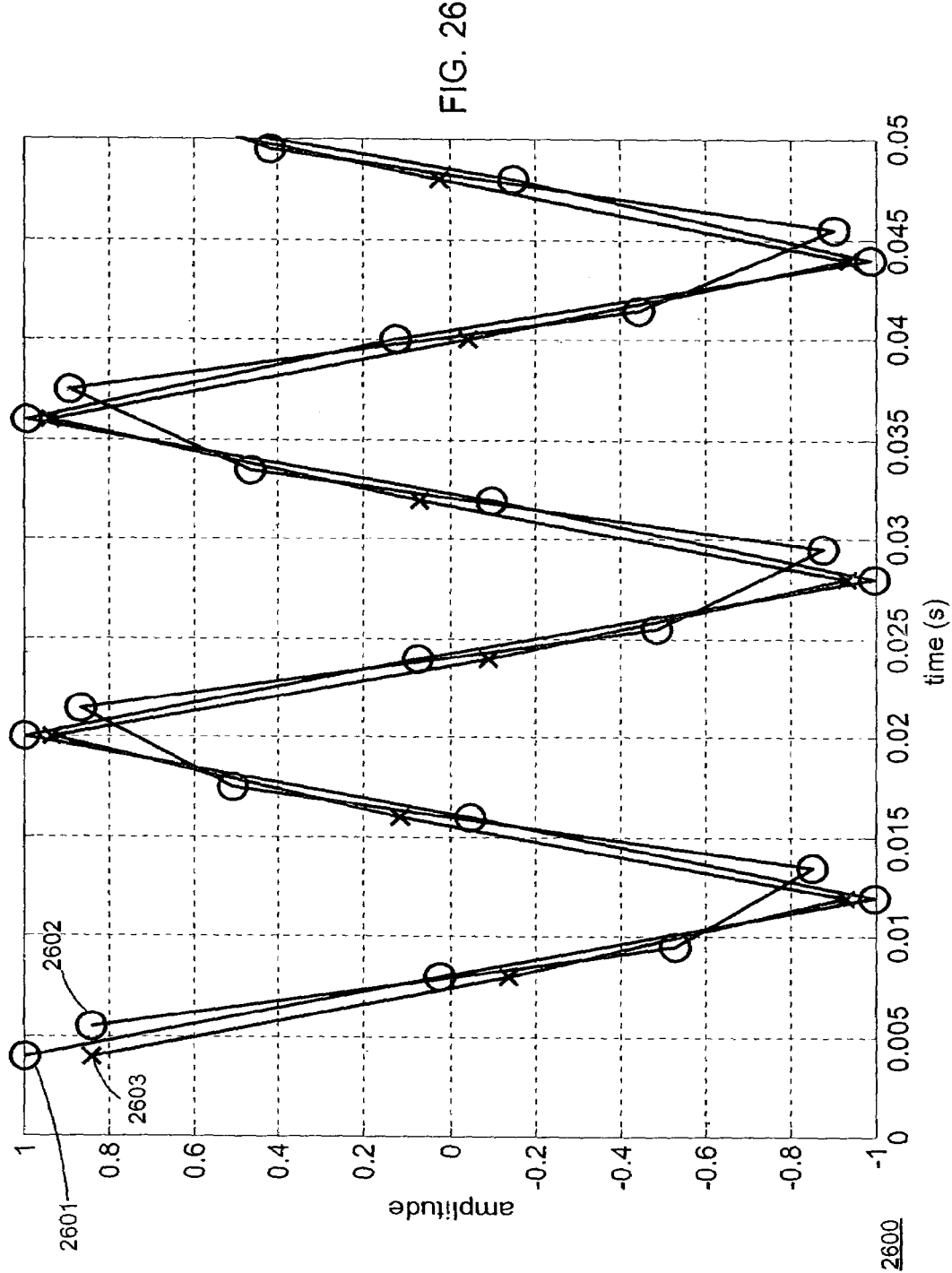
FIG. 26 is a graph of a result of applying the polynomial interpolation phase shift algorithm.

FIG. 26 illustrates an example of applying a parabolic interpolation phase shift algorithm. In this example, a simple sine wave signal from channel 1 is sampled, indicated by 2601, and treated as a reference signal. A second channel is sequentially sampled and experiences a shift in time, as indicated by 2602. Signal 2603 shows the second signal corrected for the time shift after the phase shift algorithm is applied. In one embodiment, sequential samples from a given channel is used to generate a parabolic curve to "interpolate" what the actual value would have been had they sampled it at the correct time (all channels sampled in parallel). The accuracy may be improved by using other interpolation function models, including higher order polynomials. In another embodiment, data samples themselves may be shifted.

Those skilled in the art will appreciate that other phase shifting algorithms may be utilized including, in particular, other formulas for determining the amount of time shifting. Moreover, although described in the context where nervous system disorder being treated is a seizure, the principles of the invention may be applied toward treatment of other nervous system disorders, and may be utilized to process any number of neurological signals.

Channel-Selective Blanking

In accordance with another feature of the present invention, any one of the above-described medical device systems may be configured so that it may provide hardware and software blanking functionality. In particular, the medical device system may invoke either hardware blanking and/or software blanking of a received neurological signal if the system should not process the signal for the corresponding monitoring element. In the embodiment of the external system 100, for example, hardware blanking (through blanking circuitry 401) corresponds to the system disconnecting the EEG amplifier 103 from the channel that is being stimulated by stimulation electronics 203 through the associated electrode during a time interval that includes the stimulation delivery period. (In the embodiment, amplifier 103 is disconnected from the associated electrode and connected to a reference voltage.) Because no data is being collected during stimulation, no data (for the corresponding channel) is sent to the processor 207 to be processed by the detection algorithm 800 at the associated time. Data may, however, be collected on other channels that are not being stimulated and processed at an associated time.

In addition, the medical device system may invoke software blanking in which data from a neurological signal is collected for a particular channel, but the medical device system determines that data should not be processed during a time interval (e.g., for use with the detection algorithm discussed above). For example, if hardware blanking is invoked for certain channels, the medical device system may invoke software blanking on those and/or on any electrode (i.e., on different channels) where a stimulation artifact may occur. (For example, stimulating an electrode may cause adjacent electrodes to incur stimulation artifacts.) As another example, software blanking may be invoked if the EEG amplifier 103 is recovering after the termination of stimulation on at least one channel.

Figure 27:
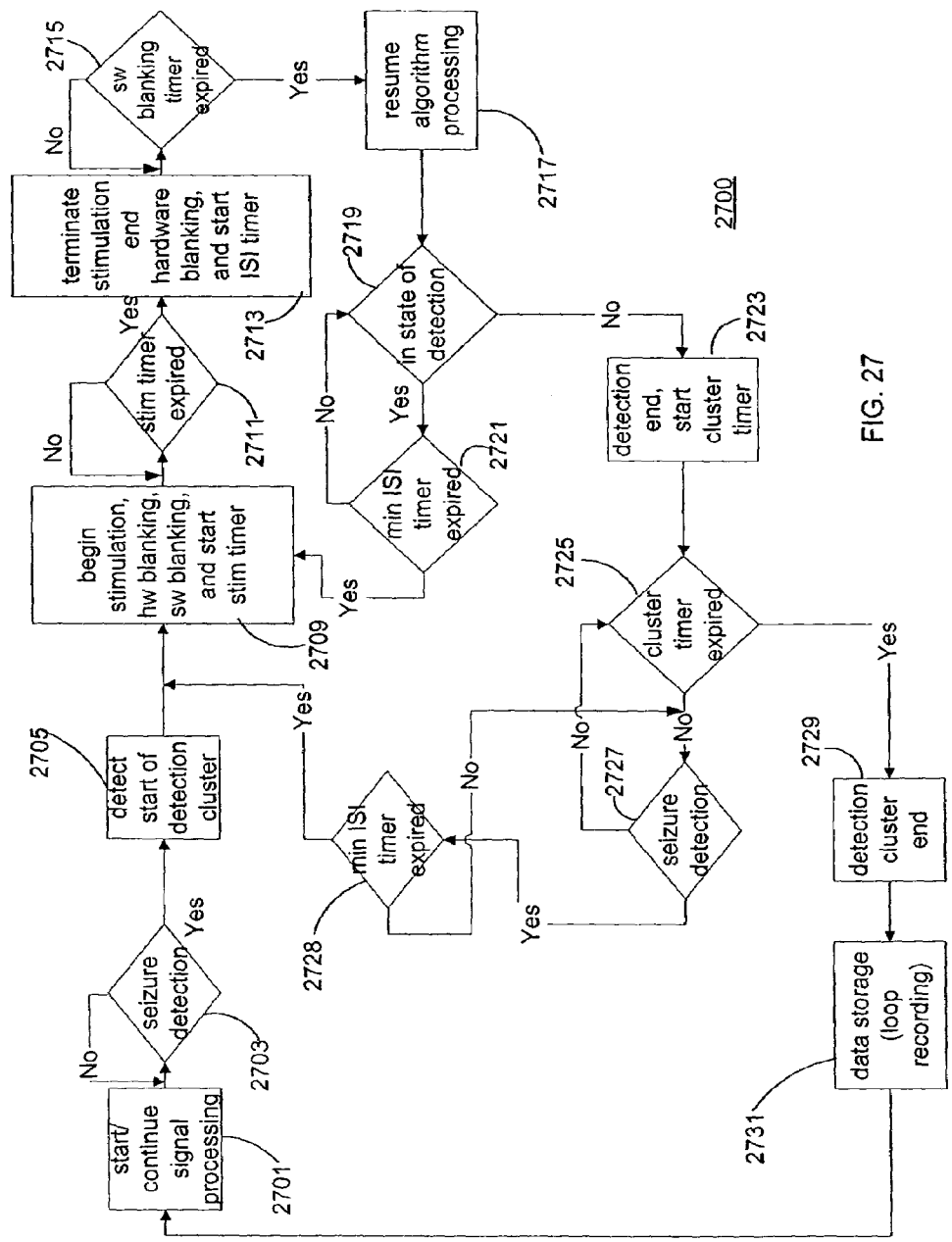
FIG. 27 is a flow diagram for hardware and software blanking.
Figure 28:
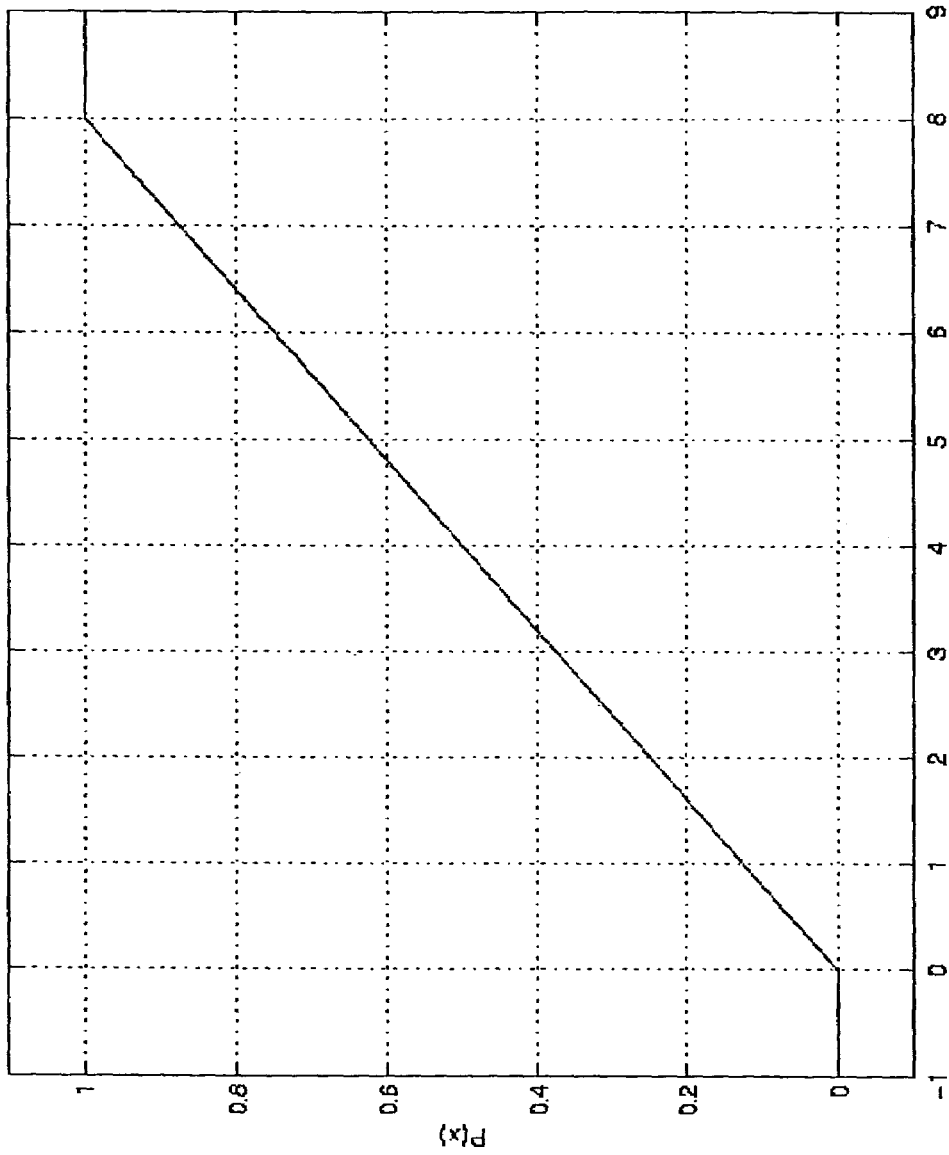
Figure 29:
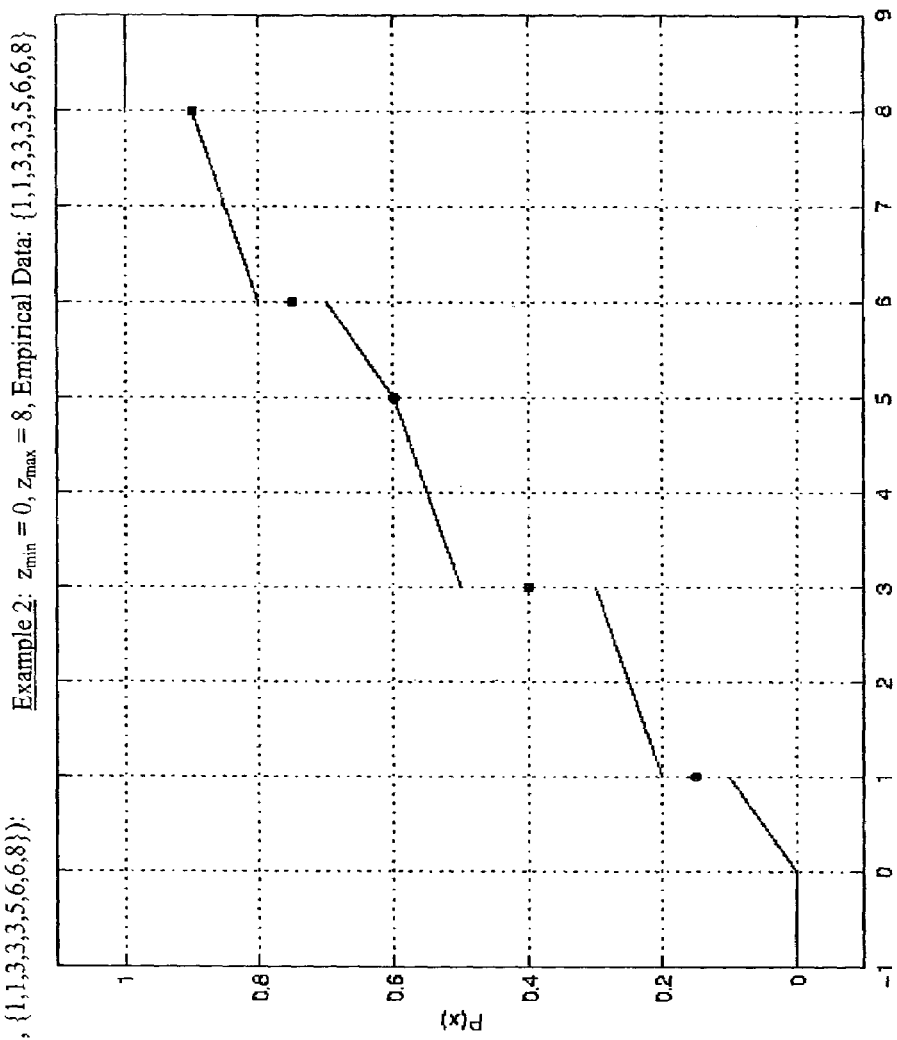
Figure 30:
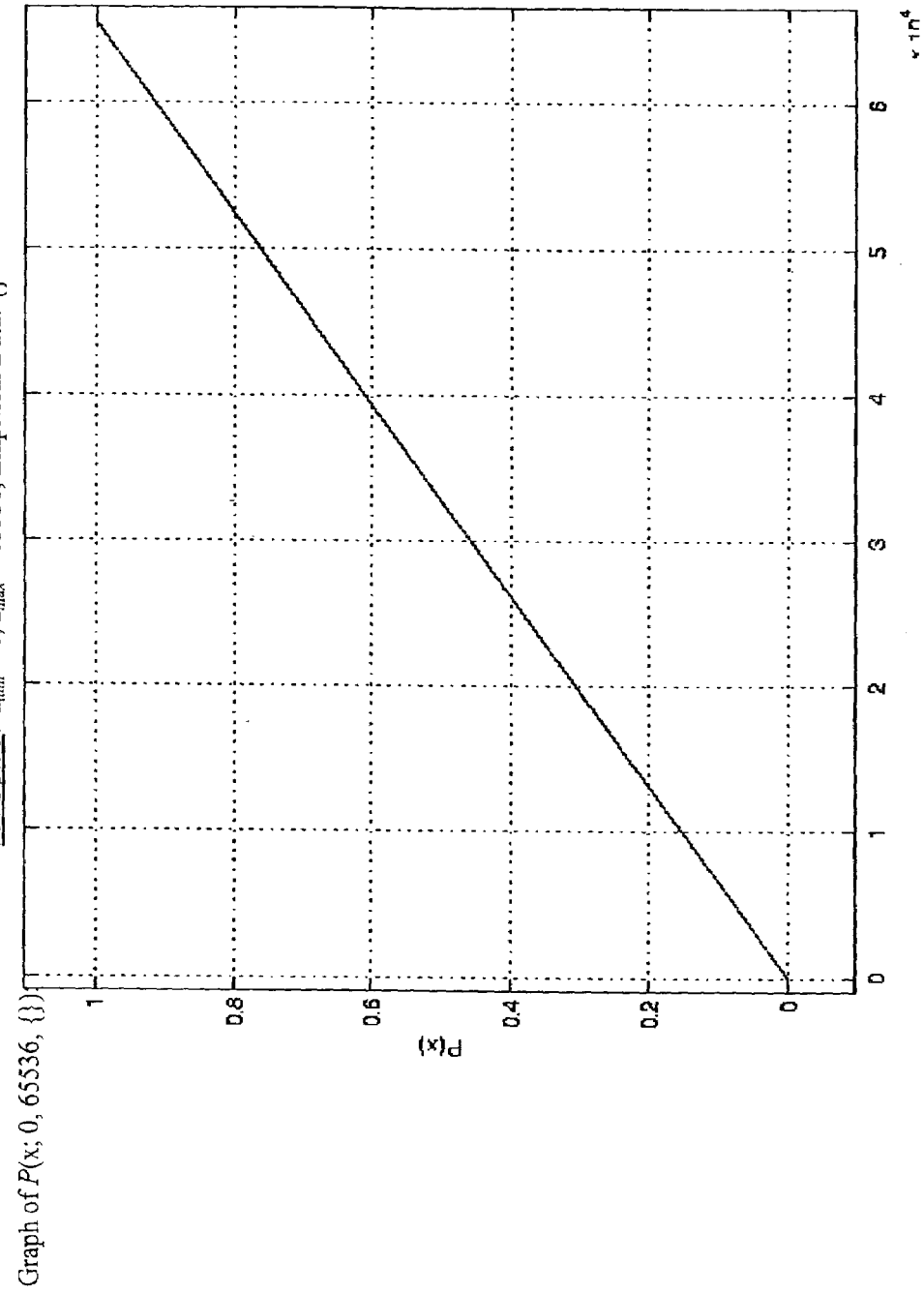
Figure 31:
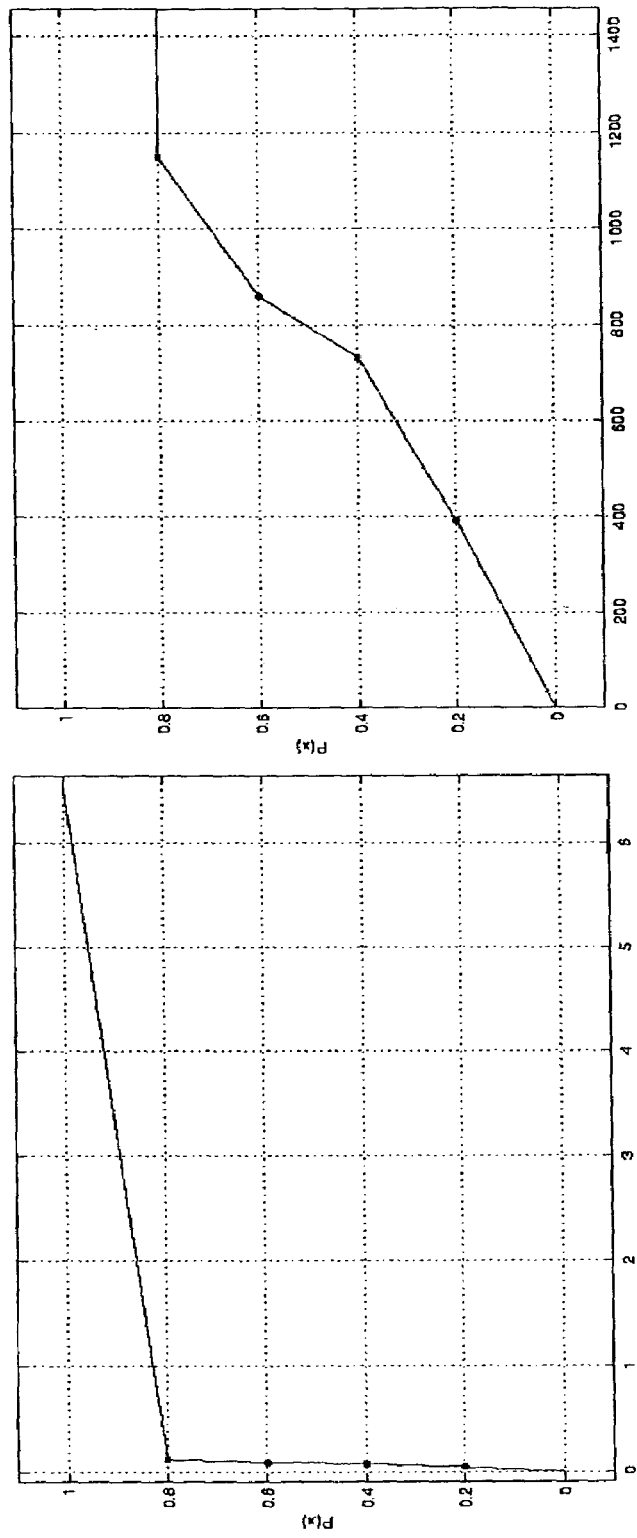
Figure 32:
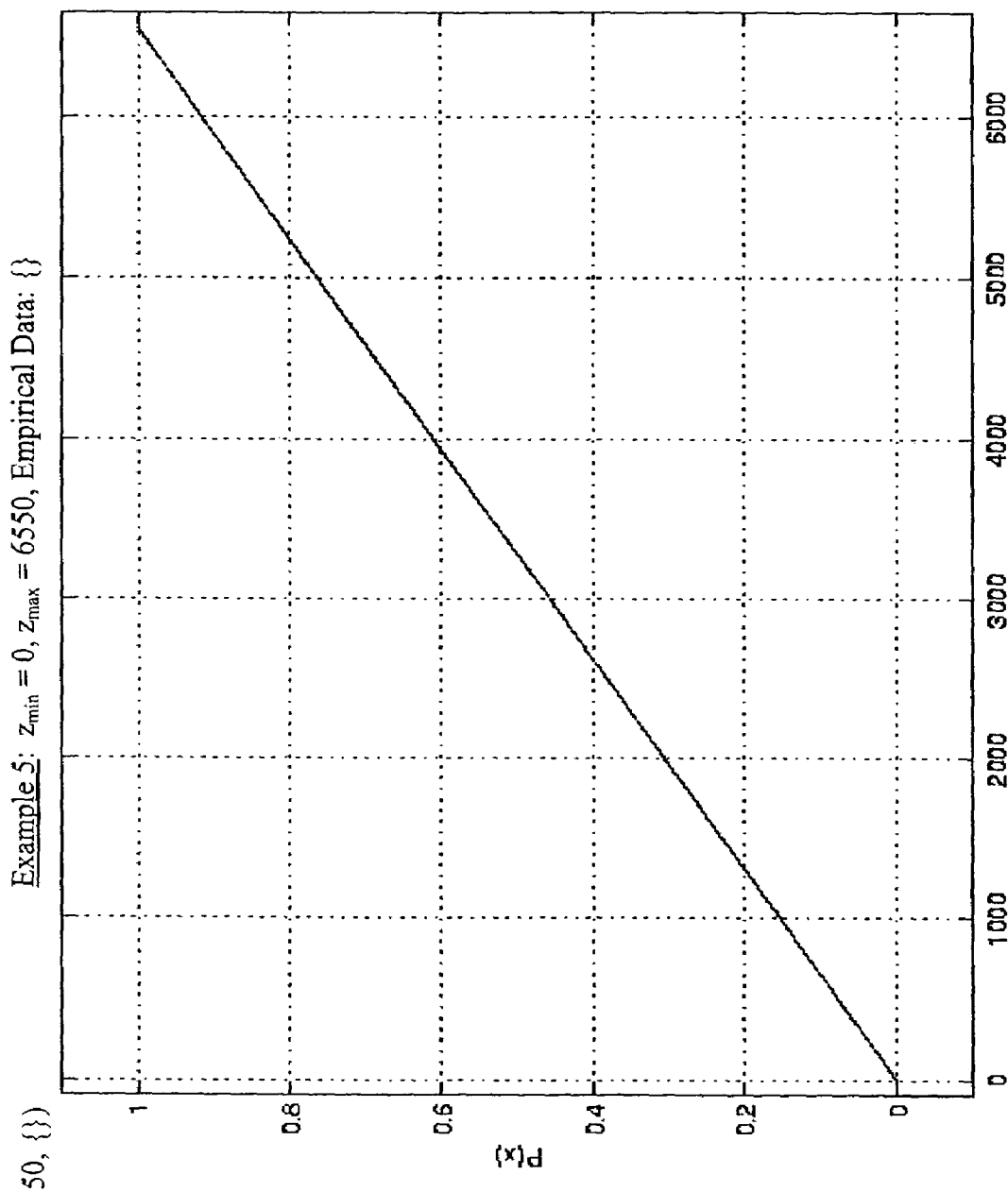

FIG. 27 shows a flow diagram (process) 2700 for closed loop therapy including hardware and software blanking in accordance with an embodiment of the invention where the nervous system disorder being treated is a seizure and the treatment therapy is electrical stimulation. Step 2701 initiates signal processing by the seizure detection algorithm 800. In step 2703, the seizure detection algorithm 800 determines whether or not a seizure has been detected. In the embodiment, an output ratio (e.g., the maximum ratio 2203 that is associated with the waveforms 2253, 2255, 2257, or 2259 as shown in FIG. 22) exceeds a predetermined threshold (e.g., the threshold 2211) for longer than a given time duration. In the embodiment, the corresponding signal(s) may be obtained from an electrode or from a group of electrodes (selected from the electrodes 101). In step 2705, a beginning of a detection cluster is recognized in accordance with the seizure detection algorithm 800. Detection of a seizure will trigger delivery of a treatment therapy (in this case stimulation), which may be redelivered during a detection cluster (e.g., cluster duration 2205) until the seizure has been terminated or safety limits (such as maximum stimulation on time per given period of time) have been reached or tolerability becomes an issue. In accordance with the determined treatment, step 2709 is executed, in which stimulation to a selected electrode or group of electrodes is applied, hardware and software blanking are invoked, and a stimulation timer is initiated. (In other embodiments, the medical device system may utilize drug infusion or a combination of electrical stimulation and drug infusion to deliver treatment therapy.) When the stimulation timer has expired, as determined in step 2711, the stimulation pulse terminates, hardware blanking ceases, and an interstimulus interval (ISI) timer and a software blanking timer are started in step 2713. Processing of the signals is not resumed and the seizure detection algorithm's output (i.e., the output ratio and/or detection state) is held constant (throughout the hardware and software blanking periods,) until the software blanking timer has expired as determined in step 2715.

While the detection algorithm is being software blanked, no recorded data is provided to the algorithm (from the channels which are blanked) in order to avoid the simultaneously occurring hardware-blanking/reconnection artifacts and/or stimulation artifacts from adversely affecting the detection process. During these time intervals, the corresponding individual channel ratios that were computed at the instant the software blanking began are held constant throughout the period of software blanking. This is done to avoid, for example, terminating an active detection by setting the ratios to some lesser value. Ratios are allowed to fluctuate as data is analyzed on other non-software-blanked channels.

Referring to FIG. 27, when the software blanking timer has expired in step 2715, the algorithm resumes processing corresponding signals in step 2717. If the output ratio remains above the predetermined threshold 2211, indicating that detected activity is continuing as determined in step 2719, the ISI timer is reset and step 2721 determines if the ISI timer has expired. (The ISI timer sets a minimum ISI time between adjacent stimulation pulse trains.). If the ISI timer has expired, another stimulation pulse may be applied to the selected electrode or group of electrodes (as executed by step 2709) in accordance with the determined treatment therapy. (Moreover, the determined treatment therapy may apply subsequent stimulation pulses that are separated by a time greater than the minimum ISI time.) If the ISI timer has not expired, step 2719 is repeated. In step 2719, if the seizure detection algorithm 800 determines that the output ratio drops below the predetermined threshold 2211, a cluster timer (corresponding to the time threshold 2215 in FIG. 22) is initiated in step 2723. The cluster timer is also reset in step 2723

If the cluster timer (e.g., corresponding to time threshold 2215) has expired, as determined by step 2725 after reaching step 2723, the end of the detection cluster is recognized in step 2729 and data that is collected during the cluster duration, as well as some prior period of data that may be of interest, may be stored in a loop recording (e.g., SRAM and flash memory 605) in step 2731. (The expiration of the cluster timer is indicative of a maximum time duration that the output threshold can be below a predetermined threshold, e.g., predetermined threshold 2211, while the detection cluster is occurring. In other words, if the output threshold is below the predetermined threshold and the cluster timer expires, process 2700 determines that the detection cluster has ended.) Step 2701 is then repeated. A subsequent detection cluster may occur during the seizure, causing steps 2705–2731 to be repeated.

If the cluster timer has not expired, as determined by step 2725, seizure detection is performed in step 2727, as was performed in step 2703. Step 2727 determines if the detection cluster associated with the seizure, as detected in step 2703, continues due to a new seizure detection that occurs before the cluster timer expires. If so, the ISI timer is reset and step 2728 determines if the ISI timer has expired. If so (i.e., the detection cluster continues and the time between adjacent stimulation pulses is greater than the ISI minimum time), then step 2707 is repeated. If the ISI timer has not expired, then step 2727 is repeated. If step 2727 determines that a seizure is not detected, step 2725 is repeated.

Steps 2701–2731, as shown in FIG. 27, may be sequentially executed. However, in a variation of the embodiment some of the steps may be executed in parallel while other steps may be sequentially executed. For example, step 2701 (start/continue signal processing) may be executed in parallel with step 2731 (data storage).

Hardware and/or software blanking may be automatically applied based upon the results of applying signal quality control algorithms, such as those described above, to test the reliability of sensor signals. Application of signal quality control may at anytime result in continuous hardware or software blanking of a particular sensor due to artifact. However, signal quality control algorithms may also be applied to any of the sensor channels to determine if the applied therapy (e.g., stimulation) is causing artifacts that require hardware or software blanking during and after application of the therapy. Those sensor channels determined not to be affected by the application of the treatment therapy do not need to be blanked, thus enhancing the ability of the system to monitor the patient. In addition, periodic checking of a sensor channel following a treatment pulse and applying signal quality algorithms can automatically determine the length of time needed for hardware and/or software blanking for that channel during future applications of the therapy. For example, a signal that is associated with an electrode in proximity of a stimulated electrode may be analyzed to have artifact characteristics, including during a time interval in which an artifact affects the signal. Alternatively, parameters of the therapy treatment may be adjusted within a range of values known to be therapeutic in an effort to reduce the effect on the signal quality of adjacent sensors. In this manner the medical device system can enhance it's ability to collect data while providing treatment therapy.

Even though hardware blanking is generated during the time interval in which an electrode is being stimulated, hardware blanking may be generated for other time intervals in which the associated amplifier may experience saturation (clipping or overload). The need for software blanking may be determined from geometric and electrical configurations of the electrodes, e.g., distance between electrodes and the stimulation intensity that may be measured by stimulation voltage). For example, the inducement of artifacts on a channel may be inversely related to the corresponding electrode and the stimulated electrode.

In an embodiment, software blanking may be determined by a calibration process in which an electrode is stimulated and the corresponding artifacts are measured for adjacent electrodes. For example, an artifact may be determined by stimulating a first electrode and measuring the artifact on a channel of a second electrode. The artifact may be determined by measuring a signal perturbation on the channel with respect to the signal on the channel without stimulating the first electrode. The procedure may be repeated by individually stimulating other electrodes. Alternatively, an impedance of the second electrode may be measured while stimulating the first electrode to determine an effect on the measured impedance.

Multi-Modal and Long-Term Ambulatory

The medical device system may support multi-modal operation, in which operation is modified in accordance with the configuration of the medical device system. One skilled in the art will recognize that the implanted system 10 (as shown in FIG. 12) may be more limited in functionality and features when compared to hybrid system (e.g., as shown in FIG. 9) due to the need to conserve the limited amount of energy available in a totally implanted system. One approach to expanding the capabilities is to incorporate a rechargeable battery in the implanted system 10. An alternative approach is to partition some of the features, particularly those that consume the most energy and are not used all the time, to the external portion 950 of a hybrid system or another external component of a hybrid system that may be associated with a process step, e.g., step 2025 of process 2000 as described in FIG. 20. (As previously discussed, FIG. 10 shows an exemplary embodiment of the external portion 950 with the associated programmer 1021.) In one embodiment, the medical device system operates as a closed-loop stimulator, in which stimulation therapy is adjusted in accordance with signal measurements and analysis that is performed. The electronics and software required to operate the closed loop control reside in the external portion 950 of a hybrid system or the external wearable signal processor 1425 in a hybrid system with a telemetry booster stage or relaying module. However, if the closed-loop control is removed from the configuration, corresponding to a removal of the external portion 950, the medical device system may operate as an open loop stimulator, in which electrodes with associated implanted electronics generate stimulation therapy. An external component may be removed for different reasons. For example, the external portion 950 may be removed at times when monitoring or when therapy features executed by the external portion are not required, such as at night, for patients who do not require closed-loop control while sleeping. Also, an external component may be configured in a medical device system in order to invoke optional functionality or enhanced functionality, in which the external component interacts with an implanted component.

An alternative embodiment incorporates both closed loop control and open-loop control of therapy in the implanted portion 950 with added features being supported by an external component, e.g., external portion 950 or external wearable signal processor 1425. In the embodiment, the external portion 953 operates in conjunction with the implanted portion 953 to provide an added function. For example, the external portion 950 may receive neurological data from the implanted portion 953 through a communications channel (e.g., a hardwire or a telemetry link) and support an added feature in accordance with the neurological data. The added feature may enhance functionality that is provided by an implanted component and may provide additional functionality to the medical device system. Examples of corresponding added features may include loop recording of segments of signals obtained from sensors such as EEG, emergency care features such as sounding an alarm or providing a cue to warn the patient of an impending medical condition, and making a cell phone telephone call to a care giver or health care professional if the medical condition of the patient changes. Additional information may be included with the neurological data and may be indicative of the patient's location, where the location may be determined by a Global Positioning System (GPS) receiver that interfaces with the medical device system. Activation of a loop recording function may be established by the physician or by a caregiver or patient with physician guidance using a programmer, e.g., the programmer 1021. Loop recording causes a segment of one or more monitored signals occurring around an automatically detected event or selected by the user to be stored in a memory. Programming of implanted portion 953 includes communicating over a communications channel using programmer 1021. The messages sent from programmer 1021 to implanted portion 953 include instructions, parameters, and/or firmware algorithms that establish conditions under which the loop recording is activated. Exemplary conditions that may initiate loop recording including recognition of specific characteristics of monitored signals such as the occurrence of a neurological event, established by the physician in general or specifically for the individual and programmed into the memory of the implanted portion 953. Conditions may also include manual triggers activated by the patient or caregiver or specific times of the day when loop recording should occur. Conditions for loop recording may also include certain types of errors or aberrant monitored signals such as those recognized by signal quality control algorithms that may be stored for later analysis. Manual triggers activated by the patient or caregiver may include, but are not limited to, subjective or visible manifestations of an event, or the point in time when a treatment therapy is delivered triggering storage of the signals after an appropriate time delay or when meals or beverages are consumed that may affect the physiological parameter being sensed by sensors in implantable device 953.

An alternative embodiment incorporates the same functionality in both implanted portion 953 and external portion 950 but where the external portion 950 enhances the functionality with added capacity to execute a specific mode of operation. For example, memory capacity of implanted portion 953 may limit the amount of time and/or number of monitored signals stored during loop recording. Periodic use of external portion 950 to download the contents of the memory of the implanted portion 953 to the external portion 950 for storage until the downloaded data can be transferred to physician programmer 1021 may expand the system capabilities. In another embodiment, external portion 950 may include a connection (e.g., with a modem) to the Internet allowing data about the performance of the system that is obtained during loop recording to be transmitted to the physician. Alternatively, programming instructions may be sent by the physician to the external and/or implanted portions.

Moreover, an external component, e.g., the external portion 950, may send data to an implanted component, e.g., the implanted portion 953. Programming of implanted device 953 may be accomplished using programmer 1021 communicating directly with implanted portion 953. This method is acceptable when all the communication protocols and operational features required for communication between implanted portion 953 and external portion 950 are fixed. In those instances when modes of operation must be coordinated between implanted portion 953 and external portion 950, it may be more efficient to program the implanted portion 953 by first programming external portion 950, which in turn sends data corresponding to appropriate instructions and receives confirmation of receipt from implanted portion 953 via antenna 955. Those skilled in the art will recognize that the reverse operation of programming implanted portion 953 that in turn communicates with external portion 950 is possible. However, this mode of operation requires two telemetry operations while programming of external device 950 directly can be accomplished using a hard wire connection.

In one embodiment of multi-modal operation, the operation by implanted portion 953 of features requiring an external portion 950 may be dependent upon an on-going communication between implanted portion 953 and external portion 950. In one instance, implanted device 953 periodically sends a signal to external device 950 confirming its mode of operation by providing an indication of the presence of the external portion 950. (If the implanted portion 953 does not receive a signal from the external portion 950 within a specified period of time, the implanted portion 953 may assume that the external portion 950 is not connected to the implanted portion 953.) Implanted portion 953 continues to support features requiring the external portion 950 until such time that implanted portion 953 detects that external portion 950 is no longer available. At this point, implantable portion 953 transitions to another mode of operation that does not require the external portion 950. In such a case, the implantable device 953 supports features that can be supported without interaction to the external device 950. For example, the implantable portion 953 may continue delivering treatment therapy in the open-loop mode (i.e., without feedback using neurological data), even though the implantable portion 953 delivers treatment therapy in the closed-loop mode (i.e., with feedback using neurological data) when operating in conjunction with the external portion 950.

Multi-Modal operation may also include simultaneous operation of several modes of operation of a medical device system, where a plurality of features may be supported during the same treatment interval. Simultaneous operation may occur with different medical device system architectures such as external system 100, the hybrid system as shown in FIGS. 9 and 10, or a hybrid system with telemetry booster 1415 (as shown in FIG. 14). In this embodiment, a first feature may support treatment therapy in an open loop fashion such as a prophylactic treatment to prevent a medical condition. Simultaneously, a second feature may support an algorithm that monitors sensors for prescribed conditions that trigger delivery of incremental therapy. In one embodiment, the device in FIG. 13 may employ an infusion system to provide a pharmaceutical agent in a continuous or intermittent manner to reduce the likelihood of a neurological condition from occurring. However, under prescribed conditions, the medical device system may also provide stimulation to respond to an instantaneous change in the medical condition in a closed-loop fashion. The incremental therapy may occur in response to changes in the values of sensors or a trigger input by the patient. The triggers or sensor changes may also start loop-recording of signals or values of parameters (corresponding to a third feature) and/or communicate with health care professionals via telephone/cell phone links (corresponding to a fourth feature). For example, there may be communications to the patient with instructions to take oral medication.

The medical device system may support multi-modal operation, in which operation is modified in accordance with the configuration of the medical device system. In one embodiment, the medical device system operates as a closed-loop stimulator, in which stimulation therapy is adjusted in accordance with signal measurements and analysis that is performed. However, if the closed-loop control is removed from the configuration, the medical device system operates as an open loop stimulator, in which electrodes with associated implanted electronics generate stimulation therapy.

Scoring of Sensed Neurological Signals

The system may further contain software modules or programs for scoring the severity of sensed neurological signals relating to a nervous system disorder. In particular, the system may monitor sensed neurological signals and compute a relative severity of the events associated with the neurological signal. Thus, each seizure detection may be ranked based on the relative severity score. This process may be performed for each neurological signal that is sensed by the system. Moreover this process may be performed in an implanted device or an external device. If performed in the implanted device, the ranked information may telemetered to the external device for further processing and/or display.

A seizure event may include, for example, a detected specified event and a reported event. Examples of a detected specified event include, without limitation, an occurrence of a maximal intensity, an extent of electrographic spread, or a number of detection clusters per unit time exceeding a corresponding predetermined threshold. A detected specified event may be associated with a detection cluster, in which the time duration of the detection cluster or the number of detections within a detection cluster may be further specified. A reported event is a seizure event that the patient perceives and reports, for example, by a button press.

The system may be programmed to analyze one or more particular features of the sensed neurological signal and automatically assign to each seizure event a "relative severity score" (RS) that is based on the particular feature(s) being considered. Examples of features to be ranked include, without limitation, a maximum ratio (i.e., peak instantaneous intensity level or ratio of foreground seizure activity vs. background activity), duration of the seizure detection, spread (number of monitoring elements involved in the event as previously discussed in the context of FIG. 22), number of clusters per unit time, number of detections within a cluster, duration of an event cluster, mean or median duration of a detections, and an inter-seizure interval.

By having a relative severity score for each seizure event, the external system 200 may thereby rank events by severity relative to other events and provide a means of visually displaying (i.e., loop recordings) and listing (summary records) the information. To determine severity, a formula using algorithm-based measures of seizure activity may be used by relating the duration, intensity, and extent of electrographic spread of a seizure. The external system 200 allows the user to determine which events are to be included/excluded from relative severity score computations. This feature may be programmable. The external system 200 has a means of manually and/or automatically computing the subject's Relative Severity Minimum (RS Min), in which the lowest relative severity score associated with clinical manifestations or other behaviors indicative of seizure activity is used to minimize the probability of missing clinical seizures. Seizures with scores close to or above the RS Min not associated with event markings or recorded in a clinician's notes may then be visually reviewed to determine if they have clinical manifestations.

In an embodiment, the system is capable of computing the relative severity of detected specified events within a comparable parameter configuration. Each detected specified event has four associated features to be measured: (1) max ratio; (2) duration; (3) spread; and (4) investigator classification. These features can be denoted by the vector X=(R, D, I; C), where R=max ratio, D=duration, I=Number of involved channels, and C=investigator classification (i.e., TPC, TPNC, FP, or NR). "TP" denotes either TPC or TPNC, and denotes "True Positive" detection. TPC denotes a "True Positive Clinical" detection with clinical manifestations, and TPNC denotes a "True Positive Non-Clinical" detection absent clinical manifestations. FP denotes a "False Positive" and NR denotes a detection that has thus far been "Not Reviewed." The following describes a specification for the relative severity function that uses all such detection clusters (obtained from analysis sessions that have comparable parameter configurations) as inputs and produces as an output a severity score for each such detection cluster.

In some embodiments, it may be difficult to detect clinical manifestations. For example, a seizure may be clinically apparent only if a patient is performing some action when the seizure occurs. In other embodiments of the invention, additional investigator classifications may be defined. For example, an investigator classification "Non-classifiable" or "Difficult to Classify" may be used if the investigator cannot determine is not able to classify the event. Also, an investigator classification "Epileptiform Discharges" may be defined to help identify the impact that treating epileptiform discharges may have on seizure frequency.

The relative severity scores are computed using an "interpolating empirical probability function" (defined below) derived from all detection clusters in the comparable parameter set that have been previously scored by the investigator as TRUE POSITIVES. (However, scoring is not limited to TRUE POSITIVES an may encompass other investigator classifications.) The function also utilizes the possible ranges of R, D, and I in the calculation (e.g., in the a priori case when there are no TPs marked yet because no review has been performed). For example, suppose these ranges are:

$$R_{min} = D_{min} = 0,$$

$$R_{max} = 6550, D_{max} = 65536 \text{ (frames)}, I_{max} = 8.$$

Suppose that there are N prior true positive detection clusters from among M total detection clusters ($0 \leq N \leq M$). It is assumed that all detection clusters are associated with the same comparable detection parameter configuration. The relative severity computations are performed separately and independently on each different parameter configuration's set of detection clusters. The relative severity score of a particular detection cluster Y=(R, D, I; C) may be determined by the following formula:

$$RS(Y) = \text{Round}(100*(p_1+p_2+p_3)/3)$$

where $p_1 = P(R; R_{min}, R_{max}, \{R_j | \text{cluster } j \text{ is a } TP\})$, $p_2 = P(D; D_{min}, D_{max}, \{D_j | \text{cluster } j \text{ is a } TP\})$, and $p_3 = P(I; I_{min}, I_{max}, \{I_j | \text{cluster } j \text{ is a } TP\})$.

where P is the interpolating empirical probability function (IEPF) described below.

The interpolating empirical probability function can now be described. Given some empirical data values $z_1, z_2, \ldots, z_N$ which are sorted in increasing order and which lie in a range $[z_{min}, z_{max}]$ (with $z_{min} < z_{max}$), define the interpolating empirical probability function, $P(x; z_{min}, z_{max}, \{z_1, \ldots, z_N\})$, as follows. In the first case where $N > 0$:

$$P(x; z_{min}, z_{max}, \{z_1, \ldots, z_N\}) = \begin{cases} 0 & \text{if } x < z_{min} \\ \frac{1}{N+1}\left(\frac{x - z_{min}}{z_1 - z_{min}}\right) & \text{if } z_{min} \leq x < z_1 \\ \frac{1}{N+1}\left(i + \frac{x - z_i}{z_{i+1} - z_i}\right) & \text{if } z_i < x < z_{i+1} \text{ for some } i \\ \frac{1}{2(N+1)}\left(1 + \sum_{j=1}^{N}\left(1_{\{z_j \leq x\}} + 1_{\{z_j < x\}}\right)\right) & \text{if } x = z_i \text{ for some } i \\ \frac{1}{N+1}\left(N + \frac{x - z_N}{z_{max} - z_N}\right) & \text{if } z_N < x \leq z_{max} \\ 1 & \text{if } z_{max} < x \end{cases}$$

Here, $1_{\{\cdot\}}$ denotes the indicator function of the set $\{\cdot\}$. In the second case where $N=0$:

$$P(x; z_{min}, z_{max}, \{\}) = \frac{\min\{\max\{x, z_{min}\}, z_{max}\} - z_{min}}{z_{max} - z_{min}}$$

FIGS. 28–33 depict various examples. As an example, suppose there are 4 scored True Positive detection clusters as follows:

| $R_{max}$ | D (s) | I | C |
|---|---|---|---|
| 103.1 | 35.2 | 6 | TPC |
| 115.6 | 41.3 | 4 | TPNC |
| 34.7 | 18.9 | 6 | TPNC |
| 189.9 | 55.1 | 8 | TPC |

Next suppose 4 more detection clusters are obtained which are presently not reviewed as follows:

| $R_{max}$ | D (s) | I | C |
|---|---|---|---|
| 200.3 | 12.6 | 5 | NR |
| 49.5 | 83.2 | 6 | NR |
| 2653.2 | 4.2 | 1 | NR |
| 122.4 | 6.9 | 3 | NR |

The following table illustrates the results of determining the RS score for each detection.

| | $R_{max}$ | $p_1$ | D | $p_2$ | I | $p_3$ | RS |
|---|---|---|---|---|---|---|---|
| TP | 103.1 | 0.4 | 35.2 | 0.4 | 6 | 0.5 | 43 |
| | 115.6 | 0.6 | 41.3 | 0.6 | 4 | 0.2 | 47 |
| | 34.7 | 0.2 | 18.9 | 0.2 | 6 | 0.5 | 30 |
| | 189.9 | 0.8 | 55.1 | 0.8 | 8 | 0.8 | 80 |
| NR | 200.3 | 0.80032704 | 12.6 | 0.133333 | 5 | 0.3 | 41 |
| | 49.5 | 0.24327485 | 83.2 | 0.801818 | 6 | 0.5 | 52 |
| | 2653.2 | 0.87746105 | 4.2 | 0.0444444 | 1 | 0.05 | 32 |
| | 122.4 | 0.61830417 | 6.9 | 0.0730159 | 3 | 0.15 | 28 |

Note that the interpolating empirical probability functions used to determine the pi values are determined using only the TP values, then evaluated for both the TP and NR detection clusters to determine the severity.

If, instead, all of the detection clusters had not yet been scored (or at least not scored as TPs), the severity computations would be changed as shown in the following table.

| | $R_{max}$ | $p_1$ | D | $p_2$ | I | $p_3$ | RS |
|---|---|---|---|---|---|---|---|
| NR | 103.1 | 0.0157 | 35.2 | 0.0112 | 6 | 0.7500 | 26 |
| | 115.6 | 0.0176 | 41.3 | 0.0131 | 4 | 0.5000 | 18 |
| | 34.7 | 0.0053 | 18.9 | 0.0060 | 6 | 0.7500 | 25 |
| | 189.9 | 0.0290 | 55.1 | 0.0175 | 8 | 1.0000 | 35 |
| | 200.3 | 0.0306 | 12.6 | 0.0040 | 5 | 0.6250 | 22 |
| | 49.5 | 0.0076 | 83.2 | 0.0264 | 6 | 0.7500 | 26 |
| | 2653.2 | 0.4051 | 4.2 | 0.0013 | 1 | 0.1250 | 18 |
| | 122.4 | 0.0187 | 6.9 | 0.0022 | 3 | 0.3750 | 13 |

On the other hand, if all had been scored as TPs, then the RS scores would be evaluated as shown in the following table.

| | $R_{max}$ | $p_1$ | D | $p_2$ | I | $p_3$ | RS |
|---|---|---|---|---|---|---|---|
| TP | 103.1 | 0.3333 | 35.2 | 0.5556 | 6 | 0.6667 | 52 |
| | 115.6 | 0.4444 | 41.3 | 0.6667 | 4 | 0.3333 | 48 |
| | 34.7 | 0.1111 | 18.9 | 0.4444 | 6 | 0.6667 | 41 |
| | 189.9 | 0.6667 | 55.1 | 0.7778 | 8 | 0.8889 | 78 |
| | 200.3 | 0.7778 | 12.6 | 0.3333 | 5 | 0.4444 | 52 |
| | 49.5 | 0.2222 | 83.2 | 0.8889 | 6 | 0.6667 | 59 |
| | 2653.2 | 0.8889 | 4.2 | 0.1111 | 1 | 0.1111 | 37 |
| | 122.4 | 0.5556 | 6.9 | 0.2222 | 3 | 0.2222 | 33 |

The above examples illustrate the determination of the relative severity score with a data corresponding to a mixture of true positive detection clusters and not reviewed detection clusters, with data corresponding only to true positive detection clusters, and to data corresponding only to not reviewed detection clusters.

In an embodiment, the medical device system may be modularly expandable in order to add a feature that may enhance existing functionality or that may support additional functionality. An external component, e.g., external portion 950, may include a module that supports the added feature. The module may be implemented with dedicated hardware and/or computer-executable instructions that are performed by an associated processor. In another embodiment, the module may be associated with another external component that couples to the external component. As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Thus, embodiments of the SIGNAL QUALITY MONITORING AND CONTROL FOR A MEDICAL DEVICE SYSTEM are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. In a medical device system having a plurality of monitoring elements, a method for detecting poor signal quality comprising the steps of:
    (a) receiving a neurological signal from one of the monitoring elements;
    (b) processing the received signal to generate a plurality of data points for the signal in a moving time window;
    (c) detecting that the received signal has poor signal quality by determining that an amount of the data points exhibiting poor signal quality within the moving time window has exceeded a predetermined threshold; and
    (d) ignoring the received signal experiencing poor signal quality in signal processing.

2. The method of claim 1, further comprising the step of (e) delivering a notification that the signal from one of the monitoring elements is experiencing poor signal quality.

3. The method of claim 1, further comprising the step of (e) providing a substituted signal for the ignored signal experiencing poor signal quality.

4. The method of claim 1, wherein the step of detecting comprises the step of determining that percentage of the data points exhibiting poor signal quality within the moving time window has exceeded a predetermined threshold percentage.

5. The method of claim 1, wherein the step of ignoring comprises the step of ignoring the received signal experiencing poor signal quality in a closed-loop feedback control of a treatment therapy.

6. The method of claim 1, wherein the step of receiving comprises the step of receiving the neurological signal selected from the group consisting of an electrical signal, a chemical signal, a biological signal, a temperature signal, a pressure signal, a respiration signal, a heart rate signal, a ph-level signal, and a peripheral nerve signal.

7. The method of claim 1, wherein the step of receiving comprises the step of receiving the signal from the monitoring element selected from the group consisting of an electrode and a sensor.

8. The method of claim 1, wherein the step of processing comprises the step of identifying a value of at least one variable quantifying signal quality.

9. The method of claim 8, wherein the step of identifying a value comprises the step of determining a flat-line fraction signal to determine whether a signal is experiencing a flat-lining artifact.

10. The method of claim 8, wherein the step of identifying a value comprises the step of determining a flat-line fraction signal to determine whether a signal is experiencing amplifier saturation clipping.

11. The method of claim 8, wherein the step of identifying a data value comprises the step of determining an amplitude at a predetermined frequency to determine whether a signal is experiencing a mains artifact.

12. The method of claim 11, wherein the step of determining an amplitude comprises the step of determine an amplitude at about 60 Hz.

13. The method of claim 11, wherein the step of determining an amplitude comprises the step of determine an amplitude at about 50 Hz.

14. The method of claim 11, further comprising the step of (e) resuming consideration of the poor signal in the closed-loop feedback control once it is determined that the amount of the data points exhibiting poor signal quality within the time window has fallen below a second threshold.

15. The method of claim 1, wherein the step of detecting comprises the step of performing a time-averaging of the data points.

16. The method of claim 1, wherein the step of detecting comprises the step of performing a time-averaging of the data points using exponential forgetting.

17. The method of claim 1, wherein the step of receiving further comprises the step of receiving the neurological signal for purposes of providing closed-loop feedback control of a treatment therapy.

18. The method of claim 1, wherein step (c) comprises:
    (i) determining a signal power to noise power ratio.

19. The method of claim 1, wherein step (c) comprises:
    (i) determining a fraction of a foreground window that contains noisy data.

20. The method of claim of claim 1, further comprising:
    (e) detecting a movement artifact with at least one accelerometer; and
    (f) utilizing an output of the at least one accelerometer to reduce the movement artifact.

21. A medical device system for managing a nervous system disorder and capable of detecting poor signal quality comprising in combination:
    (a) at least one monitoring element, each generating a neurological signal of a sensed neurological condition; and
    (b) computer executable instructions for performing the steps of (i) generating a plurality of instantaneous data points of the received neurological signal for a moving time window; (ii) detecting that the received signal has poor signal quality by determining that an amount of the data points exhibiting poor signal quality within the time window has exceeded a predetermined threshold; and (iii) ignoring the received signal experiencing poor signal quality in signal processing.

22. The medical device system of claim 21, wherein computer executable instructions further performs the step (iv) delivering a notification that the signal from one of the monitoring elements is experiencing poor signal quality.

23. The medical device system of claim 21, wherein computer executable instructions further performs the step (iv) providing a substituted signal for the ignored signal experiencing poor signal quality.

24. The medical device system of claim 21, wherein the step of detecting comprises the step of determining that percentage of the data points exhibiting poor signal quality within the moving time window has exceeded a predetermined threshold percentage.

25. The medical device system of claim 21, wherein the step of ignoring comprises the step of ignoring the received signal experiencing poor signal quality in a closed-loop feedback control of a treatment therapy.

26. The medical device system of claim 21, wherein the nervous system disorder is selected from the group consisting of a disorder of a central nervous system, a disorder of a peripheral nervous system, and mental health disorder, and psychiatric disorder.

27. The medical device system of claim 21, wherein the nervous system disorder is selected from the group consisting of epilepsy, Parkinson's disease, essential tremor, dystonia, multiple sclerosis (MS), anxiety, a mood disorder, a sleep disorder, obesity, and anorexia.

28. The medical device system of claim 21, wherein the treatment therapy is selected from the group consisting of electrical stimulation, magnetic stimulation, drug infusion, and brain cooling.

29. The medical device system of claim 21, wherein the neurological signal is selected from the group consisting of a electrical signal, a chemical signal, a biological signal, a temperature signal, a pressure signal, a respiration signal, a heart rate signal, a ph-level signal, and a peripheral nerve signal.

30. The medical device system of claim 21, wherein the monitoring element is selected from the group consisting of an electrode and a sensor.

31. The medical device system of claim 21, wherein the medical device system is selected from the group consisting of an external system, a hybrid system, and an implanted system.

32. The medical device system of claim 21, wherein the computer executable instructions are further configured to perform the step of identifying a data value of at least one parameter.

33. The medical device system of claim 21, wherein the computer executable instructions are further configured to perform the step of identifying a data value by determining a clip fraction signal to determine whether a signal is experiencing a clipping artifact.

34. The medical device system of claim 21, wherein the computer executable instructions are further configured to perform the step of identifying a data value by determining an amplitude at a predetermined frequency to determine whether a signal is experiencing a mains artifact.

35. The medical device system of claim 34, wherein the step of determining an amplitude comprises the step of determine an amplitude at about 60 Hz.

36. The medical device system of claim 21, wherein the step of determining an amplitude comprises the step of determine an amplitude at about 50 Hz.

37. The medical device system of claim 21, wherein the computer executable instructions are further configured to perform the step of (iv) resuming consideration of the poor signal in the closed-loop feedback control once it is determined that the amount of the data points exhibiting poor signal quality within the time window has fallen below a second threshold.

* * * * *